US010626184B2

(12) United States Patent
Schwaeble et al.

(10) Patent No.: US 10,626,184 B2
(45) Date of Patent: Apr. 21, 2020

(54) MONOCLONAL ANTIBODIES, COMPOSITIONS AND METHODS FOR DETECTING MUCIN-LIKE PROTEIN (MLP) AS A BIOMARKER FOR OVARIAN AND PANCREATIC CANCER

(71) Applicants: University of Leicester, Leicester (GB); Omeros Corporation, Seattle, WA (US)

(72) Inventors: Hans-Wilhelm Schwaeble, Mountsorrel (GB); Gregory A. Demopulos, Mercer Island, WA (US)

(73) Assignees: Omeros Corporation, Seattle, WA (US); University of Leicester, Leicester (GB)

( * ) Notice: Subject to any disclaimer, the term of this patent is extended or adjusted under 35 U.S.C. 154(b) by 0 days.

(21) Appl. No.: 15/615,588

(22) Filed: Jun. 6, 2017

(65) Prior Publication Data

US 2017/0355777 A1 Dec. 14, 2017

Related U.S. Application Data

(60) Provisional application No. 62/347,824, filed on Jun. 9, 2016.

(51) Int. Cl.

| *C07K 16/30* | (2006.01) |
| *C07K 16/40* | (2006.01) |
| *C07K 14/47* | (2006.01) |
| *A61K 47/68* | (2017.01) |
| *G01N 33/574* | (2006.01) |

(52) U.S. Cl.
CPC ...... *C07K 16/3092* (2013.01); *A61K 47/6859* (2017.08); *A61K 47/6869* (2017.08); *C07K 14/4727* (2013.01); *C07K 16/3015* (2013.01); *G01N 33/57438* (2013.01); *G01N 33/57449* (2013.01); *G01N 33/57492* (2013.01); *C07K 2317/34* (2013.01); *C07K 2317/56* (2013.01); *C07K 2317/565* (2013.01); *G01N 2333/4725* (2013.01)

(58) Field of Classification Search
CPC ............ C07K 16/3092; C07K 16/3015; C07K 47/6869
USPC .......................................... 424/133.1, 178.1
See application file for complete search history.

(56) References Cited

U.S. PATENT DOCUMENTS

| 4,737,456 A | 4/1988 | Weng et al. |
| 4,816,567 A | 3/1989 | Cabilly et al. |
| 5,057,313 A | 10/1991 | Shih et al. |
| 5,211,657 A | 5/1993 | Yamada et al. |
| 5,443,953 A | 8/1995 | Hansen et al. |
| 5,530,101 A | 6/1996 | Queen et al. |
| 5,582,826 A | 12/1996 | Shimamura |
| 5,585,089 A | 12/1996 | Queen et al. |
| 5,693,762 A | 12/1997 | Queen et al. |
| 6,180,377 B1 | 1/2001 | Morgan et al. |
| 2004/0010119 A1* | 1/2004 | Guo ........................ C07K 14/47 530/350 |
| 2004/0237124 A1 | 11/2004 | Pons et al. |
| 2010/0183618 A1 | 7/2010 | Hasegawa |
| 2010/0203559 A1 | 8/2010 | Ester |
| 2014/0364341 A1 | 12/2014 | Mansfield et al. |

FOREIGN PATENT DOCUMENTS

| WO | WO 1998/045322 | 10/1998 |
| WO | WO 1998/048014 | 10/1998 |
| WO | WO 2013/007052 | 1/2013 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Kohler, G., et al., "Continuous cultures of fused cells secreting antibody of predefined specificity," *Nature*, 256(5517): 495-497, (1975).
Clackson, T., et al., "Making antibody fragments using phage display libraries," *Nature*, 352(6336): 624-628, (1991).
Riechmann, L., et al., "Reshaping human antibodies for therapy," *Nature*, 332(6162): 323-327, (1988).
Verhoeyen, M., et al., "Reshaping human antibodies: grafting an antilysozyme activity," *Science*, 239(4847): 1534-1536, (1988).
Holliger, P., et al., "Engineering bispecific antibodies," *Curr Opin Biotechnol*, 4(4): 446-449, (1993).
UniProtKB, "Q9Y3S4 (Q9Y3S4_HUMAN)," EMBL, (1999).
UniProtKB, "T5LVR8 (T5LVR8_9Firm)," EMLB, (2013).
Andrianifahanana, M., et al., "Regulation of mucin expression: mechanistic aspects and implications for cancer and inflammatory diseases," *Biochimica Et Biophysica Acta Reviews on Cancer*, 1765(2):189-222, (2006).
Bafna, S., et al., "Membrane-bound mucins: the mechanistic basis for alterations in the growth and survival of cancer cells," *Oncogene*, 29(20): 2893-2904, (2010).
Bitter, G. A., et al., "Expression and secretion vectors for yeast," *Methods Enzymol*, 153: 516-544, (1987).
Brockhausen, I., "Mucin-type O-glycans in human colon and breast cancer: glycodynamics and functions," *EMBO Rep*, 7(6): 599-604, (2006).
Chauhan, S. C., et al., "Mucins in ovarian cancer diagnosis and therapy," *J Ovarian Res*, 2: 21, (2009).

(Continued)

Primary Examiner — Lynn A Bristol
(74) Attorney, Agent, or Firm — Tineka J. Quinton

(57) ABSTRACT

In various embodiments the invention provides anti-mucin-like protein (MLP) monoclonal antibodies, compositions and methods for detecting MLP as a biomarker for mucin-secreting type of cancer such as ovarian or pancreatic cancer.

10 Claims, 12 Drawing Sheets

Specification includes a Sequence Listing.

(56) References Cited

OTHER PUBLICATIONS

Chen, Y., et al., "Genome-wide search and identification of a novel gel-forming mucin MUC19/Muc19 in glandular tissues," *Am J Respir Cell Mol Biol*, 30(2): 155-165, (2004).

Chothia, C., et al., "Canonical structures for the hypervariable regions of immunoglobulins," *J Mol Biol*, 196(4): 901-917, (1987).

Cohen et al., "Platinum-resistance in ovarian cancer cells is mediated by IL-6 secretion via the increased expression of its target cIAP-2," *Jour of Molecular Medicine*, 91(3): 357-368, 2013.

Costa, F. P., et al., "Prostasin, a potential tumor marker in ovarian cancer—a pilot study," *Clinics* (Sao Paulo), 64(7): 641-644, (2009).

Diamandis, E. P., et al., "Human Kallikrein 6 (hK6): A New Potential Serum Biomarker for Diagnosis and Prognosis of Ovarian Carcinoma," *Journal of Clinical Oncology* 21(6):1035-1043, (2003).

Field, J.K., et al., "Elevated expression of the c-myc oncoprotein correlates with poor prognosis in head and neck squamous cell carcinoma," *Oncogene* 4:1463 (1989).

Giuntoli, R. L., 2nd, et al., "Mucin gene expression in ovarian cancers," *Cancer Res*, 58(23): 5546-5550, (1998).

Gold, D. V., et al. "New MUC1 Serum Immunoassay Differentiates Pancreatic Cancer From Pancreatitis," *J Clin Oncol*. 24(2):252-58, 2006.

Graham, F. L., et al., "Characteristics of a human cell line transformed by DNA from human adenovirus type 5," *J Gen Virol*, 36(1): 59-74, (1977).

Guppy, A.E., et al., "Epithelial Ovarian Cancer: A Review of Current Management," *Clinical Oncology* 17(6):399-411, (2005).

Hamilton, T. C., et al., "Experimental model systems of ovarian cancer: applications to the design and evaluation of new treatment approaches," *Semin Oncol*, 11(3): 285-298, (1984).

Ho, S. B., et al., "Heterogeneity of mucin gene expression in normal and neoplastic tissues," *Cancer Res*, 53(3): 641-651, (1993).

Jones, P. T., et al., "Replacing the complementarity-determining regions in a human antibody with those from a mouse," *Nature*, 321(6069): 522-525, (1986).

Jordan, S.J., et al., "Does smoking increase risk of ovarian cancer? A systematic review," *Gynecologic Oncology* 103(3):1122-1129, (2006).

Kim, Y.S., et al., "Mucin glycoproteins in neoplasia," *Glycoconjugate Journal* 13(5):693-707, (1996).

Kim, Y-W, et al., "Development of Multiplexed Bead-Based Immunoassays for the Detection of Early Stage Ovarian Cancer Using a Combination of Serum Biomarkers," *PLoS One* 7(9): e44960, (2012).

Lefranc, M. P., et al., "IMGT, the international ImMunoGeneTics database," *Nucleic Acids Res*, 27(1): 209-212, (1999).

Leung, S., et al., "Engineering a unique glycosylation site for site-specific conjugation of haptens to antibody fragments," *J Immunol*. 154(11): 5919-26 (1995).

Logan, J., et al., "Adenovirus tripartite leader sequence enhances translation of mRNAs late after infection," *Proc Natl Acad Sci USA*, 81(12): 3655-3659, (1984).

Louie, K. G., et al., "Radiation survival parameters of antineoplastic drug-sensitive and -resistant human ovarian cancer cell lines and their modification by buthionine sulfoximine," *Cancer Res*, 45(5): 2110-2115, (1985).

Marks, J. D., et al., "By-passing immunization. Human antibodies from V-gene libraries displayed on phage," *J Mol Biol*, 222(3): 581-597, (1991).

Mather, J. P., "Establishment and characterization of two distinct mouse testicular epithelial cell lines," *Biol Reprod*, 23(1): 243-252, (1980).

Mather, J. P., et al., "Culture of testicular cells in hormone-supplemented serum-free medium," *Ann N Y Acad Sci*, 383: 44-68, (1982).

McLemore, M. R., et al., "Epidemiological and genetic factors associated with ovarian cancer," *Cancer Nurs*, 32(4): 281-288; quiz 289-290, (2009).

Modugno, F., et al., "Oral contraceptive use, reproductive history, and risk of epithelial ovarian cancer in women with and without endometriosis," *Am J Obstet Gynecol*, 191(3): 733-740, (2004).

Moore, J.P., et al., "Twin-Site ELISAs for fos and myc Oncoproteins Using the AMPAK System," *Methods in Molecular Biology* 10:273-281 (1992).

Moore, R. G., et al., "Utility of tumor marker HE4 to predict depth of myometrial invasion in endometrioid adenocarcinoma of the uterus," *Int J Gynecol Cancer*, 21(7): 1185-1190, (2011).

Nguyen, L., et al., "Biomarkers for early detection of ovarian cancer," *Womens Health* (Lond), 9(2): 171-185; quiz 186-177, (2013).

O'Sullivan, M. J., et al., "Methods for the preparation of enzyme-antibody conjugates for use in enzyme immunoassay," *Methods Enzymol*, 73(Pt B): 147-166, (1981).

Pluckthun, A., "Antibodies from *Escherichia coli*," *The Pharmacology of Monoclonal Antibodies*, Berlin, Springer Verlag, 11: 269-315, (1994).

Qoronfleh, M.W., et al., "Protein Biomarker Immunoassays: Opportunities and Challenges," *Drug Discovery World* Winter:19-28, (2010).

Richards, E. R., et al., "Antibodies reactive with the protein core of MUC1 mucin are present in ovarian cancer patients and healthy women," *Cancer Immunol Immunother*, 46(5): 245-252, (1998).

Rossing, M.A., et al., "Risk of epithelial ovarian cancer in relation to benign ovarian conditions and ovarian surgery," *Cancer Causes and Control* 19(10):1357-1364, (2008).

Ruiz, M., et al., "IMGT, the international ImMunoGeneTics database," *Nucleic Acids Res*, 28(1): 219-221, (2000).

Saltzman, W. M., et al., "Transport rates of proteins in porous materials with known microgeometry," *Biophys J*, 55(1): 163-171, (1989).

Sarojini, S., et al., "Early detection biomarkers for ovarian cancer," *J Oncol*, 2012: 709049, (2012).

Sherwood, J. K., et al., "Controlled antibody delivery systems," *Biotechnology* (N Y), 10(11): 1446-1449, (1992).

Shih, L.B., et al., "Site-specific linkage of methotrexate to monoclonal antibodies using an intermediate carrier," *Int J Cancer* 41(6):832-839 (1988).

Shih, L. B., et al., "A fluorouridine-anti-CEA immunoconjugate is therapeutically effective in a human colonic cancer xenograft model," *Int J Cancer*, 46(6): 1101-1106, (1990).

Sornsukolrat, S., et al., "Prognostic factors and survival of borderline ovarian tumors in Rajavithi Hospital between 1979-2006 A.D.," *J Med Assoc Thai* 95(9):1141-1148, 2012.

Spandidos, D., et al., "High levels of c-myc protein in human breast tumours determined by a sensitive ELISA technique," *AntiCancer Res*. 9(4): 821-6 (1989).

Stimpfl, M., et al., "Expression of mucins and cytokeratins in ovarian cancer cell lines," *Cancer Lett*, 145(1-2): 133-141, (1999).

Su, Z., et al., "Detection and monitoring of ovarian cancer," *Clin Chim Acta*, 415: 341-345, (2013).

Urlaub, G., et al., "Isolation of Chinese hamster cell mutants deficient in dihydrofolate reductase activity," Proc Natl Acad Sci U S A, 77(7): 4216-4220, (1980).

Winter, G., et al., "Man-made antibodies," *Nature*, 349(6307): 293-299, (1991).

Yamashita, Y., et al., "Alterations in gastric mucin with malignant transformation: novel pathway for mucin synthesis," *J Nat'l Cancer Inst*, 87(6): 441-446, (1995).

Yancik, R., "Ovarian cancer. Age contrasts in incidence, histology, disease stage at diagnosis, and mortality," *Cancer*, 71(2 Suppl): 517-523, (1993).

Yu, Z., et al., "Peptide-antibody conjugates for tumour therapy: A MHC-class-II-restricted tetanus toxin peptide coupled to an anti-IG light chain antibody can induce cytotoxic lysis of a human B-cell lymphoma by specic CD4 T cells," *Int. J. Cancer* 56(2): 244-248 (1994).

\* cited by examiner

MLP full length amino acid sequence
(431 aa, SEQ ID NO:1)

MKPRQKEQDTRLRKLRESSEGDQWLENEKTKPLRPQQQPQCQPAGGTGQRRGSGSSPSAD
QQGAQDREEEAAAAPAPTSRGHRTEKRPQQPQRRPAGGTGQRRGSRSSSADQQGAQDR
EEEAAAAPAPTSSGHRTEKRKPQQPQCRPAAGTGQRRGSGCSPSADQQRAQDREEEATAA
PVPTSSGHRTEKRKRLQLQCQPAGGTGQRRGSRSSPSADQQRAQDREEEAAAAPAPTSRG
HRTEKRKPQQPQRRPAAGTGQRRGSGSSPSADQQGAQDREEEAAAAPAPTSRGHRTEKRK
RLQPQRRPAGGTGQRRGSRSSPSADQQRAQDREEEAAAAPVPTSRGHRTEKRKRLQLQCQ
PAGGTGQRRGSGSSPSADQQRAQDREEEAAAAPAPTSSGHRTEKRKRQQPQRRPAAGTGQ
RRGSEEMEEEG

FIGURE 1 rMLP C-terminal fusion protein

MRGSHHHHHHGMASMTGGQQMGRDLYDDDDKDRWGSPGLQEFGTREEEAAAAPAPTSRGH
RTEKRKRLQPQRRPAGGTGQRRGSRSSPSADQQRAQDREEAAAAPVPTSRGHRTEKRKR
LQLQCQPAGGTGQRRGSGSSPSADQQRAQDREEEAAAAPAPTSSGHRTEKRKRQQPQRRP
AAGTGQRRGSEEMEEEG

FIGURE 2

Alignment of VH regions from Clones 11, B and C

```
         10        20        30        40        50        60        70        80        90       100       110       120  125
         +---------+---------+---------+---------+---------+---------+---------+---------+---------+---------+---------+----+
11  EVQLQQSGPELVKPGASVKISCKASGYAFTGFYINHHKQSHVKSLEHIG---RIHPYNGRTSYNQMFKDRASLTVDESSSTAYHEFYGLISEDSAVYYCARERVYYTGSTYEFDSNGQGTILTVSS
B   ..D.K..E..GG..Q..G.M.L.V...S......V.........PT....R...H....F...........F...................................F..........
C   ....................FT.SMYNHN.VR..PE.G...VAEI.LKSM.Y.IN.AESV.G.FTISR.D.K.SV.LDNNN.RA..TGI..TS----.GS.L.YL.Y.............
```

FIGURE 10A

Alignment of VL regions from Clones 11, B and C

```
            1          10         20         30         40         50         60         70         80         90         100        11012
            +----------+----------+----------+----------+----------+----------+----------+----------+----------+----------+----------+--+
11          DVLMTQTPLSLPVSLGDQASISCRSSQSIVHTSGVTYLSWYLQKPGQSPKLLIYKVFYRFSGVPDRFSGSGSGTDFTLKISRVESEDLGVYYCFQGSHVPPTFGAGTKLELK
B           QIVL..S.VINSA.P.EKVT...SA------.S...SNMY..Q....S...AM..RTSNLA....A..........SYS.T..SM.A..AAT...H.YQSY.R........
C           ............................S................................................A..........A.................T....I.
```

FIGURE 10B

SEQUENCE LISTING

```
<160> NUMBER OF SEQ ID NOS: 36

<210> SEQ ID NO 1
<211> LENGTH: 431
<212> TYPE: PRT
<213> ORGANISM: Homo sapiens

<400> SEQUENCE: 1

Met Lys Pro Arg Gln Lys Glu Gln Asp Thr Arg Leu Arg Lys Leu Arg
1               5                   10                  15

Glu Ser Ser Glu Gly Asp Gln Trp Leu Glu Asn Glu Lys Thr Lys Pro
            20                  25                  30

Leu Arg Pro Gln Gln Gln Pro Gln Cys Gln Pro Ala Gly Gly Thr Gly
        35                  40                  45

Gln Arg Arg Gly Ser Gly Ser Ser Pro Ser Ala Asp Gln Gln Gly Ala
    50                  55                  60

Gln Asp Arg Glu Glu Glu Ala Ala Ala Pro Ala Pro Thr Ser Arg
65                  70                  75                  80

Gly His Arg Thr Glu Lys Arg Lys Pro Gln Gln Pro Gln Arg Arg Pro
                85                  90                  95

Ala Gly Gly Thr Gly Gln Arg Arg Gly Ser Arg Ser Ser Ser Ser Ala
            100                 105                 110

Asp Gln Gln Gly Ala Gln Asp Arg Glu Glu Glu Ala Ala Ala Ala Pro
        115                 120                 125

Ala Pro Thr Ser Ser Gly His Arg Thr Glu Lys Arg Lys Pro Gln Gln
    130                 135                 140

Pro Gln Cys Arg Pro Ala Ala Gly Thr Gly Gln Arg Arg Gly Ser Gly
145                 150                 155                 160

Cys Ser Pro Ser Ala Asp Gln Arg Ala Gln Asp Arg Glu Glu Glu
                165                 170                 175

Ala Thr Ala Ala Pro Val Pro Thr Ser Ser Gly His Arg Thr Glu Lys
            180                 185                 190

Arg Lys Arg Leu Gln Leu Gln Cys Gln Pro Ala Gly Gly Thr Gly Gln
        195                 200                 205

Arg Arg Gly Ser Arg Ser Ser Pro Ser Ala Asp Gln Gln Arg Ala Gln
    210                 215                 220

Asp Arg Glu Glu Glu Ala Ala Ala Pro Ala Pro Thr Ser Arg Gly
225                 230                 235                 240

His Arg Thr Glu Lys Arg Lys Pro Gln Gln Pro Gln Arg Arg Pro Ala
                245                 250                 255
```

Ala Gly Thr Gly Gln Arg Arg Gly Ser Gly Cys Ser Pro Ser Ala Asp
            260                 265                 270

Gln Gln Gly Ala Gln Asp Arg Glu Glu Ala Ala Ala Pro Ala
        275                 280                 285

Pro Thr Ser Arg Gly His Arg Thr Glu Lys Lys Arg Leu Gln Pro
        290                 295                 300

Gln Arg Arg Pro Ala Gly Gly Thr Gly Gln Arg Arg Gly Ser Arg Ser
305                 310                 315                 320

Ser Pro Ser Ala Asp Gln Gln Arg Ala Gln Asp Arg Glu Glu Ala
                325                 330                 335

Ala Ala Ala Pro Val Pro Thr Ser Arg Gly His Arg Thr Glu Lys Arg
                340                 345                 350

Lys Arg Leu Gln Leu Gln Cys Gln Pro Ala Gly Gly Thr Gly Gln Arg
        355                 360                 365

Arg Gly Ser Gly Ser Ser Pro Ser Ala Asp Gln Arg Ala Gln Asp
        370                 375                 380

Arg Glu Glu Glu Ala Ala Ala Pro Ala Pro Thr Ser Ser Gly His
385                 390                 395                 400

Arg Thr Glu Lys Arg Lys Arg Gln Gln Pro Arg Arg Pro Ala Ala
                405                 410                 415

Gly Thr Gly Gln Arg Arg Gly Ser Glu Glu Met Glu Glu Glu Gly
                420                 425                 430

<210> SEQ ID NO 2
<211> LENGTH: 971
<212> TYPE: DNA
<213> ORGANISM: Artificial
<220> FEATURE:
<223> OTHER INFORMATION: Synthetic

<400> SEQUENCE: 2
attttgttta ctttaagaag gagatataca tatgcggggt tctcatcatc atcatcatca     60
tggtatggct agcatgactg gtggacagca aatgggtcgg gatctgtacg acgatgacga    120
taaggatcga tggggatccc ccgggctgca ggaattcggc acgagagaag aggaagccgc    180
agcagcccca gcgccgacca gcaggggggca caggacagag aagaggaagc ggctacagcc    240
ccagcgccga ccagcagggg gcacaggaca gagaagagga agccgcagca gccccagcgc    300
cgaccagcag cgggcacagg acagagaaga ggaagcggct gcagctccag tgccaaccag    360 caggggggcac aggacagaga agaggaagcg gctgcagctc cagtgccaac agcaggggg    420 cacaggacag agaagaggaa gcggcagcag ccccagtgcc gaccagcagc gggcacagga    480
cagagaagag gaagccgcag cagccccagc gccgaccagc agcgggcaca ggacagagaa    540
gaggaagcgg cagcagcccc agcgccgacc agcagcgggc acaggacaga agaggaag    600 tgaggaaatg gaagaagagg gttgacctga gctgaaggac atgaacttcc acgtgaaata    660
gccccagggc cgggcacacg aggtcaggag ttcaagacca gcctggccaa gatggtgaaa    720
ccctgtctct actaaaaata aaaaattagc tgggtgcggt ggcaggcacc tgtaatccca    780
gctactcagg aggctgaggc aggagaatca cttgaaccca ggaggtggag gttacagtga    840
gccaagatct caccactgca ctgtagcctg gcaacagag caagactcca tgaaaaaaaa    900
aaaaaaaaac tcgagggggg gcccggtacc atggaattcg aagcttgatc cggctgctaa    960
caaagcccga a                                                        971

<210> SEQ ID NO 3
<211> LENGTH: 197
<212> TYPE: PRT
<213> ORGANISM: Artificial
<220> FEATURE:
<223> OTHER INFORMATION: Synthetic

<400> SEQUENCE: 3

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Pro Gly Leu Gln Glu Phe Gly Thr Arg Glu Glu
        35                  40                  45

Ala Ala Ala Ala Pro Ala Pro Thr Ser Arg Gly His Arg Thr Glu Lys
    50                  55                  60

Arg Lys Arg Leu Gln Pro Gln Arg Pro Ala Gly Gly Thr Gly Gln
65              70                  75                  80

Arg Arg Gly Ser Arg Ser Ser Pro Ser Ala Asp Gln Gln Arg Ala Gln
                85                  90                  95

Asp Arg Glu Glu Glu Ala Ala Ala Pro Val Pro Thr Ser Arg Gly
                100                 105                 110

His Arg Thr Glu Lys Arg Lys Arg Leu Gln Leu Gln Cys Gln Pro Ala
            115                 120                 125

Gly Gly Thr Gly Gln Arg Arg Gly Ser Gly Ser Ser Pro Ser Ala Asp
    130                 135                 140

Gln Gln Arg Ala Gln Asp Arg Glu Glu Glu Ala Ala Ala Pro Ala
145                 150                 155                 160

Pro Thr Ser Ser Gly His Arg Thr Glu Lys Arg Lys Arg Gln Gln Pro
                165                 170                 175

Gln Arg Arg Pro Ala Ala Gly Thr Gly Gln Arg Arg Gly Ser Glu Glu
                180                 185                 190

Met Glu Glu Glu Gly
        195
```

<210> SEQ ID NO 4
<211> LENGTH: 153
<212> TYPE: PRT
<213> ORGANISM: Artificial
<220> FEATURE:
<223> OTHER INFORMATION: Synthetic

<400> SEQUENCE: 4

```
Arg Glu Glu Glu Ala Ala Ala Ala Pro Ala Pro Thr Ser Arg Gly His
1               5                   10                  15

Arg Thr Glu Lys Arg Lys Arg Leu Gln Pro Gln Arg Arg Pro Ala Gly
            20                  25                  30

Gly Thr Gly Gln Arg Arg Gly Ser Arg Ser Ser Pro Ser Ala Asp Gln
        35                  40                  45

Gln Arg Ala Gln Asp Arg Glu Glu Glu Ala Ala Ala Pro Val Pro
    50                  55                  60

Thr Ser Arg Gly His Arg Thr Glu Lys Arg Lys Arg Leu Gln Leu Gln
65              70                  75                  80

Cys Gln Pro Ala Gly Gly Thr Gly Gln Arg Arg Gly Ser Gly Ser Ser
                85                  90                  95

Pro Ser Ala Asp Gln Gln Arg Ala Gln Asp Arg Glu Glu Glu Ala Ala
            100                 105                 110
```

Ala Ala Pro Ala Pro Thr Ser Ser Gly His Arg Thr Glu Lys Arg Lys
            115                 120                 125

Arg Gln Gln Pro Gln Arg Arg Pro Ala Ala Gly Thr Gly Gln Arg Arg
        130                 135                 140

Gly Ser Glu Glu Met Glu Glu Gly
145                 150

<210> SEQ ID NO 5
<211> LENGTH: 35
<212> TYPE: PRT
<213> ORGANISM: Artificial
<220> FEATURE:
<223> OTHER INFORMATION: Synthetic

<400> SEQUENCE: 5

Ser Ser Gly His Arg Thr Glu Lys Arg Lys Arg Gln Gln Pro Gln Arg
1               5                   10                  15

Arg Pro Ala Ala Gly Thr Gly Gln Arg Arg Gly Ser Glu Glu Met Glu
            20                  25                  30

Glu Glu Gly
        35

<210> SEQ ID NO 6
<211> LENGTH: 29
<212> TYPE: PRT
<213> ORGANISM: Artificial
<220> FEATURE:
<223> OTHER INFORMATION: Synthetic

<400> SEQUENCE: 6

Glu Lys Arg Lys Arg Gln Gln Pro Gln Arg Arg Pro Ala Ala Gly Thr
1               5                   10                  15

Gly Gln Arg Arg Gly Ser Glu Glu Met Glu Glu Glu Gly
            20                  25

<210> SEQ ID NO 7
<211> LENGTH: 123
<212> TYPE: PRT
<213> ORGANISM: Artificial
<220> FEATURE:
<223> OTHER INFORMATION: Synthetic

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Thr Gly Phe
            20                  25                  30

Tyr Ile His Trp Met Lys Gln Ser His Val Lys Ser Leu Glu Trp Ile
        35                  40                  45

Gly Arg Ile His Pro Tyr Asn Gly Ala Thr Ser Tyr Asn Gln Asn Phe
    50                  55                  60

Lys Asp Arg Ala Ser Leu Thr Val Asp Glu Ser Ser Thr Ala Tyr
65                  70                  75                  80

Met Glu Phe Tyr Gly Leu Thr Ser Glu Asp Ser Ala Val Tyr Tyr Cys
                85                  90                  95

Ala Arg Glu Arg Val Tyr Tyr Tyr Gly Ser Thr Tyr Glu Phe Asp Ser
            100                 105                 110

Trp Gly Gln Gly Thr Thr Leu Thr Val Ser Ser
        115                 120

```
<210> SEQ ID NO 8
<211> LENGTH: 123
<212> TYPE: PRT
<213> ORGANISM: Artificial
<220> FEATURE:
<223> OTHER INFORMATION: Synthetic

<400> SEQUENCE: 8

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Phe
            20                  25                  30

Tyr Ile His Trp Val Lys Gln Ser His Val Lys Ser Leu Glu Trp Ile
        35                  40                  45

Gly Arg Ile His Pro Tyr Asn Gly Ala Pro Thr Tyr Asn Gln Asn Phe
    50                  55                  60

Lys Asp Arg Ala Arg Leu Thr Val His Glu Ser Ser Ser Thr Ala Tyr
65                  70                  75                  80

Met Glu Phe Phe Gly Leu Thr Ser Glu Asp Ser Ala Val Tyr Tyr Cys
                85                  90                  95

Ala Arg Glu Arg Val Tyr Tyr Tyr Gly Ser Thr Tyr Glu Phe Asp Phe
            100                 105                 110

Trp Gly Gln Gly Thr Thr Leu Thr Val Ser Ser
        115                 120

<210> SEQ ID NO 9
<211> LENGTH: 122
<212> TYPE: PRT
<213> ORGANISM: Artificial
<220> FEATURE:
<223> OTHER INFORMATION: Synthetic

<400> SEQUENCE: 9

Asp Val Lys Leu Gln Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Ile Asn Tyr Ala Glu
    50                  55                  60

Ser Val Lys Gly Arg Phe Thr Ile Ser Arg Asp Asp Ser Lys Ser Ser
65                  70                  75                  80

Val Tyr Leu Asp Met Asn Asn Leu Arg Ala Glu Asp Thr Gly Ile Tyr
                85                  90                  95

Tyr Cys Thr Ser Tyr Tyr Gly Ser Ser Leu Tyr Tyr Leu Asp Tyr Trp
            100                 105                 110

Gly Gln Gly Thr Thr Leu Thr Val Ser Ser
        115                 120

<210> SEQ ID NO 10
<211> LENGTH: 112
<212> TYPE: PRT
<213> ORGANISM: Artificial
<220> FEATURE:
<223> OTHER INFORMATION: Synthetic
```

<400> SEQUENCE: 10

Asp Val Leu Met Thr Gln Thr Pro Leu Ser Leu Pro Val Ser Leu Gly
1               5                   10                  15

Asp Gln Ala Ser Ile Ser Cys Arg Ser Gly Gln Ser Ile Val His
            20                  25                  30

Ser Gly Val Thr Tyr Leu Ser Trp Tyr Leu Gln Lys Pro Gly Gln Ser
            35                  40                  45

Pro Lys Leu Leu Ile Tyr Lys Val Phe Tyr Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ser Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

<210> SEQ ID NO 11
<211> LENGTH: 112
<212> TYPE: PRT
<213> ORGANISM: Artificial
<220> FEATURE:
<223> OTHER INFORMATION: Synthetic

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Gly Gln Ser Ile Val His Ser
            20                  25                  30

Ser Gly Val Thr Tyr Leu Ser Trp Tyr Leu Gln Lys Pro Gly Gln Ser
            35                  40                  45

Pro Lys Leu Leu Ile Tyr Lys Val Phe Tyr Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Thr Gly Thr Lys Leu Glu Leu Lys
            100                 105                 110

<210> SEQ ID NO 12
<211> LENGTH: 106
<212> TYPE: PRT
<213> ORGANISM: Artificial
<220> FEATURE:
<223> OTHER INFORMATION: Synthetic

<400> SEQUENCE: 12

Gln Ile Val Leu Thr Gln Ser Pro Val Ile Met Ser Ala Ser Pro Gly
1               5                   10                  15

Glu Lys Val Thr Ile Ser Cys Ser Ala Ser Ser Ser Val Ser Asn Met
            20                  25                  30

Tyr Trp Tyr Gln Gln Lys Pro Gly Ser Ser Pro Lys Ala Trp Ile Tyr
            35                  40                  45

Arg Thr Ser Asn Leu Ala Ser Gly Val Pro Ala Arg Phe Ser Gly Ser
        50                  55                  60

```
Gly Ser Gly Thr Ser Tyr Ser Leu Thr Ile Ser Ser Met Glu Ala Glu
 65                  70                  75                  80

Asp Ala Ala Thr Tyr Tyr Cys His Gln Tyr Gln Ser Tyr Pro Arg Thr
                 85                  90                  95

Phe Gly Ala Gly Thr Lys Leu Glu Ile Lys
            100                 105

<210> SEQ ID NO 13
<211> LENGTH: 5
<212> TYPE: PRT
<213> ORGANISM: Artificial
<220> FEATURE:
<223> OTHER INFORMATION: Synthetic

<400> SEQUENCE: 13

Gly Phe Tyr Ile His
1               5

<210> SEQ ID NO 14
<211> LENGTH: 17
<212> TYPE: PRT
<213> ORGANISM: Artificial
<220> FEATURE:
<223> OTHER INFORMATION: Synthetic

<400> SEQUENCE: 14

Arg Ile His Pro Tyr Asn Gly Ala Thr Ser Tyr Asn Gln Asn Phe Lys
1               5                   10                  15

Asp

<210> SEQ ID NO 15
<211> LENGTH: 14
<212> TYPE: PRT
<213> ORGANISM: Artificial
<220> FEATURE:
<223> OTHER INFORMATION: Synthetic

<400> SEQUENCE: 15

Glu Arg Val Tyr Tyr Tyr Gly Ser Thr Tyr Glu Phe Asp Ser
1               5                   10

<210> SEQ ID NO 16
<211> LENGTH: 17
<212> TYPE: PRT
<213> ORGANISM: Artificial
<220> FEATURE:
<223> OTHER INFORMATION: Synthetic

<400> SEQUENCE: 16

Arg Ile His Pro Tyr Asn Gly Ala Pro Thr Tyr Asn Gln Asn Phe Lys
1               5                   10                  15

Asp

<210> SEQ ID NO 17
<211> LENGTH: 5
<212> TYPE: PRT
<213> ORGANISM: Artificial
<220> FEATURE:
<223> OTHER INFORMATION: Synthetic

<400> SEQUENCE: 17

Asn Tyr Trp Met Asn
1               5
```

```
<210> SEQ ID NO 18
<211> LENGTH: 19
<212> TYPE: PRT
<213> ORGANISM: Artificial
<220> FEATURE:
<223> OTHER INFORMATION: Synthetic

<400> SEQUENCE: 18

Glu Ile Arg Leu Lys Ser Asn Asn Tyr Ala Ile Asn Tyr Ala Glu Ser
1               5                   10                  15

Val Lys Gly

<210> SEQ ID NO 19
<211> LENGTH: 11
<212> TYPE: PRT
<213> ORGANISM: Artificial
<220> FEATURE:
<223> OTHER INFORMATION: Synthetic

<400> SEQUENCE: 19

Tyr Tyr Gly Ser Ser Leu Tyr Tyr Leu Asp Tyr
1               5                   10

<210> SEQ ID NO 20
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Wherein Xaa at position 9 is T or P
<220> FEATURE:
<221> NAME/KEY: MISC_FEATURE
<222> LOCATION: (10)..(10)
<223> OTHER INFORMATION: Wherein Xaa at position 10 is S or T

<400> SEQUENCE: 20

Arg Ile His Pro Tyr Asn Gly Ala Xaa Xaa Tyr Asn Gln Asn Phe Lys
1               5                   10                  15

Asp

<210> SEQ ID NO 21
<211> LENGTH: 16
<212> TYPE: PRT
<213> ORGANISM: Artificial
<220> FEATURE:
<223> OTHER INFORMATION: Synthetic

<400> SEQUENCE: 21

Arg Ser Gly Gln Ser Ile Val His Thr Ser Gly Val Thr Tyr Leu Ser
1               5                   10                  15

<210> SEQ ID NO 22
<211> LENGTH: 7
<212> TYPE: PRT
<213> ORGANISM: Artificial
<220> FEATURE:
<223> OTHER INFORMATION: Synthetic

<400> SEQUENCE: 22

Lys Val Phe Tyr Arg Phe Ser
1               5
```

```
<210> SEQ ID NO 23
<211> LENGTH: 9
<212> TYPE: PRT
<213> ORGANISM: Artificial
<220> FEATURE:
<223> OTHER INFORMATION: Synthetic

<400> SEQUENCE: 23

Phe Gln Gly Ser His Val Pro Pro Thr
1               5

<210> SEQ ID NO 24
<211> LENGTH: 16
<212> TYPE: PRT
<213> ORGANISM: Artificial
<220> FEATURE:
<223> OTHER INFORMATION: Synthetic

<400> SEQUENCE: 24

Arg Ser Gly Gln Ser Ile Val His Ser Ser Gly Val Thr Tyr Leu Ser
1               5                   10                  15

<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Ser Ala Ser Ser Ser Val Ser Asn Met Tyr
1               5                   10

<210> SEQ ID NO 26
<211> LENGTH: 7
<212> TYPE: PRT
<213> ORGANISM: Artificial
<220> FEATURE:
<223> OTHER INFORMATION: Synthetic

<400> SEQUENCE: 26

Arg Thr Ser Asn Leu Ala Ser
1               5

<210> SEQ ID NO 27
<211> LENGTH: 9
<212> TYPE: PRT
<213> ORGANISM: Artificial
<220> FEATURE:
<223> OTHER INFORMATION: Synthetic

<400> SEQUENCE: 27

His Gln Tyr Gln Ser Tyr Pro Arg Thr
1               5

<210> SEQ ID NO 28
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Wherein Xaa at position 9 is T or S
```

<400> SEQUENCE: 28

Arg Ser Gly Gln Ser Ile Val His Xaa Ser Gly Val Thr Tyr Leu Ser
1               5                   10                  15

<210> SEQ ID NO 29
<211> LENGTH: 370
<212> TYPE: DNA
<213> ORGANISM: Artificial
<220> FEATURE:
<223> OTHER INFORMATION: Synthetic

<400> SEQUENCE: 29

```
gaggtccagc tgcaacagtc tggacctgag ctggtgaagc ctggggcttc agtgaagata      60
tcctgcaagg cttctggtta cgcattcact ggcttctaca tacactggat gaagcaaagc     120
catgtaaaga gccttgagtg gattggacgt attcatcctt acaatggtgc tactagctat     180
aatcagaatt tcaaggacag gccagcttg actgtagatg agtcctccag tacagcctac     240
atggagttct atggcctgac atctgaggac tctgcagtct attactgtgc aagagagaga     300
gtctattact acggtagtac ttacgagttt gactcctggg gccaaggcac cactctcaca     360
gtctcctcag                                                            370
```

<210> SEQ ID NO 30
<211> LENGTH: 370
<212> TYPE: DNA
<213> ORGANISM: Artificial
<220> FEATURE:
<223> OTHER INFORMATION: Synthetic

<400> SEQUENCE: 30

```
gaggtccagc tgcaacaatc tggacctgag ctggtgaagc ctggggcttc agtgaagata      60
tcctgcaagg cttctggtta ctcattcact ggcttctaca tacactgggt gaagcaaagc     120
catgtaaaga gccttgagtg gattggacgt attcatcctt acaatggtgc tcctacctac     180
aaccagaatt tcaaggacag ggcccgcttg actgtacatg agtcctccag cacagcctac     240
atggagttct ttggcctgac atctgaggac tctgcagtct attactgtgc aagagagaga     300
gtctattact acggtagtac ttacgagttt gacttctggg gccaaggcac cactctcaca     360
gtctcctcag                                                            370
```

<210> SEQ ID NO 31
<211> LENGTH: 367
<212> TYPE: DNA
<213> ORGANISM: Artificial
<220> FEATURE:
<223> OTHER INFORMATION: Synthetic

<400> SEQUENCE: 31

```
gatgtgaagc ttcaggagtc tggaggaggc ttggtgcaac tggaggatc catgaaactc       60
tcctgtgttg cctctggatt cactttcagt aactactgga tgaactgggt ccgccagtct     120
ccagagaagg gcttgagtg ggttgctgaa attagattga aatctaataa ttatgcaata     180
aattatgcgg agtctgtgaa agggaggttt accatctcaa gagatgattc caaaagcagt     240
gtctacctgg acatgaacaa cttaagagct gaagacactg gcatttatta ctgtacctcc     300
tactacggca gtagcctcta ctaccttgac tactggggcc aaggcaccac tctcacagtc     360
tcctcag                                                               367
```

```
<210> SEQ ID NO 32
<211> LENGTH: 337
<212> TYPE: DNA
<213> ORGANISM: Artificial
<220> FEATURE:
<223> OTHER INFORMATION: Synthetic

<400> SEQUENCE: 32
gatgttttga tgacccaaac tccactctcc ctgcctgtca gtcttggaga tcaagcctcc      60
atctcttgca gatctggtca gagcattgtc catactagtg gcgtcaccta tttatcatgg     120
tacctgcaga aaccaggcca gtctccaaag ctcctgatct acaaagtttt ctaccgattt     180
tctggggtcc cggacaggtt cagtggcagt ggatcaggga cagatttcac actcaagatc     240
agcagagtgg agtctgagga tctgggagtt tattactgct ttcaaggttc acatgttcct     300
cccacgttcg gtgctgggac caagctggag ctgaaac                              337

<210> SEQ ID NO 33
<211> LENGTH: 337
<212> TYPE: DNA
<213> ORGANISM: Artificial
<220> FEATURE:
<223> OTHER INFORMATION: Synthetic

<400> SEQUENCE: 33
gatgttttga tgacccaaac tccactctcc ctgcctgtca gtcttggaga tcaagcctcc      60
atctcttgca gatctggtca gagcattgtc catagtagtg gcgtcaccta tttatcatgg     120
tacctgcaga aaccaggcca gtctccaaag ctcctgatct acaaagtttt ctaccgattt     180
tctggggtcc cggacaggtt cagtggcagt ggatcaggga cagatttcac actcaagatc     240
agcagagtgg aggctgagga tctgggagtt tattactgct ttcagggttc acatgttcct     300
cccacgttcg gtactgggac caagctggag ctgaaac                              337

<210> SEQ ID NO 34
<211> LENGTH: 319
<212> TYPE: DNA
<213> ORGANISM: Artificial
<220> FEATURE:
<223> OTHER INFORMATION: Synthetic

<400> SEQUENCE: 34
caaattgttc tcacccagtc tccagtaatc atgtctgcat ctccagggga gaaggtcacc      60
atatcctgca gtgccagctc aagtgtaagt aacatgtact ggtaccagca gaagccagga     120 tcctcccccaa aagcctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccaccagtat caaagttacc cacggacgtt cggtgcaggc     300
accaagctgg aaatcaaac                                                  319

<210> SEQ ID NO 35
<211> LENGTH: 14
<212> TYPE: PRT
<213> ORGANISM: Artificial
<220> FEATURE:
<223> OTHER INFORMATION: Synthetic

<400> SEQUENCE: 35

Glu Arg Val Tyr Tyr Tyr Gly Ser Thr Tyr Glu Phe Asp Phe
1               5                   10
```

```
<210> SEQ ID NO 36
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Wherein Xaa at position 14 is S or F

<400> SEQUENCE: 36

Glu Arg Val Tyr Tyr Tyr Gly Ser Thr Tyr Glu Phe Asp Xaa
1               5                   10
```

MONOCLONAL ANTIBODIES, COMPOSITIONS AND METHODS FOR DETECTING MUCIN-LIKE PROTEIN (MLP) AS A BIOMARKER FOR OVARIAN AND PANCREATIC CANCER

CROSS-REFERENCE TO RELATED APPLICATION

This application claims the benefit under 35 U.S.C. § 119(e) of U.S. Provisional Patent Application No. 62/347,824, filed Jun. 9, 2016; which application is incorporated herein by reference in its entirety.

FIELD OF THE INVENTION

The present invention relates to monoclonal antibodies and compositions comprising such antibodies for use in detecting ovarian and pancreatic cancer.

STATEMENT REGARDING SEQUENCE LISTING

The sequence listing associated with this application is provided in text format in lieu of a paper copy and is hereby incorporated by reference into the specification. The name of the text file containing the sequence listing is AB.1.0208.US2.Sequence Listing.20170525_ST25. The text file is 24 KB, was created on May 25, 2017; and is being submitted via EFS-Web with the filing of the specification.

BACKGROUND

Amongst female cancer patients there is a high incidence of ovarian cancer and this is associated with high mortality (Modugno et al., *Am J of Obstetrics and Gynecology* 191: 733-740, 2004). It is the fifth most common cancer in women, following breast, bowel, lung and uterine cancers. It is called a silent killer because it is asymptomatic until it reaches the late stages (Chauhan et al., *J of Ovarian Research* 2:2215, 2009). Early diagnosis of ovarian cancer is difficult because the first symptoms are non-localized mild pain, but the symptoms of ovarian malignancies become clearer in the late stages, and include loss of appetite and weight, strong pain in the back and pelvis associated with vaginal bleeding after menopause, frequent urination, constipation or diarrhea and bloating in the abdomen (American Cancer Society, 2013).

The early detection of ovarian malignancies represents a so far unmet need. The presently used tumor associated biomarkers, for example the relatively unspecific tumor marker CA-125, all fail to detect ovarian malignancies at an early stage.

Therefore, there is a pressing need to develop a non-invasive clinical test for early diagnosis to discover ovarian malignancies at an early stage when treatment is effective and the prognosis much better then in later stages of ovarian cancer.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides an isolated antibody, or antigen binding fragment thereof, that specifically binds to an epitope in the C-terminal region of human mucin-like protein, set forth as SEQ ID NO:4. In one embodiment, the antibody is a monoclonal antibody. In one embodiment, said antibody is a humanized, chimeric or fully human antibody. In one embodiment, said antibody or antigen binding fragment thereof is capable of binding to glycosylated human MLP secreted from an epithelial cancer cell line. In one embodiment, said antibody or antigen binding fragment thereof is capable of binding to glycosylated human MLP in an ELISA assay format. In one embodiment, said antibody or antigen binding fragment thereof binds to human MLP with a $K_D$ of less than 10 nM, such as less than 1 nM. In one embodiment, said antibody, or antigen binding fragment thereof recognizes at least part of an epitope recognized by one or more reference antibodies selected from the group consisting of:

(i) the monoclonal antibody MLP Clone 11 produced by the hybridoma cell line deposited at the ATCC on Oct. 30, 2014 under the ATCC Designation Number PTA-121699.

(ii) the monoclonal antibody MLP Clone B produced by the hybridoma cell line deposited at the ATCC on Oct. 30, 2014 under the ATCC Designation Number PTA-121700; and (iii) the monoclonal antibody MLP Clone C produced by the hybridoma cell line deposited at the ATCC on Oct. 30, 2014 under the ATCC Designation Number PTA-121701.

In one embodiment, said antibody comprises a variable region of the heavy chain comprising or consisting of a sequence which is at least 90% identical to an amino acid sequence selected from the group consisting of SEQ ID NO:7, SEQ ID NO:8 and SEQ ID NO:9. In one embodiment, said antibody comprises a variable region of the light chain comprising or consisting of a sequence which is at least 90% identical to an amino acid sequence selected from the group consisting of SEQ ID NO:10, SEQ ID NO:11 and SEQ ID NO:12. In one embodiment, said antibody is labeled with a detectable moiety. In one embodiment, said antibody is coupled to a therapeutic agent. In one embodiment, said antibody is immobilized on a substrate.

In another aspect, the invention provides an antibody, or antigen binding fragment thereof, that binds to the C-terminal region of mucin-like protein (MLP), comprising: (i) a heavy chain variable region comprising CDR-H1, CDR-H2 and CDR-H3 sequences; and (ii) a light chain variable region comprising CDR-L1, CDR-L2 and CDR-L3, wherein the heavy chain variable region CDR-H3 sequence comprises an amino acid sequence set forth as SEQ ID NO:15, SEQ ID NO:35, SEQ ID NO:36 or SEQ ID NO:19, and conservative sequence modifications thereof, wherein the light chain variable region CDR-L3 sequence comprises an amino acid sequence set forth as SEQ ID NO:23 or SEQ ID NO:27, and conservative sequence modifications thereof. In one embodiment, said antibody, or antigen binding fragment thereof, comprises (i) a heavy chain variable region comprising CDR-H1 (SEQ ID NO:13), CDR-H2 (SEQ ID NO:14) and CDR-H3 (SEQ ID NO:15 or SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof. In one embodiment, said antibody or antigen binding fragment thereof comprises (i) a heavy chain variable region comprising CDR-H1 (SEQ ID NO:13), CDR-H2 (SEQ ID NO:16) and CDR-H3 (SEQ ID NO:15, SEQ ID NO:35, or SEQ ID NO:36) and (ii) a light chain variable region comprising CDR-L1 (SEQ ID NO:24), CDR-L2 (SEQ ID NO:22) and CDR-L3 (SEQ ID NO:23), and conservative modifications thereof. In one embodiment, said antibody, or antigen binding fragment thereof comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

In another aspect, the invention provides an isolated polypeptide comprising the amino acid sequence of SEQ ID NO:1, or a variant thereof having at least 95% identity to SEQ ID NO:1.

In another aspect, the invention provides an isolated polypeptide comprising the amino acid sequence of SEQ ID NO:4, or a variant thereof having at least 95% identity to SEQ ID NO:4.

In another aspect, the invention provides an isolated polypeptide comprising the amino acid sequence of SEQ ID NO:5, or a variant thereof having at least 95% identity to SEQ ID NO:5.

In another aspect, the invention provides an isolated polypeptide comprising the amino acid sequence of SEQ ID NO:6, or a variant thereof having at least 95% identity to SEQ ID NO:6.

In another aspect, the invention provides a method of detecting or diagnosing epithelial cancer by determining the presence or amount of MLP in a biological sample from a test subject. The method comprises (a) contacting a biological sample from a test subject with an anti-MLP antibody or antigen-binding fragment thereof in an in vitro immunoassay; and (b) detecting the presence or absence of binding of said antibody, wherein the detection of binding indicates the presence or amount of MLP in the sample, wherein the antibody or fragment thereof binds to an epitope in the C-terminal region of MLP, set forth as SEQ ID NO:4, such as an epitope in SEQ ID NO:5 or SEQ ID NO:6. In some embodiments, said anti-MLP antibody is labeled with a detectable moiety and step (b) comprises detecting the presence or amount of said detectable moiety. In some embodiments, the method further comprises the step of comparing the amount of MLP detected in accordance with step (b) with a reference standard or control sample from a healthy subject, wherein an increase of at least two-fold or higher in the level of MLP in the test sample as compared to the control sample or reference standard indicates the presence of, or increased risk for developing an epithelial cancer, such as ovarian cancer or pancreatic cancer, in the test subject. In some embodiments, the biological sample is selected from the group consisting of blood, serum, plasma and tissue.

In another aspect, the invention provides a method of detecting or diagnosing a mucin-secreting type of cancer, such as a mucin-secreting cancer selected from the group consisting of ovarian, pancreatic, colorectal, breast, appendiceal, lung, renal, cervical, biliary, esophageal, epithelial skin and/or other mucin-secreting types of cancer in a test subject by determining the presence or amount of MLP comprising (a) administering to a living test subject a humanized or fully human anti-MLP antibody or antigen-binding fragment thereof that binds to an epitope in the C-terminal region of MLP, set forth as SEQ ID NO:4, such as an epitope in SEQ ID NO:5 or SEQ ID NO:6; and (b) detecting the presence or absence or the amount of the antibody or fragment thereof bound to MLP, wherein detection of the presence or amount of MLP in the subject indicates the presence of ovarian, pancreatic, colorectal, breast, appendiceal, lung, renal, cervical, biliary, esophageal, epithelial skin and/or other mucin-secreting types of cancer in the test subject. In one embodiment, the anti-MLP antibody is labeled with a detectable moiety suitable for in vivo use and step (b) comprises detecting the presence or amount of the detectable moiety. In one embodiment, the method is used in an imaging, intraoperative, endoscopic or intravascular procedure.

In another aspect, the invention provides a method of treating a subject suffering from a mucin-secreting type of cancer, such as a mucin-secreting cancer selected from the group consisting of ovarian, pancreatic, colorectal, breast, appendiceal, lung, renal, cervical, biliary, esophageal, epithelial skin and/or other mucin-secreting types of cancer comprising administering to an individual suffering from a mucin-secreting type of cancer a humanized or fully human anti-MLP antibody or antigen-binding fragment thereof that binds to an epitope in the C-terminal region of MLP, set forth as SEQ ID NO:4, such as an epitope in SEQ ID NO:5 or SEQ ID NO:6, wherein the antibody or fragment thereof is coupled to a therapeutic agent.

In another aspect, the invention provides a kit for detecting the present or amount of MLP in a biological sample, the kit comprising (a) at least one container, and (b) at least one anti-MLP antibody that binds to an epitope in the C-terminal region of MLP, set forth as SEQ ID NO:4, such as an epitope in SEQ ID NO:5 or SEQ ID NO:6.

The anti-MLP antibodies, compositions and kits of the invention can be used to practice the methods of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 depicts the amino acid sequence of full-length human mucin-like protein (MLP) (SEQ ID NO:1), with the C-terminal region (aa 279-431) (SEQ ID NO:4) underlined;

FIG. 2 depicts the amino acid sequence of a recombinant fusion protein (SEQ ID NO:3) comprising an N-terminal histidine tag fused to residues 279-431 of the C-terminal region of human MLP, with the N-terminal vector-derived sequence underlined;

FIG. 10A depicts an amino acid sequence alignment between the variable heavy chain regions of anti-MLP monoclonal antibody clones 11 (SEQ ID NO:7), B (SEQ ID NO:8) and 2(C) (SEQ ID NO:9), as described in Example 3; and FIG. 10B depicts an amino acid sequence alignment between the variable light chain regions of anti-MLP monoclonal antibody clones 11 (SEQ ID NO:10), B (SEQ ID NO:11) and 2(C) (SEQ ID NO:12), as described in Example 3.

DESCRIPTION OF THE SEQUENCE LISTING

Figure 3A:
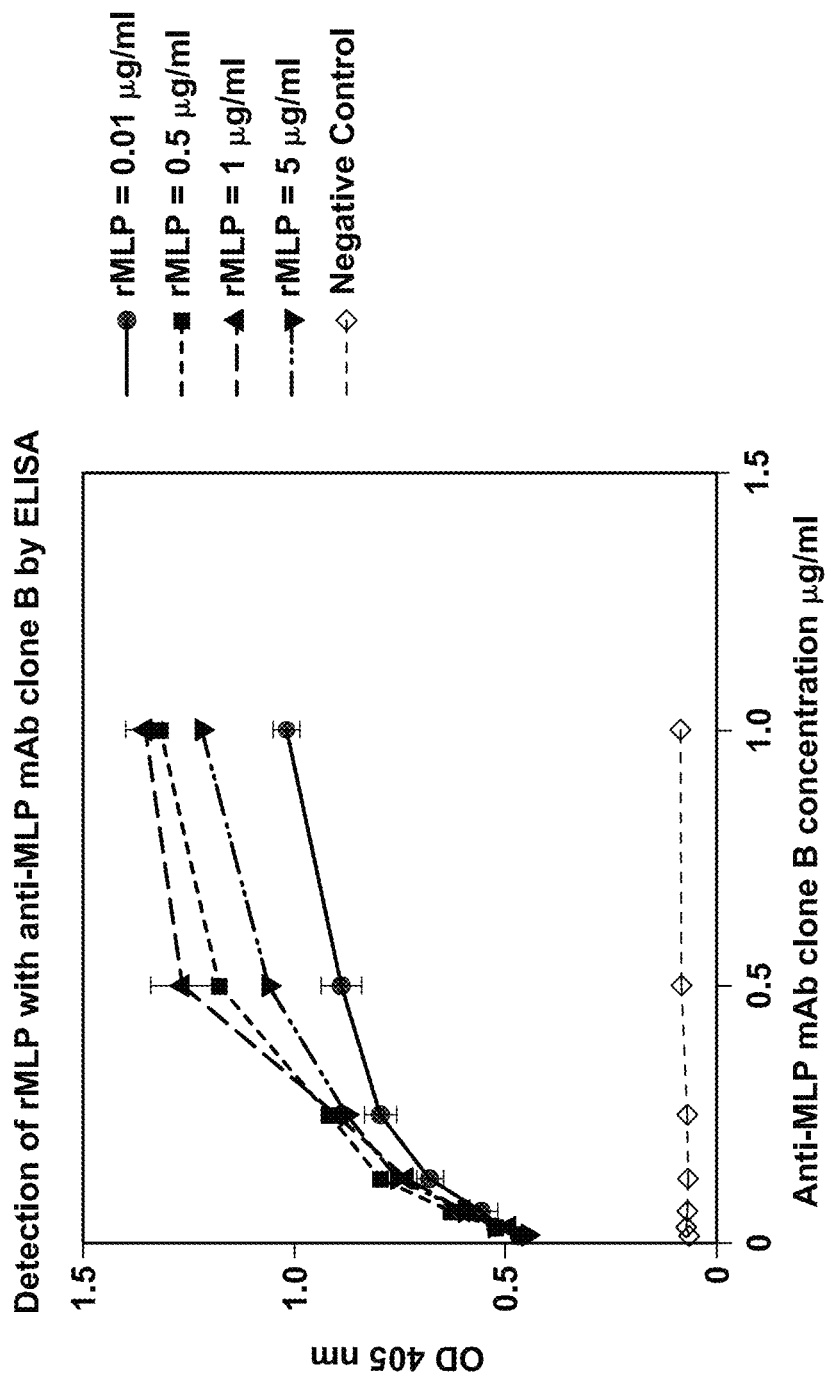
FIG. 3A graphically illustrates the results of an ELISA assay carried out with anti-MLP monoclonal antibody clone B tested against various concentrations of recombinant MLP (rMLP) C-terminal protein, as described in Example 1.

Antigens
SEQ ID NO:1: Amino acid sequence of the full length human mucin-like protein (MLP), 431 amino acids in length.
SEQ ID NO:2: DNA encoding a fusion protein comprising an N-terminal histidine tag and a polypeptide region corresponding to residues 279-431 of the C-terminal region of human MLP.
SEQ ID NO:3: amino acid sequence of the fusion protein (encoded by SEQ ID NO:2) comprising the N-terminal histidine detection tag fused to residues 279-431 of the C-terminal region of human MLP.
SEQ ID NO:4: amino acid sequence of the C-terminal region (aa 279-431) of human MLP.
SEQ ID NO:5: SSGHRTEKRKRQQPQRRPAAGTGQR-RGSEEMEEEG (amino acid residues 397-431 of human MLP).
SEQ ID NO:6: EKRKRQQPQRRPAAGTGQRRG-SEEMEEEG (amino acid residues 403-431 of human MLP).
Monoclonal Antibodies VH Chains
SEQ ID NO:7: mAb clone 11: VH amino acid sequence
SEQ ID NO:8: mAb clone B: VH amino acid sequence
SEQ ID NO:9: mAb clone C: VH amino acid sequence
Monoclonal Antibodies VL Chains
SEQ ID NO:10: mAb clone 11: VL amino acid sequence
SEQ ID NO:11: mAb clone B: VL amino acid sequence
SEQ ID NO:12: mAb clone C: VL amino acid sequence
Monoclonal Antibodies Heavy Chain CDRs
SEQ ID NO:13: CDR-H1 from Clone 11 and Clone B
SEQ ID NO:14: CDR-H2 from Clone 11
SEQ ID NO:15: CDR-H3 from Clone 11
SEQ ID NO:35: CDR-H3 from Clone B
SEQ ID NO:16: CDR-H2 from Clone B
SEQ ID NO:17: CDR-H1 from Clone C
SEQ ID NO:18: CDR-H2 from Clone C
SEQ ID NO:19: CDR-H3 from Clone C
SEQ ID NO:20: CDR-H2 consensus from Clone 11 and Clone B
SEQ ID NO:36: CDR-H3 consensus from Clone 11 and Clone B
Monoclonal Antibodies Light Chain CDRs
SEQ ID NO:21: CDR-L1 from Clone 11
SEQ ID NO:22: CDR-L2 from Clone 11 and Clone B
SEQ ID NO:23: CDR-L3 from Clone 11 and Clone B
SEQ ID NO:24: CDR-L1 from Clone B
SEQ ID NO:25: CDR-L1 from Clone C
SEQ ID NO:26: CDR-L2 from Clone C
SEQ ID NO:27: CDR-L3 from Clone C
SEQ ID NO:28: CDR-L1 consensus from Clone 11 and Clone B
DNA encoding VH
SEQ ID NO:29: DNA encoding VH from Clone 11
SEQ ID NO:30: DNA encoding VH from Clone B
SEQ ID NO:31: DNA encoding VH from Clone C
DNA encoding VL
SEQ ID NO:32: DNA encoding VL from Clone 11
SEQ ID NO:33: DNA encoding VL from Clone B
SEQ ID NO:34: DNA encoding VL from Clone C

DETAILED DESCRIPTION

As described in Examples 1-3, high-affinity monoclonal antibodies have been identified that specifically bind to the C-terminal region of mucin-like protein (MLP), set forth as SEQ ID NO:4, and are useful for early detection of ovarian cancer, pancreatic cancer and other mucin-secreting malignant neoplasms in patient serum samples. Accordingly, the present invention is directed to monoclonal antibodies that specifically bind to the C-terminal region of mucin-like protein (MLP) and the use of these antibodies in methods of detecting a mucin-secreting type of cancer, such as a mucin-secreting cancer selected from the group consisting of ovarian, pancreatic, colorectal, breast, appendiceal, lung, renal, cervical, biliary, esophageal, epithelial skin and/or other mucin-secreting types of cancer mucin-secreting cancer types.

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments), that specifically bind to human mucin-like protein (MLP), set forth as SEQ ID NO:1 or a portion thereof, such as the C-terminal region of MLP (e.g., a C-terminal region of MLP comprising or consisting of amino acid residues 279-431, set forth as SEQ ID NO:4; or a C-terminal region of MLP comprising or consisting of amino acid residues 397-431, set forth as SEQ ID NO:5; or a C-terminal region of MLP comprising or consisting of amino acid residues 403-431, set forth as SEQ ID NO:6). It is not intended that the term "antibody" be limited as regards to the source of the antibody or manner in which it is made (e.g., by hybridoma, phage selection, recombinant expression, transgenic animal, peptide synthesis, etc). Exemplary antibodies include polyclonal, monoclonal and recombinant antibodies; multispecific antibodies (e.g., bispecific antibodies); humanized antibodies; fully human antibodies, murine antibodies; chimeric, mouse-human, mouse-primate, primate-human monoclonal antibodies; and anti-idiotype antibodies, and may be any intact molecule or fragment thereof. As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

As used herein, the term "antigen-binding fragment" refers to a polypeptide fragment that contains at least one CDR of an immunoglobulin heavy and/or light chains that specifically binds to human MLP (SEQ ID NO:1) or a portion thereof, such as the C-terminal region of MLP (e.g., a region comprising or consisting of amino acids amino acid residues 279-431, set forth as SEQ ID NO:4; or a C-terminal region of MLP comprising or consisting of amino acid residues 397-431, set forth as SEQ ID NO:5; or a C-terminal region of MLP comprising or consisting of amino acid residues 403-431, set forth as SEQ ID NO:6). In this regard, an antigen-binding fragment of the herein described antibodies may comprise 1, 2, 3, 4, 5, or all 6 CDRs of a VH and VL sequence set forth herein from antibodies that bind MLP.

As used herein the term "anti-MLP monoclonal antibodies" refers to a homogenous antibody population, wherein the monoclonal antibody is comprised of amino acids that are involved in the selective binding of an epitope on MLP, such as an epitope in the C-terminal region of MLP (e.g., a region comprising or consisting of amino acids amino acid residues 279-431, set forth as SEQ ID NO:4; or a C-terminal region of MLP comprising or consisting of amino acid residues 397-431, set forth as SEQ ID NO:5; or a C-terminal region of MLP comprising or consisting of amino acid residues 403-431, set forth as SEQ ID NO:6). Anti-MLP monoclonal antibodies are highly specific for the MLP target antigen. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope.

As used herein, the modifier "monoclonal" indicates the character of the antibody as being obtained from a substantially homogenous population of antibodies, and is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody". Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions, e.g., gamma (of about 330 amino acids).

The basic four-chain antibody unit is a heterotetrameric glycoprotein composed of two identical light (L) chains and two identical heavy (H) chains. An IgM antibody consists of 5 of the basic heterotetramer units along with an additional polypeptide called the J chain, and therefore contains 10 antigen binding sites. Secreted IgA antibodies can polymerize to form polyvalent assemblages comprising 2-5 of the basic 4-chain units along with J chain. Each L chain is linked to an H chain by one covalent disulfide bond, while the two H chains are linked to each other by one or more by one or more disulfide bonds, depending on the H chain isotype. Each H and L chain also has regularly spaced intrachain disulfide bridges. The pairing of a VH and VL together forms a single antigen-binding site.

Each H chain has at the N-terminus, a variable domain (VH), followed by three constant domains (CH) for each of the α and γ chains, and four CH domains (CH) for μ and ε isotypes.

Each L chain has at the N-terminus, a variable domain (VL) followed by a constant domain (CL) at its other end. The VL is aligned with the VH and the CL is aligned with the first constant domain of the heavy chain (CH1). The L chain from any vertebrate species can be assigned to one of two clearly distinct types, called kappa (κ) and lambda (λ), based on the amino acid sequences of their constant domains (CL).

Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated alpha (α), delta (δ), epsilon (ε), gamma (γ) and mu (μ), respectively. The γ and α classes are further divided into subclasses on the basis of minor differences in CH sequence and function, for example, humans express the following subclasses: IgG1, IgG2, IgG3, IgG4, IgA1 and IgA2.

For the structure and properties of the different classes of antibodies, see, e.g., Basic and Clinical Immunology, 8th Edition, Daniel P. Stites, Abba I. Terr and Tristram G. Parslow (eds); Appleton and Lange, Norwalk, Conn., 1994, page 71 and Chapter 6.

The term "variable" refers to that fact that certain segments of the V domains differ extensively in sequence among antibodies. The V domain mediates antigen binding and defines specificity of a particular antibody for its particular antigen. However, the variability is not evenly distributed across the 110 amino acid span of the variable domains. Rather, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody dependent cellular cytotoxicity (ADCC).

As used herein, the term "hypervariable region" refers to the amino acid residues of an antibody that are responsible for antigen binding. The hypervariable region generally comprises amino acid residues from a "complementary determining region" or "CDR" (i.e., from around about residues 24-34 (L1), 50-56 (L2) and 89-97 (L3) in the light chain variable domain, and around about 31-35 (H1), 50-66 (H2) and 95-102 (H3) in the heavy chain variable domain when numbering in accordance with the Kabat numbering system as described in Kabat, et al., *Sequences of Proteins of Immunological Interest*, 5th Ed. Public Health Service, National Institutes of Health, Bethesda, Md. (1991)); and/or those residues from a "hypervariable loop" (i.e., residues 24-34 (L1), 50-56 (L2) and 89-97 (L3) in the light chain variable domain, and 26-32 (H1), 52-56 (H2) and 95-101 (H3) in the heavy chain variable domain when numbered in accordance with the Chothia numbering system, as described in Chothia and Lesk, *J. Mol. Biol.* 196:901-917 (1987)); and/or those residues from a "hypervariable loop"/ CDR (e.g., residues 27-38 (L1), 56-65 (L2) and 105-120 (L3) in the VL, and 27-38 (H1), 56-65 (H2), and 105-120 (H3) in the VH when numbered in accordance with the IMGT numbering system as described in Lefranc, J. P., et al., *Nucleic Acids Res* 27:209-212; Ruiz, M., et al., *Nucleic Acids Res* 28:219-221 (2000)).

As used herein, the term "antibody fragment" refers to a portion derived from or related to a full-length anti-MLP antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules, bispecific and multispecific antibodies formed from antibody fragments.

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g., prepared chemically or from hybrid hybridomas, or may be any of the bispecific antibody fragments mentioned above.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding. See Pluckthun in *The Pharmacology of Monoclonal Antibodies*, Vol. 113, Rosenburg and Moore eds., Springer-Verlag, New York, pp. 269-315 (1994). "Fv" is the minimum antibody fragment that contains a complete antigen-recognition and binding site. This fragment consists of a dimer of one heavy and one light chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

As used herein, the term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the affinity between a capture agent and analyte when they are specifically bound in a capture agent/analyte complex is characterized by a $K_D$ (dissociation constant) of less than about 100 nM, or less than about 50 nM, or less than about 25 nM, or less than about 10 nM, or less than about 5 nM, or less than about 1 nM.

As used herein, the term "variant" anti-MLP antibody refers to a molecule, which differs in amino acid sequence from a "parent" or reference antibody amino acid sequence by virtue of addition, deletion, and/or substitution of one or more amino acid residue(s) in the parent antibody sequence. In one embodiment, a variant anti-MLP antibody refers to a molecule which contains variable regions that are identical to the parent variable domains, except for a combined total of 1, 2, 3, 4, 5, 6, 7, 8 9 or 10 amino acid substitutions within the CDR regions of the heavy chain variable region, and/or up to a combined total of 1, 2, 3, 4, 5, 6, 7, 8, 9, or 10 amino acid substitutions with said CDR regions of the light chain variable region. In some embodiments, the amino acid substitutions are conservative sequence modifications.

As used herein, the term "parent antibody" refers to an antibody, which is encoded by an amino acid sequence used for the preparation of the variant. Preferably, the parent antibody has a human framework region and, if present, has human antibody constant region(s). For example, the parent antibody may be a humanized or fully human antibody.

As used herein, the term "isolated antibody" refers to an antibody that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "epitope" refers to the portion of an antigen to which a monoclonal antibody specifically binds. Epitopic determinants usually consist of chemically active surface groupings of molecules such as amino acids or sugar side chains and usually have specific three-dimensional structural characteristics, as well as specific charge characteristics. More specifically, the term "MLP epitope," and "C-terminal MLP epitope" as used herein refers to a portion of the corresponding polypeptide (SEQ ID NO:1 and/or SEQ ID NO:4 and/or SEQ ID NO:5 and/or SEQ ID NO:6) to which an antibody immunospecifically binds as determined by any method well known in the art, for example, by immunoassays. Antigenic epitopes need not necessarily be immunogenic. Such epitopes can be linear in nature or can be a discontinuous epitope. Thus, as used herein, the term "conformational epitope" refers to a discontinuous epitope formed by a spatial relationship between amino acids of an antigen other than an unbroken series of amino acids.

As used herein, "a mammalian subject" includes without limitation, humans, non-human primates, dogs, cats, horses, sheep, goats, cows, rabbits, pigs and rodents.

As used herein, a "therapeutic agent" refers to a compound, molecule or atom, currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient which is administered separately, concurrently or sequentially with an antibody moiety or conjugated to an antibody moiety, i.e., antibody or antibody fragment, or a subfragment, and is useful in the treatment of a subject suffering from a pathological condition. The therapeutic agent may also be a toxin, a chemotherapeutic or a radioisotope, wherein the therapeutic moiety is intended for the killing of a cancer cell.

As used herein, a "detectable label" in the context of an immunoconjugate refers to a portion of the immunoconjugate which is a moiety having a property rendering its presence detectable, for example a moiety detectable by spectroscopic, photochemical, biochemical, immunochemical, chemical and/or other physical means. A detectable moiety may be coupled either directly and/or indirectly to the anti-MLP antibodies and antigen binding fragments thereof of the present invention. For example, the immunoconjugate may comprise an anti-MLP antibody that is labeled with a radioactive isotope or enzymatic activity which permits detection in an immunoassay.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, an "isolated nucleic acid molecule" is a nucleic acid molecule (e.g., a polynucleotide) that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein, a "nucleic acid molecule construct" is a nucleic acid molecule, either single- or double-stranded, that has been modified through human intervention to contain segments of nucleic acid combined and juxtaposed in an arrangement not existing in nature.

As used herein, an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the terms "approximately" or "about" in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

It is contemplated that any embodiment discussed in this specification can be implemented with respect to any method, kit, reagent, or composition of the invention, and vice versa. Furthermore, compositions of the invention can be used to achieve methods of the invention.

II. Overview

As described in Examples 1-3 herein, the present invention provides monoclonal anti-MLP antibodies that bind to human full length mucin-like protein "MLP" (set forth as SEQ ID NO:1) with high affinity and are capable of use as a biomarker for detection of the presence of ovarian, pancreatic, colorectal, breast, appendiceal, lung, renal, cervical, biliary, esophageal, epithelial skin and/or other mucin-secreting types of cancer in a serum sample from a human subject. In particular embodiments, the invention provides monoclonal antibodies that specifically bind to an epitope in the C-terminal region of human MLP (set forth as SEQ ID NO:4). In some embodiments, the invention provides monoclonal antibodies that specifically bind to an epitope in the C-terminal region of MLP comprising or consisting of amino acid residues 397-431 of SEQ ID NO:1 (set forth as SEQ ID NO:5). In some embodiments, the invention provides monoclonal antibodies that specifically bind to an epitope in the C-terminal region of MLP comprising or consisting of amino acid residues 403-431 of SEQ ID NO:1 (set forth as SEQ ID NO:6).

As described herein, the subject antibodies bind to recombinant MLP and also to the naturally occurring glycosylated form of MLP, referred to as "gMLP" that is secreted by epithelial cancer cells, such as ovarian cancer cells, pancreatic cancer cells and, for example, other adenocarcinoma cells. Therefore, the subject antibodies can be used in diagnostic methods to detect the presence of MLP in a biological sample obtained from a subject or in a subject in vivo (e.g., diagnostic imaging) as a biomarker for the presence or absence of epithelial cancer cells (e.g., ovarian or pancreatic cancer cells) in the subject.

III. MLP Antigens

As described in Example 1 herein, the present inventors have identified a single exon gene on chromosome 7 which encodes the full-length sequence of MLP (also referred to as MUC-B), set forth as SEQ ID NO:1, as shown in FIG. 1, which has a length of 431 amino acid residues and contains a novel C-terminal region (set forth as SEQ ID NO:4). As further described in Examples 1-3 herein, the inventors have used the C-terminal region of MLP as an antigen to generate anti-MLP antibodies suitable for use in the diagnostic and therapeutic methods described herein.

Accordingly, in one aspect, the present invention provides an isolated polypeptide comprising or consisting of the amino acid sequence set forth in SEQ ID NO:1 or a variant thereof having an amino acid sequence that is at least 90%, such as at least 91%, 92%, 93%, 94%, 95%, 96%, 97%, 98% or 99% identity to SEQ ID NO:1.

In one embodiment, the present invention provides an isolated polypeptide comprising or consisting of the amino acid sequence set forth in SEQ ID NO:4, or a variant thereof having an amino acid sequence that is at least 90%, such as at least 91%, 92%, 93%, 94%, 95%, 96%, 97%, 98% or 99% identity to SEQ ID NO:4.

In one embodiment, the present invention provides an isolated polypeptide comprising or consisting of the amino acid sequence set forth in SEQ ID NO:3, or a variant thereof having an amino acid sequence that is at least 90%, such as at least 91%, 92%, 93%, 94%, 95%, 96%, 97%, 98% or 99% identity to SEQ ID NO:3.

In one embodiment, the present invention provides an isolated polypeptide comprising or consisting of the amino acid sequence set forth in SEQ ID NO:5, or a variant thereof having an amino acid sequence that is at least 90%, such as at least 91%, 92%, 93%, 94%, 95%, 96%, 97%, 98% or 99% identity to SEQ ID NO:5.

In one embodiment, the present invention provides an isolated polypeptide comprising or consisting of the amino acid sequence set forth in SEQ ID NO:6, or a variant thereof having an amino acid sequence that is at least 90%, such as at least 91%, 92%, 93%, 94%, 95%, 96%, 97%, 98% or 99% identity to SEQ ID NO:6.

In one embodiment, the present invention provides an isolated nucleic acid molecule encoding the amino acid sequence of the polypeptide set forth as SEQ ID NO:1, or encoding a variant thereof having an amino acid sequence that is at least 90%, such as at least 91%, 92%, 93%, 94%, 95%, 96%, 97%, 98% or 99% identity to SEQ ID NO: 1. In one embodiment, the present invention provides an isolated nucleic acid molecule encoding the amino acid sequence of the polypeptide set forth as SEQ ID NO:4, or encoding a variant thereof having an amino acid sequence that is at least 90%, such as at least 91%, 92%, 93%, 94%, 95%, 96%, 97%, 98% or 99% identity to SEQ ID NO:4. In one embodiment, the isolated nucleic acid sequence comprises or consists of SEQ ID NO:2. In one embodiment, the present invention provides an isolated nucleic acid molecule encoding the amino acid sequence of the polypeptide set forth as SEQ ID NO:5, or encoding a variant thereof having an amino acid sequence that is at least 90%, such as at least 91%, 92%, 93%, 94%, 95%, 96%, 97%, 98% or 99% identity to SEQ ID NO:5. In one embodiment, the present invention provides an isolated nucleic acid molecule encoding the amino acid sequence of the polypeptide set forth as SEQ ID NO:6, or encoding a variant thereof having an amino acid sequence that is at least 90%, such as at least 91%, 92%, 93%, 94%, 95%, 96%, 97%, 98% or 99% identity to SEQ ID NO:6.

In one embodiment, the invention provides an expression vector encoding at least one of SEQ ID NO:1, SEQ ID NO:3, SEQ ID NO:4, SEQ ID NO:5 or SEQ ID NO:6. In one embodiment the invention provides an expression vector comprising SEQ ID NO:2. In one embodiment, the invention provides a cell comprising a nucleic acid encoding at least one of SEQ ID NO:1, SEQ ID NO:3, SEQ ID NO:4, SEQ ID NO:5 or SEQ ID NO:6.

IV. Anti-MLP Monoclonal Antibodies

As described in Examples 1 and 2 herein, the inventors have used the C-terminal region of MLP (SEQ ID NO:4) as an antigen to generate anti-MLP antibodies suitable for use in the diagnostic and therapeutic methods described herein. As described in Example 3, the variable light and heavy chain fragments of several representative anti-MLP monoclonal antibodies have been cloned and sequenced. FIG. 10A is an amino acid sequence alignment of the variable heavy chain regions of three anti-MLP clones that were identified as having high binding affinity to the C-terminal region of MLP. FIG. 10B is an amino acid sequence alignment of the variable light chain regions of three anti-MLP clones that were identified as having high binding affinity to the C-terminal region of MLP.

Substitutable positions of an MLP-specific antibody, as well the choice of amino acids that may be substituted into those positions, are revealed by aligning the heavy and light chain amino acid sequences of the MLP-specific monoclonal antibodies discussed above, and determining which amino acids occur at which positions of those antibodies. In one exemplary embodiment, the heavy and light chain amino acid sequences are aligned, and the identity of amino acids at each position of the exemplary antibodies is determined. As illustrated in TABLES 2 and 3 and FIGS. 10A and 10B (illustrating the amino acids present at each position of the heavy and light chains of the MLP-specific monoclonal antibodies), several substitutable positions, as well as the amino acid residues that can be substituted into those positions, are readily identified.

TABLE 1

Summary of MLP-specific monoclonal antibody clones:

| clone reference# | VH | VL | Ig format | K_D (binding to rMLP) |
|---|---|---|---|---|
| Clone 11 | SEQ ID NO: 7 (encoded by SEQ ID NO: 29) | SEQ ID NO: 10 (encoded by SEQ ID NO: 32) | IgG2b, K | 0.2 nM |
| Clone B | SEQ ID NO: 8 (encoded by SEQ ID NO: 30) | SEQ ID NO: 11 (encoded by SEQ ID NO: 33) | IgG2a, K | <1 nM |
| Clone C | SEQ ID NO: 9 (encoded by SEQ ID NO: 31) | SEQ ID NO: 12 (encoded by SEQ ID NO: 34) | IgG1, K | <1 nM |

In certain embodiments, a subject MLP-specific monoclonal antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the heavy chain variable domain sequences set forth in TABLE 1.

In some embodiments, a subject MLP-specific monoclonal antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to clone 11 (VH), set forth as SEQ ID NO:7. In some embodiments, the subject MLP-specific monoclonal antibody has a heavy chain variable domain that comprises, or consists of SEQ ID NO:7.

In some embodiments, a subject MLP-specific monoclonal antibody has a heavy chain variable domain that is substantially identical (e.g., at least about 70%, at least 75%, at least about 80%, at least about 85%, at least about 90%, at least about 95%, at least about 96% identical, at least about 97% identical, at least about 98% identical, or at least 99% identical) to clone B (VH), set forth as SEQ ID NO:8. In some embodiments, the subject MLP-specific monoclonal antibody has a heavy chain variable domain that comprises, or consists of SEQ ID NO:8.

In some embodiments, a subject MLP-specific monoclonal antibody has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to clone C (VH), set forth as SEQ ID NO:9. In some embodiments, the subject MLP-specific monoclonal antibody has a heavy chain variable domain that comprises, or consists of SEQ ID NO:9.

In some embodiments, a subject MLP-specific monoclonal antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the light chain variable domain sequences set forth in TABLE 1.

In some embodiments, a subject MLP-specific monoclonal antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to clone 11 (VL), set forth as SEQ ID NO:10. In some embodiments, the subject MLP-specific monoclonal antibody has a light chain that comprises, or consists of SEQ ID NO:10.

In some embodiments, a subject MLP-specific monoclonal antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to clone B (VL), set forth as SEQ ID NO:11. In some embodiments, the subject MLP-specific monoclonal inhibitory antibody has a light chain that comprises, or consists of SEQ ID NO:11.

In some embodiments, a subject MLP-specific monoclonal antibody has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical) to clone C (VL), set forth as SEQ ID NO:12. In some embodiments, the subject MLP-specific monoclonal antibody has a light chain that comprises, or consists of SEQ ID NO:12.

In some embodiments, the MLP-specific monoclonal antibodies of the invention contain a heavy or light chain that is encoded by a nucleotide sequence that hybridizes under high stringency conditions to a nucleotide sequence encoding a heavy or light chain, as set forth in TABLE 1 (e.g., SEQ ID NO:29, SEQ ID NO:30, SEQ ID NO:31, SEQ ID NO:32, SEQ ID NO:33 or SEQ ID NO:34). High stringency conditions include incubation at 50° C. or higher in 0.1×SSC (15 mM saline/0.15 mM sodium citrate).

In some embodiments, the MLP-specific monoclonal antibodies of the invention have a heavy chain variable region comprising one or more CDRs (CDR1, CDR2 and/or CDR3) that are substantially identical (e.g., at least about 70%, at least 75%, at least about 80%, at least about 85%, at least about 90%, at least about 95%, or at least about 96% identical, or at least about 97% identical, or at least about 98% identical, or at least about 99% identical), or comprise or consist of the identical sequence as compared to the amino acid sequence of the CDRs of any of the heavy chain variable sequences described below in TABLES 2A-G and TABLE 3.

In some embodiments, the MLP-specific monoclonal antibodies of the invention have a light chain variable region comprising one or more CDRs (CDR1, CDR2 and/or CDR3) that are substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), or comprise or consist of the identical sequence as compared to the amino acid sequence of the CDRs of any of the light chain variable sequences described below in TABLES 4A-F and TABLE 5.

Heavy Chain Variable Region of MLP-Specific Monoclonal Antibodies

TABLE 2A

| Heavy chain aa | Heavy chain (aa 1-20) | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| Clone 11 (SEQ NO: 7) | E | V | Q | L | Q | Q | S | G | P | E | L | V | K | P | G | A | S | V | K | I |
| Clone B (SEQ NO: 8) | E | V | Q | L | Q | Q | S | G | P | E | L | V | K | P | G | A | S | V | K | I |
| Clone C (SEQ NO: 9) | D | V | K | L | Q | E | S | G | G | G | L | V | Q | P | G | G | S | M | K | L |

TABLE 2B

| Heavy chain aa | Heavy chain (aa 21-40) | | | | | | | | | | CDR-H1 | | | | | | | | | |
|---|---|---|---|---|---|---|---|---|---|---|---|---|---|---|---|---|---|---|---|---|
| | 21 | 22 | 23 | 24 | 25 | 26 | 27 | 28 | 29 | 30 | 31 | 32 | 33 | 34 | 35 | 36 | 37 | 38 | 39 | 40 |
| Clone 11 (SEQ NO: 7) | S | C | K | A | S | G | Y | A | F | T | G | F | Y | I | H | W | M | K | Q | S |
| Clone B (SEQ NO: 8) | S | C | K | A | S | G | Y | S | F | T | G | F | Y | I | H | W | V | K | Q | S |
| Clone C (SEQ NO: 9) | S | C | V | A | S | G | F | T | F | S | N | Y | W | M | N | W | V | R | Q | S |

TABLE 2C

| Heavy chain aa | Heavy chain (aa 41-57) | | | | | | | | | | | | CDR-H2 | | | | | | |
|---|---|---|---|---|---|---|---|---|---|---|---|---|---|---|---|---|---|---|---|
| | 41 | 42 | 43 | 44 | 45 | 46 | 47 | 48 | 49 | 50 | 51 | 52 | 52A | 52B | 52C | 53 | 54 | 55 | 56 | 57 |
| Clone 11 (SEQ NO: 7) | H | V | K | S | L | E | W | I | G | R | I | H | P | | | Y | N | G | A | T |
| Clone B (SEQ NO: 8) | H | V | K | S | L | E | W | I | G | R | I | H | P | | | Y | N | G | A | P |
| Clone C (SEQ NO: 9) | P | E | K | G | L | E | W | V | A | E | I | R | L | K | S | N | N | Y | A | I |

TABLE 2D

Heavy chain (aa 58-77)

| Heavy chain aa | CDR-H2 (cont'd) | | | | | | | | | | | | | | | | | | | |
|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 |
| Clone 11 (SEQ NO: 7) | S | Y | N | Q | N | F | K | D | R | A | S | L | T | V | D | E | S | S | S | T |
| Clone B (SEQ NO: 8) | T | Y | N | Q | N | F | K | D | R | A | R | L | T | V | H | E | S | S | S | T |
| Clone C (SEQ NO: 9) | N | Y | A | E | S | V | K | G | R | F | T | I | S | R | D | D | S | K | S | S |

TABLE 2E

Heavy chain (aa 78-94)

| Heavy chain aa | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|
| Clone 11 (SEQ NO: 7) | A | Y | M | E | F | Y | G | L | T | S | E | D | S | A | V | Y | Y | C | A | R |
| Clone B (SEQ NO: 8) | A | Y | M | E | F | F | G | L | T | S | E | D | S | A | V | Y | Y | C | A | R |
| Clone C (SEQ NO: 9) | V | Y | L | D | M | N | N | L | R | A | E | D | T | G | I | Y | Y | C | T | S |

TABLE 2F heavy chain (aa 95-108)

| Heavy chain aa | CDR-H3 | | | | | | | | | | | | | | | | | | | |
|---|---|---|---|---|---|---|---|---|---|---|---|---|---|---|---|---|---|---|---|---|
| | 95 | 96 | 97 | 98 | 99 | 100 | 100A | 100B | 100C | 100D | 100E | 100F | 101 | 102 | 103 | 104 | 105 | 106 | 107 | 108 |
| Clone 11 (SEQ NO: 7) | E | R | V | Y | Y | Y | G | S | T | Y | E | F | D | S | W | G | Q | G | T | T |
| Clone B (SEQ NO: 8) | E | R | V | Y | Y | Y | G | S | T | Y | E | F | D | F | W | G | Q | G | T | T |
| Clone C (SEQ NO: 9) | Y | Y | G | S | S | L | Y | Y | L | | | | D | Y | W | G | Q | G | T | T |

TABLE 2G heavy chain (aa 109-113)

| Heavy chain aa | 109 | 110 | 111 | 112 | 113 |
|---|---|---|---|---|---|
| Clone 11 (SEQ NO: 7) | L | T | V | S | S |
| Clone B (SEQ NO: 8) | L | T | V | S | S |

TABLE 2G-continued heavy chain (aa 109-113)

| Heavy chain aa | 109 | 110 | 111 | 112 | 113 |
|---|---|---|---|---|---|
| Clone C (SEQ NO: 9) | L | T | V | S | S |

Presented below are the heavy chain variable region (VH) sequences for the monoclonal antibodies listed above in TABLE 1 and TABLES 2A-G.

The Kabat CDRs (31-35 (H1), 50-66 (H2) and 95-102 (H3)) are bolded; and the Chothia CDRs (26-32 (H1), 52-56 (H2) and 95-102 (H3)) are underlined.

Clone 11 heavy chain variable region (VH)
(SEQ ID NO: 7)
EVQLQQSGPELVKPGASVKISCKAS<u>GYAFTGFYIH</u>WMKQSHVKSLEWIGR IHPYNGATSYNQNFKDRASLTVDESSSTAYMEFYGLTSEDSAVYYCARER VYYYGSTYEFDSWGQGTTLTVSS Clone B heavy chain variable region (VH)
(SEQ ID NO: 8)
EVQLQQSGPELVKPGASVKISCKAS<u>GYSFTGFYIH</u>WVKQSHVKSLEWIGR IHPYNGAPTYNQNFKDRARLTVRESSSTAYMEFFGLTSEDSAVYYCARER VYYYGSTYEFDFWGQGTTLTVSS Clone C heavy chain variable region (VH)
(SEQ ID NO: 9)
DVKLQESGGGLVQPGGSMKLSCVAS<u>GFTFSNYWMN</u>WVRQSPEKGLEWVAE IRLKSNNYAINYAESVKGRFTISRDDSKSSVYLDMNNLRAEDTGIYYCTS YYGSSLYYLDYWGQGTTLTVSS

TABLE 3

Heavy Chain CDRs of MLP-specific monoclonal antibodies

| Clone Reference | CDR | Amino Acid Sequence | SEQ ID NO: |
|---|---|---|---|
| Clone 11 | CDR-H1 (kabat) | GFYIH | SEQ ID NO: 13 |
| Clone B | CDR-H1 (kabat) | GFYIH | SEQ ID NO: 13 |
| Clone C | CDR-H1 (kabat) | NYWMN | SEQ ID NO: 17 |
| Clone 11 | CDR-H2 (kabat) | RIHPYNGATSYNQNFKD | SEQ ID NO: 14 |
| Clone B | CDR-H2 (kabat) | RIHPYNGAPTYNQNFKD | SEQ ID NO: 16 |
| Clone C | CDR-H2 (kabat) | EIRLKSNNYAINYAESVKG | SEQ ID NO: 18 |
| Consensus from clones 11 and B | CDR-H2 (kabat) | RIHPYNGAXXYNQNFKD (wherein X at position 9 is T or P; and X at position 10 is S or T) | SEQ ID NO: 20 |
| Clone 11 | CDR-H3 (kabat) | ERVYYYGSTYEFDS | SEQ ID NO: 15 |
| Clone B | CDR-H3 (kabat) | ERVYYYGSTYEFDF | SEQ ID NO: 35 |
| Clone C | CDR-H3 (kabat) | YYGSSLYYLDY | SEQ ID NO: 19 |
| Consensus from clones 11 and B | CDR-H3 (kabat) | ERVYYYGSTYEFDX (wherein X at position 14 is S or F) | SEQ ID NO: 36 |

Light Chain Variable Regions of MLP-Specific Monoclonal Antibodies

TABLE 4A

Light chain (aa 1-20)

| Light chain aa | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Clone 11 (SEQ NO: 10) | D | V | L | M | T | Q | T | P | L | S | L | P | V | S | L | G | D | Q | A | S |
| Clone B (SEQ NO: 11) | D | V | L | M | T | Q | T | P | L | S | L | P | V | S | L | G | D | Q | A | S |

TABLE 4A-continued

Light chain (aa 1-20)

| Light chain aa | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Clone C (SEQ NO: 12) | Q | I | V | L | T | Q | S | P | V | I | M | S | A | S | P | G | E | K | V | T |

TABLE 4B

Light chain (aa 21-35)

| Light chain | | | | CDR-L1 | | | | | | | | | | | | | |
|---|---|---|---|---|---|---|---|---|---|---|---|---|---|---|---|---|---|
| aa (Kabat) | 21 | 22 | 23 | 24 | 25 | 26 | 27 | 27A | 27B | 27C | 27D | 27E | 28 | 29 | 30 | 31 | 32 | 33 | 34 | 35 |
| aa (Chothia) | 21 | 22 | 23 | 24 | 25 | 26 | 27 | 28 | 29 | 30 | 30A | 30B | 30C | 30D | 30E | 31 | 32 | 33 | 34 | 35 |
| Clone 11 (SEQ NO: 10) | I | S | C | <u>R</u> | <u>S</u> | <u>G</u> | <u>Q</u> | <u>S</u> | <u>I</u> | <u>V</u> | <u>H</u> | <u>T</u> | <u>S</u> | <u>G</u> | <u>V</u> | <u>T</u> | <u>Y</u> | <u>L</u> | <u>S</u> | W |
| Clone B (SEQ NO: 11) | I | S | C | <u>R</u> | <u>S</u> | <u>G</u> | <u>Q</u> | <u>S</u> | <u>I</u> | <u>V</u> | <u>H</u> | <u>S</u> | <u>S</u> | <u>G</u> | <u>V</u> | <u>T</u> | <u>Y</u> | <u>L</u> | <u>S</u> | W |
| Clone C (SEQ NO: 12) (Kabat) | I | S | C | <u>S</u> | <u>A</u> | <u>S</u> | <u>S</u> | | | | | | <u>S</u> | <u>V</u> | <u>S</u> | <u>N</u> | <u>M</u> | <u>Y</u> | | W |
| Clone C (SEQ NO: 12) (Chothia) | I | S | C | <u>S</u> | <u>A</u> | <u>S</u> | <u>S</u> | <u>S</u> | <u>V</u> | <u>S</u> | | | | | | <u>N</u> | <u>M</u> | <u>Y</u> | | W |

TABLE 4C

Light chain (aa 36-55)

| Light chain aa | 36 | 37 | 38 | 39 | 40 | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|---|---|---|---|---|
| | | | | | | | | | | | | | | | CDR-L2 | | | | | |
| Clone 11 (SEQ NO: 10) | Y | L | Q | K | P | G | Q | S | P | K | L | L | I | Y | <u>K</u> | <u>V</u> | <u>F</u> | <u>Y</u> | <u>R</u> | <u>F</u> |
| Clone B (SEQ NO: 11) | Y | L | Q | K | P | G | Q | S | P | K | L | L | I | Y | <u>K</u> | <u>V</u> | <u>F</u> | <u>Y</u> | <u>R</u> | <u>F</u> |
| Clone C (SEQ NO: 12) | Y | Q | Q | K | P | G | S | S | P | K | A | W | I | Y | <u>R</u> | <u>T</u> | <u>S</u> | <u>N</u> | <u>L</u> | <u>A</u> |

TABLE 4D

Light chain (aa 56-75)

| Light chain aa | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|
| | CDR-L2 (cont'd) | | | | | | | | | | | | | | | | | | | |
| Clone 11 (SEQ NO: 10) | <u>S</u> | G | V | P | D | R | F | S | G | S | G | S | G | T | D | F | T | L | K | I |

TABLE 4D-continued

Light chain (aa 56-75)

| Light chain aa | CDR-L2 (cont'd) 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|
| Clone B (SEQ NO: 11) | <u>S</u> | G | V | P | D | R | F | S | G | S | G | S | G | T | D | F | T | L | K | I |
| Clone C (SEQ NO: 12) | <u>S</u> | G | V | P | A | R | F | S | G | S | G | S | G | T | S | Y | S | L | T | I |

TABLE 4E

Light chain (aa 76-95)

| Light chain aa | 76 | 77 | 78 | 79 | 80 | 81 | 82 | 83 | 84 | 85 | 86 | 87 | 88 | CDR-L3 89 | 90 | 91 | 92 | 93 | 94 | 95 |
|---|---|---|---|---|---|---|---|---|---|---|---|---|---|---|---|---|---|---|---|---|
| Clone 11 (SEQ NO: 10) | S | R | V | E | S | E | D | L | G | V | Y | Y | C | <u>F</u> | <u>Q</u> | <u>G</u> | <u>S</u> | <u>H</u> | <u>V</u> | <u>P</u> |
| Clone B (SEQ NO: 11) | S | R | V | E | A | E | D | L | G | V | Y | Y | C | <u>F</u> | <u>Q</u> | <u>G</u> | <u>S</u> | <u>H</u> | <u>V</u> | <u>P</u> |
| Clone C (SEQ NO: 12) | S | S | M | E | A | E | D | A | A | T | Y | Y | C | <u>H</u> | <u>Q</u> | <u>Y</u> | <u>Q</u> | <u>S</u> | <u>Y</u> | <u>P</u> |

TABLE 4F

Light chain (aa 96-107)

| aa | CDR-L3 (cont'd) 96 | 97 | 98 | 99 | 100 | 101 | 102 | 103 | 104 | 105 | 106 | 107 |
|---|---|---|---|---|---|---|---|---|---|---|---|---|
| Clone 11 (SEQ NO: 10) | <u>P</u> | <u>T</u> | F | G | A | G | T | K | L | E | L | K |
| Clone B (SEQ NO: 11) | <u>P</u> | <u>T</u> | F | G | T | G | T | K | L | E | L | K |
| Clone C (SEQ NO: 12) | <u>R</u> | <u>T</u> | F | G | A | G | T | K | L | E | I | K |

Presented below are the light chain variable region (VL) sequences for the MLP-specific monoclonal antibodies listed above in TABLE 1 and TABLES 4A-F.

The Kabat CDRs (24-34 (L1); 50-56 (L2); and 89-97 (L3) are bolded; and the Chothia CDRs (24-34 (L1); 50-56 (L2) and 89-97 (L3) are underlined. These regions are the same whether numbered by the Kabat or Chothia system.

Clone 11 light chain variable region (VL)
(SEQ ID NO: 10)
DVLMTQTPLSLPVSLGDQASISC<u>RSGQSIVHTSGVTYLS</u>WYLQKPGQSPK
LLIY<u>KVFYRFS</u>GVPDRFSGSGSGTDFTLKISRVESEDLGVYYC<u>FQGSHVP
PTFGAGTKLELK</u>

Clone B light chain variable region (VL)
(SEQ ID NO: 11)
DVLMTQTPLSLPVSLGDQASISC<u>RSGQSIVHSSGVTYLS</u>WYLQKPGQSPK
LLIY<u>KVFYRFS</u>GVPDRFSGSGSGTDFTLKISRVEAEDLGVYYC<u>FQGSHVP
PTFGTGTKLELK</u>

Clone C light chain variable region (VL)
(SEQ ID NO: 12)
QIVLTQSPVIMSASPGEKVTISC<u>SASSSVSNMY</u>WYQQKPGSSPKAWIY<u>RT
SNLAS</u>GVPARFSGSGSGTSYSLTISSMEAEDAATYYC<u>HQYQSYPRT</u>FGAG
TKLEIK

TABLE 5

Light Chain CDRs (Kabat) of the MLP-specific antibodies

| Reference | CDR | Amino Acid Sequence | SEQ ID NO: |
|---|---|---|---|
| Clone 11 | CDR-L1 | RSGQSIVHTSGVTYLS | SEQ ID NO: 21 |
| Clone B | CDR-L1 | RSGQSIVHSSGVTYLS | SEQ ID NO: 24 |

TABLE 5-continued

Light Chain CDRs (Kabat) of the MLP-specific antibodies

| Reference | CDR | Amino Acid Sequence | SEQ ID NO: |
|---|---|---|---|
| Clone C | CDR-L1 | SASSSVSNMY | SEQ ID NO: 25 |
| Consensus of clone 11 and B | CDR-L1 | RSGQSIVHXSGVTYLS (wherein X at position 9 is T or S) | SEQ ID NO: 28 |
| Clone 11 | CDR-L2 | KVFYRFS | SEQ ID NO: 22 |
| Clone B | CDR-L2 | KVFYRFS | SEQ ID NO: 22 |
| Clone C | CDR-L2 | RTSNLAS | SEQ ID NO: 26 |
| Clone 11 | CDR-L3 | FQGSHVPPT | SEQ ID NO: 23 |
| Clone B | CDR-L3 | FQGSHVPPT | SEQ ID NO: 23 |
| Clone C | CDR-L3 | HQYQSYPRT | SEQ ID NO: 27 |

In accordance with the foregoing, in one aspect, the present invention provides an isolated antibody, or antigen binding fragment thereof, that specifically binds to an epitope in the C-terminal region of human mucin-like protein, set forth as SEQ ID NO:4, such as an epitope in SEQ ID NO:5 or SEQ ID NO:6. In one embodiment, the antibody is a monoclonal antibody. In one embodiment, said antibody or antigen binding fragment thereof is capable of binding to glycosylated human MLP secreted from an epithelial cancer cell line. In one embodiment, said antibody or antigen binding fragment thereof is capable of binding to glycosylated human MLP in an ELISA assay format. In one embodiment, said antibody or antigen binding fragment thereof binds to human MLP with an $K_D$ of less than 10 nM, such as less than 1 nM. In one embodiment, said antibody, or antigen binding fragment thereof recognizes at least part of an epitope recognized by one or more reference antibodies selected from the group consisting of:

(i) the monoclonal antibody MLP Clone 11 produced by the hybridoma cell line deposited at the ATCC on Oct. 30, 2014 having the ATCC Designation Number PTA-121699;

(ii) the monoclonal antibody MLP Clone B produced by the hybridoma cell line deposited at the ATCC on Oct. 30, 2014 having the ATCC Designation Number PTA-121700; and (iii) the monoclonal antibody MLP Clone C produced by the hybridoma cell line deposited at the ATCC on Oct. 30, 2014 having the ATCC Designation Number PTA-121701.

In one embodiment, said antibody comprises a variable region of the heavy chain comprising or consisting of a sequence which is at least 90% identical (e.g., at least 91%, or at least 92%, or at least 93%, or at least 94%, or at least 95%, or at least 96%, or at least 97%, or at least 98%, or at least 99% identical) to an amino acid sequence selected from the group consisting of SEQ ID NO:7, SEQ ID NO:8 and SEQ ID NO:9. In one embodiment, said antibody comprises a variable region of the light chain comprising or consisting of a sequence which is at least 90% identical (e.g., at least 91%, or at least 92%, or at least 93%, or at least 94%, or at least 95%, or at least 96%, or at least 97%, or at least 98%, or at least 99% identical) to an amino acid sequence selected from the group consisting of SEQ ID NO:10, SEQ ID NO:11 and SEQ ID NO:12.

In another aspect, the invention provides an isolated MLP-specific monoclonal antibody, or antigen binding fragment thereof, that binds to human MLP (SEQ ID NO:1 or SEQ ID NO:4), comprising: (i) a heavy chain variable region comprising CDR-H1, CDR-H2 and CDR-H3 sequences; and (ii) a light chain variable region comprising CDR-L1, CDR-L2 and CDR-L3, wherein the heavy chain variable region CDR-H3 sequence comprises an amino acid sequence set forth as SEQ ID NO:15, SEQ ID NO:35, SEQ ID NO:36 or SEQ ID NO:19, and conservative sequence modifications thereof, wherein the light chain variable region CDR-L3 sequence comprises an amino acid sequence set forth as SEQ ID NO:23 or SEQ ID NO:27, and conservative sequence modifications thereof, and wherein the isolated antibody binds human MLP (SEQ ID NO:1 or SEQ ID NO:4). In one embodiment, the MLP-specific monoclonal antibody, or antigen-binding fragment thereof, specifically binds to an epitope in the C-terminal region of human MLP, set forth as SEQ ID NO:4 (i.e., amino acids 279-431 of SEQ ID NO:1), such as an epitope in the C-terminal region of human MLP set forth as SEQ ID NO:5 (i.e., amino acids 397-431 of SEQ ID NO:1); or such as an epitope in the C-terminal region of human MLP set forth as SEQ ID NO:6 (i.e, amino acids 403-431 of SEQ ID NO:1)

In one embodiment, the heavy chain variable region CDR-H2 sequence comprises an amino acid sequence set forth as SEQ ID NO: 14, 16 or 18, and conservative sequence modifications thereof. In one embodiment, the heavy chain variable region CDR-H1 sequence comprises an amino acid sequence set forth as SEQ ID NO:13 or 17, and conservative modifications thereof. In one embodiment, the light chain variable region CDR-L2 sequence comprises an amino acid sequence set forth as SEQ ID NO:22 or SEQ ID NO:26 and conservative modifications thereof. In one embodiment, the light chain variable region CDR-L1 sequence comprises an amino acid sequence set forth as SEQ ID NO:21, 24, 25 or 28 and conservative modifications thereof.

In one embodiment, the CDR-H2 of the heavy chain variable region comprises SEQ ID NO:20. In one embodiment, the amino acid sequence set forth in SEQ ID NO:20 contains a T (Thr) or P (Pro) at position 9. In one embodiment, the amino acid sequence set forth in SEQ ID NO:20 contains an S (Ser) or T (Thr) at position 10. In one embodiment, the CDR-H3 of the heavy chain variable region comprises SEQ ID NO:15 (as shown in TABLE 3).

In one embodiment, the CDR-H3 of the heavy chain variable region comprises SEQ ID NO:35 (as shown in TABLE 3). In one embodiment, the CDR-H3 of the heavy chain variable region comprises SEQ ID NO:36 (as shown in TABLE 3).

In one embodiment, the CDR-L1 of the light chain variable region comprises SEQ ID NO:28 (as shown in TABLE 5). In one embodiment, the amino acid set forth in SEQ ID NO:28 contains a T (Thr) at position 9. In one embodiment, the amino acid sequence set forth in SEQ ID NO:28 contains an S (Ser) at position 9.

In one embodiment, the CDR-L2 of the light chain variable region comprises SEQ ID NO:22 (as shown in TABLE 5).

In one embodiment, the CDR-L3 of the light chain variable region comprises SEQ ID NO:23 (as shown in TABLE 5).

In one embodiment, said antibody or antigen binding fragment thereof binds MLP (SEQ ID NO:1 or SEQ ID NO:4) with a $K_D$ of 10 nM or less. In one embodiment, the conservative sequence modifications thereof comprise or consist of a molecule which contains variable regions that are identical to the recited variable domain(s), except for a combined total of 1, 2, 3, 4, 5, 6, 7, 8 9 or 10 amino acid substitutions within the CDR regions of the heavy chain variable region, and/or up to a combined total of 1, 2, 3, 4, 5, 6, 7, 8, 9, or 10 amino acid substitutions with said CDR regions of the light chain variable region.

In another aspect, the invention provides an isolated monoclonal antibody, or antigen binding fragment thereof, that binds to human MLP (SEQ ID NO:1 or SEQ ID NO:4) wherein the antibody comprises: I) a) a heavy chain variable region, numbered according to Kabat, comprising: i) a heavy chain CDR-H1 comprising the amino acid sequence from 31-35 of SEQ ID NO:7, SEQ ID NO:8 or SEQ ID NO:9; and ii) a heavy chain CDR-H2 comprising the amino acid sequence from 50-66 of SEQ ID NO:7, SEQ ID NO:8 or SEQ ID NO:9; and iii) a heavy chain CDR-H3 comprising the amino acid sequence from 95-102 of SEQ ID NO:7; SEQ ID NO:8 or SEQ ID NO:9; and b) a light chain variable region, numbered according to Kabat, comprising: i) a light chain CDR-L1 comprising the amino acid sequence from 24-34 of SEQ ID NO:10, SEQ ID NO:11 or SEQ ID NO:12; and ii) a light chain CDR-L2 comprising the amino acid sequence from 50-56 of SEQ ID NO:10, SEQ ID NO:11 or SEQ ID NO:12; and iii) a light chain CDR-L3 comprising the amino acid sequence from 89-97 of SEQ ID NO:10, SEQ ID NO:11 or SEQ ID NO:12; or II) a variant thereof that is otherwise identical to said variable domains, except for up to a combined total of 1, 2, 3, 4, 5, 6, 7, 8, 9 or 10 amino acid substitutions within said CDR regions of said heavy chain variable region and up to a combined total of 1, 2, 3, 4, 5, 6, 7, 8, 9, or 10 amino acid substitutions within said CDR regions of said light chain variable region, wherein the antibody or variant thereof binds to human MLP (SEQ ID NO:1 or SEQ ID NO:4). In one embodiment, said variant comprises an amino acid substitution at one or more positions selected from the group consisting of position 28, 37, 57, 58, 68, 72, 82A or 102 of said heavy chain variable region, numbered according to Kabat. In one embodiment, said variant comprises an amino acid substitution at one or more positions selected from the group consisting of position 27E, 80 or 100 of said light chain variable region, numbered according to Kabat. In one embodiment, the heavy chain variable region of said antibody comprises SEQ ID NO:7. In one embodiment, the heavy chain variable region of said antibody comprises or consists of SEQ ID NO:8. In one embodiment, the heavy chain variable region comprises or consists of SEQ ID NO:9. In one embodiment, the light chain variable region of said antibody comprises or consists of SEQ ID NO:10. In one embodiment, the light chain variable region of said antibody comprises or consists of SEQ ID NO:11. In one embodiment, the light chain variable region of said antibody comprises or consists of SEQ ID NO:12.

In another aspect, the invention provides an isolated monoclonal antibody that binds to human MLP (SEQ ID NO:1 or SEQ ID NO:4), wherein the antibody comprises: I) a) a heavy chain variable region, numbered according to Kabat, comprising, i) a heavy chain CDR-H1 comprising the amino acid sequence from 31-35 of SEQ ID NO:7; and ii) a heavy chain CDR-H2 comprising the amino acid sequence from 50-66 of SEQ ID NO:7; and iii) a heavy chain CDR-H3 comprising the amino acid sequence from 95-102 of SEQ ID NO:7; and b) a light chain variable region comprising: i) a light chain CDR-L1 comprising the amino acid sequence from 24-34 of SEQ ID NO:10; and ii) a light chain CDR-L2 comprising the amino acid sequence from 50-56 of SEQ ID NO:10; and iii) a light chain CDR-L3 comprising the amino acid sequence from 89-97 of SEQ ID NO:10; or II) a variant thereof that is otherwise identical to said variable domains, except for up to a combined total of 1, 2, 3, 4, 5, 6, 7, 8, 9, or 10 amino acid substitutions within said CDR regions of said heavy chain variable region and up to a combined total of 1, 2, 3, 4, 5, 6, 7, 8, 9, or 10 amino acid substitutions within said CDR regions of said light chain variable region, wherein the antibody or variant thereof binds to human MLP (SEQ ID NO:1 or SEQ ID NO:4). In one embodiment, said variant comprises an amino acid substitution at one or more positions selected from the group consisting of position 28, 37, 57, 58, 68, 72, 82A or 102 of said heavy chain variable region, numbered according to Kabat. In one embodiment, said variant comprises an amino acid substitution at one or more positions selected from the group consisting of position 27E, 80 or 100 of said light chain variable region, numbered according to Kabat. In one embodiment, the heavy chain of said antibody comprises SEQ ID NO:7, or a variant thereof comprising at least 80% identity to SEQ ID NO:7 (e.g., at least 85%, at least 90%, at least 95% or at least 98% identity to SEQ ID NO:7). In one embodiment, the light chain of said antibody comprises SEQ ID NO:10, or a variant thereof comprising at least 80% identity to SEQ ID NO:10 (e.g., at least 85%, at least 90%, at least 95% or at least 98% identity to SEQ ID NO:10). In one embodiment, said antibody binds MLP (SEQ ID NO:1 or SEQ ID NO:4) with a $K_D$ of 10 nM or less.

In another aspect, the invention provides an isolated monoclonal antibody that binds to human MLP (SEQ ID NO:1 or SEQ ID NO:4), wherein the antibody, numbered according to Kabat, comprises: I) a) a heavy chain variable region comprising: i) a heavy chain CDR-H1 comprising the amino acid sequence from 31-35 of SEQ ID NO:8; and ii) a heavy chain CDR-H2 comprising the amino acid sequence from 50-66 of SEQ ID NO:8; and iii) a heavy chain CDR-H3 comprising the amino acid sequence from 95-102 of SEQ ID NO:8; and b) a light chain variable region comprising: i) a light chain CDR-L1 comprising the amino acid sequence from 24-34 of SEQ ID NO:11; and ii) a light chain CDR-L2 comprising the amino acid sequence from 50-56 of SEQ ID NO:11; and iii) a light chain CDR-L3 comprising the amino acid sequence from 89-97 of SEQ ID NO:11; or II) a variant thereof that is otherwise identical to said variable domains, except for up to a combined total of 1, 2, 3, 4, 5, 6, 7, 8, 9, or 10 amino acid substitutions within said CDR regions of said heavy chain variable region and up to a combined total of 1, 2, 3, 4, 5, 6, 7, 8, 9, or 10 amino acid substitutions within said CDR regions of said light chain variable region, wherein the antibody or variant thereof binds to human MLP (SEQ ID NO:1 or SEQ ID NO:4). In one embodiment, said variant comprises an amino acid substitution at one or more positions selected from the group consisting of position 28, 37, 57, 58, 68, 72, 82A or 102 of said heavy chain variable region, numbered according to Kabat. In one embodiment, said variant comprises an amino acid substitution at one or more positions selected from the group consisting of position 27E, 80 or 100 of said light chain variable region, numbered according to Kabat.

In one embodiment, the heavy chain of said antibody comprises SEQ ID NO:8, or a variant thereof comprising at least 80% identity to SEQ ID NO:8 (e.g., at least 85%, at least 90%, at least 95% or at least 98% identity to SEQ ID NO:8). In one embodiment, the light chain of said antibody comprises SEQ ID NO:11, or a variant thereof comprising at least 80% identity to SEQ ID NO:11 (e.g., at least 85%, at least 90%, at least 95% or at least 98% identity to SEQ ID NO:11). In one embodiment, said antibody binds MLP (SEQ ID NO:1 or SEQ ID NO:4) with a $K_D$ of 10 nM or less.

In one embodiment, said anti-MLP antibody, or antigen binding fragment thereof, comprises (i) a heavy chain variable region comprising CDR-H1 (SEQ ID NO:13), CDR-H2 (SEQ ID NO:14) and CDR-H3 (SEQ ID NO:15 or SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof.

In one embodiment, said anti-MLP antibody or antigen binding fragment thereof comprises (i) a heavy chain variable region comprising CDR-H1 (SEQ ID NO:13), CDR-H2 (SEQ ID NO:16) and CDR-H3 (SEQ ID NO:15 or SEQ ID NO:35 or SEQ ID NO:36) and (ii) a light chain variable region comprising CDR-L1 (SEQ ID NO:24), CDR-L2 (SEQ ID NO:22) and CDR-L3 (SEQ ID NO:23), and conservative modifications thereof.

In one embodiment, said anti-MLP antibody, or antigen binding fragment thereof comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

In one embodiment of any aspect of the invention disclosed herein, said antibody is an antibody fragment selected from the group consisting of Fv, Fab, Fab', F(ab)$_2$ and F(ab')$_2$. In one embodiment, said antibody is a single chain molecule. In one embodiment, said antibody is an IgG2 molecule. In one embodiment, said antibody is an IgG1 molecule. In one embodiment, said antibody is an IgG4 molecule. In one embodiment, said antibody is a humanized, chimeric or fully human antibody.

In some embodiments, said antibody or antigen binding fragment thereof specifically recognizes at least part of an epitope recognized by at least one of (i) a reference antibody comprising a heavy chain variable region as set forth in SEQ ID NO:7 and a light chain variable region as set forth in SEQ ID NO:10, such as reference antibody clone 11; or (ii) a reference antibody comprising a heavy chain variable region as set forth in SEQ ID NO:8 and a light chain variable region as set forth in SEQ ID NO:11, such as reference antibody clone B; or (iii) a reference antibody comprising a heavy chain variable region as set forth in SEQ ID NO:9 and a light chain variable region as set forth in SEQ ID NO:12, such as reference antibody clone C (see Table 1).

In accordance with the foregoing, an antibody or antigen-binding fragment thereof according to certain preferred embodiments of the present application may be one that competes for binding to human MLP (SEQ ID NO:1 or SEQ ID NO:4) with any antibody described herein. In some embodiments, the subject antibody both (i) specifically binds to the antigen and (ii) comprises a VH and/or VL domain disclosed herein, or comprises a CDR-H3 disclosed herein, or a variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope. Thus, there is presently provided a specific antibody or antigen-binding fragment thereof, comprising an antibody antigen-binding site which competes with an antibody described herein that binds to human MLP (SEQ ID NO:1 or SEQ ID NO:4), such as any one of clone 11, clone B or clone C as set forth in TABLE 1, for binding to human MLP (SEQ ID NO:1 or SEQ ID NO:4).

Binding Affinity of Anti-MLP Antibodies

The anti-MLP antibodies of the invention bind to human MLP (SEQ ID NO:1 or SEQ ID NO:4) with a $K_D$ (dissociation constant) of less than about 100 nM, or less than about 50 nM, or less than about 25 nM, or less than about 10 nM, or less than about 5 nM, or less than or equal to about 1 nM, or less than or equal to 0.1 nM. The binding affinity of the anti-MLP antibodies can be determined using a suitable binding assay known in the art, such as an ELISA assay, as described in Examples 1-3 herein.

Variant Anti-MLP Antibodies

The above-described monoclonal antibodies may be modified to provide variant antibodies that specifically bind to human MLP. The variant antibodies may be made by substituting, adding, or deleting at least one amino acid of an above-described monoclonal antibody. In general, these variant antibodies have the general characteristics of the above-described antibodies and contain at least the CDRs of an above-described antibody, or, in certain embodiments, CDRs that are very similar to the CDRs of an above-described antibody.

In the preferred embodiment, the variant comprises one or more amino acid substitution(s) in one or more hypervariable region(s) of the parent antibody. For example, the variant may comprise at least one, e.g., from about one to about ten, such as at least 1, at least 2, at least 3, at least 4, at least 5, at least 6, at least 7, at least 8, at least 9 or at least 10 substitutions, and preferably from about two to about six, substitutions in one or more CDR regions of the parent antibody. In one embodiment, said variant comprises an amino acid substitution at one or more positions selected from the group consisting of position 28, 37, 57, 58, 68, 72, 82A or 102 of said heavy chain variable region, numbered according to Kabat. In one embodiment, said variant comprises an amino acid substitution at one or more positions selected from the group consisting of position 27E, 80 or 100 of said light chain variable region, numbered according to Kabat.

In some embodiments, the variant antibodies have an amino acid sequence that is otherwise identical to the variable domain of a subject antibody set forth in TABLE 1, except for up to a combined total of 1, 2, 3, 4, 5 or 6 amino acid substitutions within said CDR regions of said heavy chain variable region and/or up to a combined total of 1, 2, 3, 4, 5 or 6 amino acid substitutions within said CDR regions of said light chain variable region, wherein the antibody or variant thereof specifically binds to human MLP (SEQ ID NO:1 or SEQ ID NO:4).

Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%, or at least 96%, or at least 97%, or at least 98%, or at least 99% identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence (such as, for example, signal peptide sequences, linker sequences, or tags, such as HIS tags) shall be construed as affecting sequence identity or homology. The variant retains the ability to bind human MLP (SEQ ID NO:1 or SEQ ID NO:4 or SEQ ID NO:5 or SEQ ID NO:6) and preferably has properties which are superior to those of the parent antibody. For example, the variant may have a stronger binding affinity for binding to MLP (SEQ ID NO:1 or SEQ ID NO:4 or SEQ ID NO:5 or SEQ ID NO:6).

To analyze such properties, one can compare a Fab form of the variant to a Fab form of the parent antibody or a full-length form of the variant to a full-length form of the parent antibody. The variant antibody of particular interest herein is one which displays at least about 10-fold, preferably at least about 20-fold, and most preferably at least about 50-fold, enhancement in binding affinity when compared to the parent antibody.

The antibodies of the invention may be modified to enhance desirable properties, such as it may be desirable to control serum half-life of the antibody. In general, complete antibody molecules have a very long serum persistence, whereas fragments (<60-80 kDa) are filtered very rapidly through the kidney. Hence, if long-term action of the antibody is desirable, the antibody is preferably a complete full length IgG antibody (such as IgG2 or IgG4), whereas if shorter action of the antibody is desirable, an antibody fragment may be preferred.

Hybridomas Producing Anti-MLP Monoclonal Antibodies (Clones 11, B and C)

The hybridoma cell line designated "Hybridoma MLP Clone 11" was deposited with the American Type Culture Collection ("ATCC," Manassas, Va., USA) on Oct. 30, 2014, under the terms of the Budapest Treaty. The ATCC accorded the Hybridoma MLP Clone 11 the ATCC Designation Number: PTA-121699. This cell line is a mouse hybridoma cell line derived from mouse spleen cells and secretes a monoclonal antibody, which is herein referred to as "αMLP Clone 11."

The hybridoma cell line designated "Hybridoma MLP clone B" was deposited with the American Type Culture Collection ("ATCC", Manassas, Va., USA) on Oct. 30, 2014, under the terms of the Budapest Treaty. The ATCC accorded the Hybridoma MLP Clone B the ATCC Designation Number PTA-121700. This cell line is a mouse hybridoma cell line derived from mouse spleen cells and secretes a monoclonal antibody, which is herein referred to as "αMLP Clone B."

The hybridoma cell line designated "Hybridoma MLP clone C" was deposited with the American Type Culture Collection ("ATCC", Manassas, Va., USA) on Oct. 30, 2014, under the terms of the Budapest Treaty. The ATCC accorded the Hybridoma MLP Clone C the ATCC Designation Number PTA-121701. This cell line is a mouse hybridoma cell line derived from mouse spleen cells and secretes a monoclonal antibody, which is herein referred to as "αMLP Clone C."

Accordingly, in one embodiment, the invention provides an isolated anti-MLP monoclonal antibody produced by a hybridoma cell line selected from the group of hybridoma cell lines deposited under the ATCC Designation Numbers PTA-121699, PTA-121700 and PTA-121701.

In another embodiment, the present invention provides a hybridoma cell line selected from the group consisting of the hybridoma cell line secreting αMLP Clone 11, the hybridoma cell line secreting αMLP Clone B and the hybridoma cell line secreting αMLP Clone C.

Single-Chain Anti-MLP Antibodies

In one embodiment of the present invention, the anti-MLP antibody is a single-chain antibody, defined as a genetically engineered molecule containing the variable region of the light chain, the variable region of the heavy chain, linked by a suitable polypeptide linker as a genetically fused single-chain molecule. Such single-chain antibodies are also referred to as "single-chain Fv" or "scFv" antibody fragments. Generally, the Fv polypeptide further comprises a polypeptide linker between the VH and VL domains that enables the scFv to form the desired structure for antigen binding. The scFv antibodies that bind MLP can be oriented with the variable light region either amino terminal to the variable heavy region or carboxyl terminal to it.

Humanized Anti-MLP Antibodies

The anti-MLP antibodies can be modified without changing their ability to be used for the purposes described herein. As an initial matter, it is noted that the antibodies described herein originated from mice immunized with recombinant C-terminal MLP (SEQ ID NO:4). The antibodies thus have framework regions (regions outside the complementarity determining regions, or "CDRs") which contain the amino acid residues usually found in the framework regions in murine antibodies, and which may be immunogenic when administered to a human patient. To reduce immunogenicity of murine antibodies when used in humans, it is common in the art to engineer the framework regions by replacing residues found at particular positions in the antibodies of mice with the residues more typically found at the same position in human antibodies. Antibodies engineered in these ways are referred to as "humanized antibodies" and are typically preferred for in vivo use, since they have a lower risk of inducing side effects and typically can remain in the circulation longer. Methods of humanizing antibodies are known in the art and are set forth in detail in, for example, U.S. Pat. Nos. 6,180,377; 6,407,213; 5,693,762; 5,585,089; and 5,530,101.

Further, since the CDRs of the variable regions determine antibody specificity, the CDRs set forth in Tables 2A-G, Table 3, Tables 4A-F, and Table 5 can be grafted or engineered into an antibody of choice to confer specificity for binding to MLP upon that antibody. For example, the CDRs from clones 11, B and C can be grafted onto a human antibody framework of known three dimensional structure (see e.g., WO98/45322; Jones et al., *Nature* 321:522 (1986); Verhoeyen et al., *Science* 239:1534 (1988); Riechmann et al., *Nature* 332:323 (1988) and Winter & Milstein, *Nature* 349:293 (1991) to generate an anti-MLP antibody with reduced or no immunogenic responses when administered to humans.

Methods for Producing Anti-MLP Antibodies

In another aspect, the present invention provides a method of producing an antibody specifically recognizing and binding an epitope within the full-length human MLP polypeptide (SEQ ID NO:1), such as within the C-terminal portion of human MLP (SEQ ID NO:4), such as an epitope in the C-terminal region of human MLP set forth as SEQ ID NO:5 (i.e., amino acids 397-431 of SEQ ID NO:1); or such as an epitope in the C-terminal region of human MLP set forth as SEQ ID NO:6 (i.e, amino acids 403-431 of SEQ ID NO:1) said method comprising administering to a mammal a polypeptide comprising or consisting of SEQ ID NO:1, or a portion thereof, such as a polypeptide comprising or consisting of SEQ ID NO:4, or such as a polypeptide comprising or consisting of SEQ ID NO:5, or such as a polypeptide comprising or consisting of SEQ ID NO:6 and selecting antibodies recognizing human MLP.

In many embodiments, the nucleic acids encoding a subject monoclonal antibody are introduced directly into a host cell, and the cell incubated under conditions sufficient to induce expression of the encoded antibody.

In some embodiments, the invention provides a nucleic acid molecule encoding an anti-MLP antibody, or fragment thereof, of the invention, such as an antibody or fragment thereof set forth in TABLE 1. In some embodiments the invention provides a nucleic acid molecule comprising a nucleic acid sequence selected from the group consisting of SEQ ID NO:29, SEQ ID NO:30, SEQ ID NO:31, SEQ ID NO:32, SEQ ID NO:33 and SEQ ID NO:34.

In some embodiments, the invention provides a cell comprising a nucleic acid molecule encoding an MLP-specific monoclonal antibody of the invention.

In some embodiments, the invention provides an expression cassette comprising a nucleic acid molecule encoding an MLP-specific monoclonal antibody of the invention.

In some embodiments, the invention provides a method of producing MLP-specific monoclonal antibodies comprising culturing a cell comprising a nucleic acid molecule encoding an MLP-specific antibody of the invention.

In one embodiment, the method of producing an antibody specifically recognizing an epitope within the C-terminal portion of human MLP comprises culturing a hybridoma cell line selected from the group consisting of a hybridoma cell line secreting αMLP Clone 11, a hybridoma cell line secreting αMLP Clone B and a hybridoma cell line secreting αMLP Clone C.

According to certain related embodiments there is provided a recombinant host cell which comprises one or more constructs as described herein; a nucleic acid encoding any anti-MLP antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

For example, any cell suitable for expression of expression cassettes may be used as a host cell, for example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al., *J. Gen Virol.* 36:59 (1977)); baby hamster kidney cells (BHK, ATCC CCL 10); Chinese hamster ovary-cells (CHO, Urlaub and Chasin, *Proc. Natl. Acad. Sci. (USA)* 77:4216, (1980); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., *Annals N.Y. Acad. Sci* 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e., in vitro, ex vivo, or in vivo). A general discussion of these methods can be found in Ausubel, et al., *Short Protocols in Molecular Biology*, 3d ed., Wiley & Sons, 1995. In some embodiments, lipofectamine and calcium mediated gene transfer technologies are used.

After the subject nucleic acids have been introduced into a cell, the cell is typically incubated, normally at 37° C., sometimes under selection, for a suitable time to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). The efficiency of expression may be enhanced by the inclusion of appropriate transcription enhancer elements, transcription terminators, etc. (see Bittner et al., *Methods in Enzymol.* 153:51-544 (1987)).

For long-term, high-yield production of recombinant antibodies, stable expression may be used. For example, cell lines, which stably express the antibody molecule, may be engineered. Rather than using expression vectors, which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci, which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium. For example, a nucleic acid sequence encoding a signal peptide may be included adjacent the coding region of the antibody or fragment. Such a signal peptide may be incorporated adjacent to the 5' end of the amino acid sequences set forth herein for the subject antibodies in order to facilitate production of the subject antibodies.

Anti-MLP Antibodies Labeled with a Detectable Moiety

In another aspect, the invention provides anti-MLP antibodies labeled with a detectable moiety (i.e., a moiety that permits detection and/or quantitation), which can be used for diagnostic applications. As used herein "a detectable moiety" is a moiety detectable by spectroscopic, photochemical, biochemical, immunochemical, chemical and/or other physical means. A detectable moiety may be coupled either directly and/or indirectly (for example via a covalent linkage by chemical or recombinant means) to antibodies and antigen binding fragments thereof of the present invention using methods well known in the art. These labeled anti-MLP antibodies can be used, for example, in in-vitro assays to detect the presence of MLP in a biological sample or in in vivo assays (e.g., imaging) to detect the presence of MLP-expressing cells in a living body.

Numerous labels are available which can be generally grouped into the following categories:

(a) Radioisotopes, such as $^{35}S$, $^{14}C$, $^{125}I$, $^{3}H$, and $^{131}I$. The anti-MLP antibody can be labeled with the radioisotope using the techniques described in *Current Protocols in Immunology*, Volumes 1 and 2, Gutigen et al., Ed., Wiley-Interscience. New York, N.Y. Pubs., (1991) for example and radioactivity can be measured using scintillation counting. Radioisotopes may be bound to antibody either directly or indirectly by using an intermediary functional group. Useful intermediary functional groups include chelators such as ethylenediaminetetraacetic acid and diethylenetriaminepentaacetic acid. For example, see Shih et al., Int J Cancer 46: 1101 (1990) and U.S. Pat. No. 5,057,313. The subject anti-MLP antibodies, and antibody fragments also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. The subject anti-MLP antibodies and fragments thereof can also be conjugated to ultrasound contrast/enhancing agents. For example, one ultrasound contrast agent is a liposome.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra for example. Fluorescence can be quantified using a fluorimeter.

(c) Various enzyme-substrate labels are available. The enzyme generally catalyses a chemical alteration of the chromogenic substrate, which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g, firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. 0-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzyme (ed Langone & H. Van Vunakis), Academic Press, New York, 73: 147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or the fluorogenic substrate 4-methylumbelliferyl-β-D-galactosidase.

Numerous other enzyme-substrate combinations are available to those skilled in the art.

In some embodiments, the label is indirectly conjugated with the anti-MLP antibody. The skilled artisan will be aware of various techniques for achieving this. For example, the anti-MLP antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the anti-MLP antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment, the anti-MLP antibody is not labeled (i.e., is naked), and the presence thereof can be detected using a labeled antibody which binds to the anti-MLP antibody.

Anti-MLP Antibodies Coupled to a Therapeutic Agent

In another aspect, the invention provides anti-MLP antibodies coupled to a therapeutic agent, which can be used in vivo to target therapeutic molecules to MLP expressing cells. For example, an immunoconjugate comprising an anti-MLP antibody and a therapeutic moiety can be used to inhibit the growth and proliferation of cancer cells bearing the MLP antigen. As used herein, the term "therapeutic agent" is a compound, molecule or atom which is administered separately, concurrently or sequentially with an antibody moiety or conjugated to an antibody moiety, i.e., antibody or antibody fragment, or a subfragment, and is useful in the treatment of a subject suffering from a pathological condition, such as, for example, an epithelial cancer. Examples of therapeutic agents include antibodies, antibody fragments, cytotoxic agents, drugs, toxins, nucleases, hormones, immunomodulators, anti-angiogenic agents, boron compounds, photoactive agents or dyes, radioisotopes, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, antiangiogenic and apoptotic agents, particularly doxorubicin, methotrexate, taxol, CPT-11, camptothecans, proteosome inhibitors, mTOR inhibitors, HDAC inhibitors, tyrosine kinase inhibitors, and others from these and other classes of anticancer agents. Other useful cancer chemotherapeutic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins and hormones. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Any of the anti-MLP antibodies, antibody fragments and fusion proteins disclosed herein can be conjugated with one or more therapeutic agents, using a variety of techniques known in the art. One or more therapeutic or diagnostic agents (e.g., a detectable moiety) may be attached to each antibody, antibody fragment or fusion protein, for example by conjugating an agent to a carbohydrate moiety in the Fc region of the antibody. If the Fc region is absent (for example with certain antibody fragments), it is possible to introduce a carbohydrate moiety into the light chain variable region of either an antibody or antibody fragment to which a therapeutic or diagnostic agent may be attached. See, for example, Leung et al., *J Immunol.* 154: 5919 (1995); Hansen et al., U.S. Pat. No. 5,443,953 (1995), Leung et al., U.S. Pat. No. 6,254,868, the Examples section of each patent incorporated herein by reference.

Methods for conjugating peptides to antibody components via an antibody carbohydrate moiety are well-known to those of skill in the art. See, for example, Shih et al., *Int J Cancer* 41: 832 (1988); Shih et al., *Int J Cancer* 46: 1101 (1990); and Shih et al., U.S. Pat. No. 5,057,313, the Examples section of which is incorporated herein by reference. The general method involves reacting an antibody component having an oxidized carbohydrate portion with a carrier polymer that has at least one free amine function and that is loaded with a plurality of therapeutic agents, such as peptides or drugs. This reaction results in an initial Schiff base (imine) linkage, which can be stabilized by reduction to a secondary amine to form the final conjugate.

As another example, a therapeutic or diagnostic agent can be attached at the hinge region of a reduced antibody component via disulfide bond formation. As an alternative, such agents can be attached to the antibody component using a heterobifunctional cross-linker, such as N-succinyl 3-(2-pyridyldithio)proprionate (SPDP). Yu et al., *Int. J. Cancer* 56: 244 (1994). General techniques for such conjugation are well-known in the art. See, for example, Wong, *Chemistry of Protein Conjugation and Cross-linking* (CRC Press 1991); Upeslacis et al., "Modification of Antibodies by Chemical Methods," in *Monoclonal Antibodies: Principles and Applications*, Birch et al. (eds.), pages 187-230 (Wiley-Liss, Inc. 1995); Price, "Production and Characterization of Synthetic Peptide-Derived Antibodies," in *Monoclonal Antibodies: Production, Engineering and Clinical Application*, Ritter et al. (eds.), pages 60-84 (Cambridge University Press 1995).

V. Methods of Detecting Epithelial Cancer (e.g., Ovarian and/or Pancreatic Cancer) Using Anti-MLP Antibodies As described herein, the inventors have generated anti-MLP antibodies that are suitable for use in a diagnostic assay for detecting early stage epithelial cancer (e.g., ovarian and/or pancreatic cancer). A brief overview of ovarian cancer tumor types, risk factors, diagnosis and classification is provided below.

1. Overview of Ovarian Cancer Tumor Types, Risk Factors, Diagnosis and Classification Ovarian Tumor Types Ovarian tumors are divided into benign tumors and malignant tumors. The benign tumor is an abnormal cell growth, stays local and does not spread to other organs in the body. There are usually no symptoms. However, the second type of the tumor is cancerous (malignant) and is able to metastasize to other parts of the body. Ovarian tumors are classified histopathologically according to their cellular origin into epithelial, stroma and germ cell tumors as shown below in Table 6.

TABLE 6

Ovarian Tumor Types

| Type of ovarian tumor | % Incidence | Female age groups |
|---|---|---|
| Epithelial ovarian tumors | 90% | After menopause |
| Germ cell tumors | 3% | Young girl |
| Stromal tumors | 6% | No specific ages |

Table 6. The incidence of different types of ovarian tumors and the age groups affected. Metastatic tumors 1% (ovary has tumors) due to secondary metastases to other parts of the body such as stomach, colon and breast (Chauhan et al., Jour Ovarian Res 2: 212-215, 2009).

Epithelial tumors constitute 90% of all ovarian tumors (Chauhan et al., *Jour Ovarian Res* 2:212-215, 2009; Nguyen et al., *Women's Health*, 9: 171-187, 2013). Most epithelial tumors are benign tumors, for example, serous adenomas and Brenner tumors. Malignant epithelial tumors are a real threat to patients in around 90% of cases because they are diagnosed at the late stages. The incidence of these tumors is great after menopause (Chauhan et al., *Jour Ovarian Res* 2:212-215, 2009; Nguyen et al., *Women's Health*, 9: 171-187, 2013. Some epithelial ovarian tumors may appear with low malignant potential (LMP tumors), which are tumors with slow growth and low spreading rate. These LMP tumors are also known as borderline epithelial ovarian cancers as this type of tumor is not clearly visible under the microscope (Altchek et al., Diagnosis and Management of Ovarian Disorders, $2^{nd}$ edition, San Diego Calif., Academic Press, 2003).

Germ cells are located in the ovary responsible for the producing the egg. Germ cell tumors arise from the germinal cells and they constitute about 3% of all ovarian tumors (Chauhan et al., *Jour Ovarian Res* 2:212-215, 2009). Mostly they are benign rather than malignant. The incidence of these tumors is greater in young females. Examples include, mature teratomas and endodermal sinus (Altchek et al., Diagnosis and Management of Ovarian Disorders, $2^{nd}$ Edition, San Diego Calif., Academic Press, 2003).

Stromal cell tumors originate from connective tissue that hold the ovaries together and these cells also have the function of producing hormones such as progesterone and estrogen (Altchek et al., Diagnosis and Management of Ovarian Disorders, 2$^{nd}$ edition, San Diego Calif., Academic Press, 2003). These tumors constitute 6% of all ovarian tumors (Chauhan et al., Jour Ovarian Res 2:212-215, 2009). They affect both young and post-menopausal age groups and include granulose theca tumor and granulose cell tumors (Altechek et al., 2003).

Risk Factors for Ovarian Cancer

Risk factors for ovarian cancer include endometriosis (Modugno et al., American J of Obstetrics and Gynecology 191:733-740, 2004), ovarian cysts (Alteck et al., 2003), age (post-menopause, with increased risk for women age 65 years or older (Yancik et al., Cancer 71:517-523, 1993; Guppy et al., 2005), smoking (Jordan et al., Gynecologic Oncology 103:1122-1129, 2006), and obesity (McLemore et al., Cancer Nursing 32:281, 2009). Also, mutations in breast cancer type 1 (BRCA1) located on chromosome 17q and/or mutations in breast cancer type 2 (BRCA2) located on chromosome 13q are regarded as high risk factors for breast and ovarian cancers (Nguyen et al., Women's Health, 9: 171-187, 2013).

Diagnosis and Classification of Ovarian Cancer

Early diagnosis of ovarian cancer is difficult because the first symptoms of ovarian cancer are non-localized mild pain. The symptoms of ovarian malignancies become clearer in the later stages and include loss of appetite and weight loss, pain in the back and pelvis, vaginal bleeding after menopause, frequent urination, constipation or diarrhea and bloating in the abdomen (American Cancer Society, How is Ovarian Cancer Diagnosed, http:cancer.org/cancer/ovarian-cancer/detailedguide/ovarian-cancer-diagnosis, accessed on Apr. 22, 2013).

Ovarian cancer is diagnosed based on the presence of a tumor as determined by physical examination of the pelvis, medical imaging (i.e., ultrasound, computerized tomography scan (CT scan), magnetic resonance imaging (MRI), and blood test to measure various biomarkers that have been associated with late stage ovarian cancer (i.e., CA-125, IL-6, IL-8, serum amyloid A (SAA) and C-reactive protein (CRP). For example, OvPlex™ is a commercially available ELISA kit that uses a combination of the above-listed markers for the detection of ovarian cancer in symptomatic women that have already undergone surgery to remove primary ovarian tumors. OvPlex™ is not an early detection kit for ovarian cancer since the inflammatory markers IL-6, IL-8 and the liver acute phase markers SAA and CRP require a strong stimulus to be raised to detectable levels (see Healthlinx, O., What is the OvPlex™ Diagnostic, http:healthlinx.com.au/ovplex-tm, accessed on Apr. 8, 2013).

Biomarkers Other than MLP that have been Studied for Early Detection of Ovarian Cancer Many studies have been carried out to identify biomarkers for the early detection of ovarian malignances (Costa et al., Clinics 64:641-644, 2009). Table 7 summarizes the status of several biomarkers that have been studied for early detection of ovarian cancer. In contrast to the mucin biomarker CA-125, MLP expression is absent in normal tissues and benign tumors.

TABLE 7

Previous Studies with Biomarkers to Detect Early Stage Ovarian Tumors

| Biomarker | Sensitivity | Specificity | References |
|---|---|---|---|
| CA-125 | 50%-60% | 90% | Kim et al., PLoS One 7, e44960, 2012; Su et al., Clinica ChimicaActa, 2012 |
| HE4 | 72% | 95% | Rossing et al., Cancer Causes and Control: CCC 19: 1357-1364, 2008 |
| HE4 PLUS CA-125 | 76% | 95.7% | Moore et al., International Journal of Gynecological Cancer 21(7): 1185-1190, 2011 |
| Mesothelin | 60% | 98% | Nguyen et al., Women's Health 9: 171-187, 2013 |
| Mesothelin and CA-125 | 12% in serum 42% in urine | 95% in serum 95 in urine | Nguyen et al., Women's Health 9: 171-187, 2013; Sarojini et al., Journal of Oncology, 2012 |
| Kallikreins | 21%-26% | 95% | Nguyen et al., Women's Health 9: 171-187, 2013; Sarojini et al., Journal of Oncology, 2012 |
| Kallikreins plus AC-125 | 42% | 90% | Diamandis et al., Journal of Clinical Oncology 21: 1035-1043, 2003 |
| Osteopontin | 93.8% | 33% | Jordan et al., Gynecologic Oncology 103: 1122-1129, 2006 |
| B7-H4 | 45% | 97% | Singh I., Anatomy and Physiology for Physiotherpists, Anshan, 2006 |
| B7-H4 combined with AC_125 | 65% | 97% | Singh I., Anatomy and Physiology for Physiotherpists, Anshan, 2006 |

Classification

There are four stages of ovarian cancer. Stage I includes cancer that is limited within the ovary. It can occur in one or both ovaries. Ovarian cancer is given stage II when cancer growth involves one or both ovaries with extension or metastasis to the pelvis. In the third and fourth stages there is extension of the disease beyond the pelvis, which includes intra-abdominal to lymph node in the case of stage III or distant metastasis past the abdominal cavity in the case of stage IV (Chauhan et al., Jour Ovarian Res 2:212-215, 2009; Guppy et al., Clinical Oncology 17:339-411, 2005).

If ovarian cancer is diagnosed in the early stage (stage I), the five-year survival rate ranges from 60% to 90%, whereas if diagnosed in stage II the five year survival rate decreases to a range from 37% to 66%. Ovarian cancer patients diagnosed in stage III have a five year survival rate in the range of 5% to 50% and those diagnosed in stage IV have a five year survival rate between 0%-17% (Stimpfl et al., *Cancer Letters* 145:133-141, 1999).

Treatment

The standard treatment of ovarian cancer is by surgical removal of the ovary, followed by chemotherapy, which is typically a combination of platinum-based drugs and paclitaxel (see Cohen et al., *Jour of Molecular Medicine*, 91(3): 357-368, 2013). Radiotherapy is used in cases where cancer cells and metastases are missed during surgical removal (Sornsukolrat et al., *Chotmaihet Thangphaet* 95:1141-1148, 2012). The tumor volume at the diagnosis is also a crucial prognostic factor in determining the efficacy of surgery for both primary and secondary tumors with regard to the progression of free intervals and of prolonged survival (Weidner et al., *Modern Surgical Pathology* 2, Saunders/Elsevier, 2009).

2. In Vitro Assays for the Presence of the MLP Antigen as a Biomarker for the Presence of Epithelial Cancer (e.g., Ovarian Cancer or Pancreatic Cancer)

In one aspect, the anti-MLP antibodies of the present invention are used in an in vitro immunoassay for screening a biological sample obtained from a test subject for the presence of the MLP antigen, wherein the presence of MLP, or an increased amount of MLP as compared to a control from a healthy subject, or reference standard, indicates the subject has, or is at an increased risk of developing an epithelial cancer (e.g., ovarian or pancreatic cancer). The test subject can be an apparently healthy subject, or a subject at risk for developing an epithelial cancer, or a subject suspected of having early stage epithelial cancer, or a subject suffering from an epithelial cancer such as ovarian, pancreatic, colorectal, breast, appendiceal, lung, renal, cervical, biliary, esophageal, epithelial skin and/or other mucin-secreting types of cancer. In such in vitro immunoassays, the anti-MLP antibody, or antigen-binding fragment thereof, may be naked or may be labeled with a detectable moiety, as described herein, and may be utilized in liquid phase or bound to a substrate, as described below. For purposes of in vitro assays, any type of antibody such as murine, chimeric, humanized or human may be utilized, since there is no host immune response to consider.

The antibodies of the present disclosure may be employed in any known diagnostic immunoassay method, such as a competitive binding assay, a direct or indirect sandwich assay, and an immunoprecipitation assay (see e.g., Zola, Monoclonal Antibodies: A Manual of Techniques, pp. 147-158 (CRC Press. Inc., 1987).

Competitive binding assays rely on the ability of a labeled standard to compete with the test sample analyte for binding with a limited amount of antibody. The amount of MLP in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte that remain unbound.

Sandwich assays, involve the use of two antibodies, each capable of binding to a different immunogenic portion, or epitope, of the protein to be detected (e.g., MLP). In a sandwich assay, the test sample analyte is bound by a first antibody (e.g., an anti-MLP antibody), which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

In one embodiment, the anti-MLP antibodies of the invention are used to detect the presence of the MLP antigen in a biological sample using an enzyme-linked immunosorbent assay (ELISA) (see e.g., Gold et al. *J Clin Oncol.* 24:252-58, 2006).

In the direct competitive ELISA, a pure or semipure antigen preparation is bound to a substrate that is insoluble in the fluid or cellular extract being tested and a quantity of detectably labeled soluble antibody is added to permit detection and/or quantitation of the binary complex formed between substrate-bound antigen and labeled antibody.

In contrast, a "double-determinant" ELISA, also known as a "two-site ELISA" or "sandwich assay," requires small amounts of antigen and the assay does not require extensive purification of the antigen. Thus, the double-determinant ELISA is preferred to the direct competitive ELISA for the detection of an antigen in a clinical sample. See, for example, the use of the double-determinant ELISA for quantitation of the c-myc oncoprotein in biopsy specimens. Field et al., *Oncogene* 4: 1463 (1989); Spandidos et al., AntiCancer Res. 9: 821 (1989). In a double-determinant ELISA, a quantity of unlabeled monoclonal antibody or antibody fragment (the "capture antibody") is bound to a substrate (e.g., a solid support), the test sample is brought into contact with the capture antibody, and a quantity of detectably labeled soluble antibody (or antibody fragment) is added to permit detection and/or quantitation of the ternary complex formed between the capture antibody, antigen, and labeled antibody. In one embodiment, the capture antibody bound to a substrate (e.g., solid support) is an anti-MLP antibody or antigen-binding fragment thereof as disclosed herein that binds to an epitope in the C-terminal portion of MLP. Methods of performing a double-determinant ELISA are well-known by those of skill in the art. See, for example, Field et al., *Oncogene* 4: 1463 (1989); Spandidos et al., *AntiCancer Res.* 9: 821 (1989); and Moore et al., *Methods in Molecular Biology* Vol 10:273-281 (The Humana Press, Inc. 1992).

In the double-determinant ELISA, the soluble antibody or antibody fragment must bind to an MLP epitope that is distinct from the epitope recognized by the capture antibody. The double-determinant ELISA can be performed to ascertain whether the MLP antigen is present in a test biological sample, such as a body fluid (e.g., blood, plasma or serum) or a biopsy sample. Alternatively, the assay can be performed to quantitate the amount of MLP antigen that is present in a clinical sample of body fluid. The quantitative assay can be performed by including dilutions of purified MLP antigen.

In another embodiment, the anti-MLP antibodies of the invention are used to detect the presence of the MLP antigen in a test substance (e.g., a biological sample obtained from a subject) using a radioimmunoassay (RIA). For example, in one form of RIA, the test biological sample is mixed with an anti-MLP antibody in the presence of radiolabeled MLP antigen. In this method, the concentration of the test substance will be inversely proportional to the amount of labeled MLP antigen bound to the anti-MLP antibody and directly related to the amount of free, labeled MLP antigen. Other suitable screening methods will be readily apparent to those of skill in the art.

In vitro immunoassays can be performed in which at least one anti-MLP antibody or antigen-binding fragment thereof is bound to a substrate (e.g., a solid-phase carrier). For example, anti-MLP monoclonal antibodies or fragments thereof can be attached to a polymer, such as aminodextran, in order to link the monoclonal antibody to an insoluble substrate such as a polymer-coated bead, a plate, a tube, or a ceramic or metal chip. In one embodiment, the substrate is suitable for use in an ELISA method (e.g., a multiwell microtitre plate). Accordingly, the determination of the level of MLP in the sample may be determined by commercially available methods such as an ELISA based assay, chemical or enzymatic protein determination.

In one embodiment, the methods of the present disclosure use a solid-state device for determining the level of MLP in a sample isolated from the patient. The solid-state device comprises a substrate having an activated surface on to which at least one anti-MLP antibody is immobilised at discreet areas of the activated surface. Preferably, the solid state device may perform multi-analyte assays such that the level of a biomarker of interest in a sample isolated from the patient may be determined simultaneously with the level of a further biomarker of interest in the sample. In this embodiment, the solid state device has a multiplicity of discrete reaction sites each bearing a desired antibody covalently bound to the substrate, and in which the surface of the substrate between the reaction sites is inert with respect to the target biomarker. The solid-state, multi-analyte device may therefore exhibit little or no non-specific binding. For example, a solid-state device suitable for use in the methods of the present disclosure is the Biochip Array Technology system (BAT) (available from Randox Laboratories Limited).

Other suitable in vitro assays will be readily apparent to those of skill in the art. The specific concentrations of detectably labeled anti-MLP antibody and MLP antigen, the temperature and time of incubation, as well as other assay conditions may be varied, depending on various factors including the concentration of the MLP antigen in the sample, the nature of the sample, and the like. The binding activity of a sample of anti-MLP antibody may be determined according to well-known methods. Those skilled in the art will be able to determine operative and optimal assay conditions for each determination by employing routine experimentation.

In another embodiment, the subject antibodies and antigen-binding fragments thereof can be used to detect the presence of the MLP antigen in tissue sections prepared from a histological specimen (e.g., a biopsy sample). Such in situ detection can be used to determine the presence of the MLP antigen and to determine the distribution of the MLP antigen in the examined tissue. In situ detection can be accomplished by applying a detectably-labeled anti-MLP antibody to tissue sections. General techniques of in situ detection are well-known to those of ordinary skill. See, for example, Ponder, "Cell Marking Techniques and Their Application," in *Mammalian Development: A Practical Approach* 113-38 Monk (ed.) (IRL Press 1987).

The subject anti-MLP antibodies and antigen-binding fragments thereof can be labeled with any appropriate detectable moiety as described herein. Examples of suitable detectable moieties include radioisotopes, enzymes, fluorescent labels, dyes, chromogens, chemiluminescent labels, bioluminescent labels and paramagnetic labels. The above-described in vitro and in situ detection methods may be used to assist in the detection of MLP antigen in a biological sample (e.g., a serum sample), or in the diagnosis or staging of a pathological condition such as the presence of an epithelial cancer, such as ovarian, pancreatic, colorectal, breast, appendiceal, lung, renal, cervical, biliary, esophageal, epithelial skin and/or other mucin-secreting types of cancer. For example, such methods can be used to detect tumors that express the MLP antigen such as ovarian, pancreatic, colorectal, breast, appendiceal, lung, renal, cervical, biliary, esophageal, epithelial skin and/or other mucin-secreting types of cancer.

In accordance with the foregoing, in one aspect, the present invention provides a method of detecting the presence or amount of MLP in a biological sample from a test subject, the method comprising (a) contacting a biological sample from a test subject with an anti-MLP antibody or antigen-binding fragment thereof in an in vitro immunoassay and (b) detecting the presence or absence of binding of said antibody, wherein the presence of binding indicates the presence of MLP in the sample, wherein the antibody or fragment thereof binds to an epitope in the C-terminal region of MLP, set forth as SEQ ID NO:4. In one embodiment, the anti-MLP antibody is labeled with a detectable moiety and step (b) comprises detecting the presence of said detectable moiety.

In one embodiment, the method further comprises comparing the amount of MLP detected in accordance with step (b) with a reference standard or control sample from a healthy subject, wherein an increase of at least two-fold or higher (e.g., at least five-fold, or at least ten-fold, or at least 20-fold, or at least 50-fold, or at least 100-fold or higher) in the level of MLP in the test sample as compared to the control sample (or reference standard) indicates the presence of, or increased risk for developing an epithelial cancer, such as ovarian cancer or pancreatic cancer, in the test subject.

Although the details of an immunoassay may vary with the particular format employed, the method of detecting MLP in a biological sample comprises the steps of contacting the biological sample with an antibody that specifically binds to MLP. The antibody is allowed to bind to MLP in the biological sample under immunologically reactive conditions, and the presence of the bound antibody is detected directly or indirectly. The MLP-specific antibodies may be used, for example, as the capture antibody of an ELISA, or as a second antibody to bind to MLP captured by the capture antibody. As is known in the art, the presence of the second antibody is typically then detected.

A biological sample may be any sample of biological tissue or fluid obtained from a mammalian subject. Examples of biological samples include, but are not limited to, tissue from biopsy, sputum, amniotic fluid, ascites, blood or serum. In one embodiment, the biological sample is selected from the group consisting of blood, serum, plasma and tissue.

In one embodiment of the method, the anti-MLP antibody or fragment thereof is a monoclonal antibody that binds to the same epitope or competes for binding to MLP with a reference antibody selected from the group consisting of: (i) the monoclonal anti-MLP antibody Clone 11 produced by the cell line deposited at the ATCC on Oct. 30, 2014 under the ATCC Designation number PTA-121699; (ii) the monoclonal anti-MLP antibody Clone B produced by the hybridoma cell line deposited at the ATCC on Oct. 30, 2014 under the ATCC Designation number PTA-121700; and (iii) the monoclonal anti-MLP antibody Clone C produced by the hybridoma cell line deposited at the ATCC on Oct. 30, 2014 under the ATCC Designation number PTA-121701.

In one embodiment of the method, the anti-MLP antibody or fragment thereof is a monoclonal antibody having a heavy chain variable region CDR-H3 sequence comprising an amino acid sequence set forth as SEQ ID NO:15, or SEQ ID NO:35 or SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

In one embodiment, said antibody, or antigen binding fragment thereof, comprises (i) a heavy chain variable region comprising CDR-H1 (SEQ ID NO:13), CDR-H2 (SEQ ID NO:14) and CDR-H3 (SEQ ID NO:15 or SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof. In one embodiment, said antibody or antigen binding fragment thereof comprises (i) a heavy chain variable region comprising CDR-H1 (SEQ ID NO:13), CDR-H2 (SEQ ID NO:16) and CDR-H3 (SEQ ID NO: 15 or SEQ ID NO:35 or SEQ ID NO:36) and (ii) a light chain variable region comprising CDR-L1 (SEQ ID NO:24), CDR-L2 (SEQ ID NO:22) and CDR-L3 (SEQ ID NO:23), and conservative modifications thereof. In one embodiment, said antibody, or antigen binding fragment thereof comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

In one embodiment, the anti-MLP antibody or fragment thereof is a monoclonal antibody that comprises a heavy chain variable region and/or a light chain variable region set forth in Table 1, and conservative sequence modifications thereof.

In one embodiment, the anti-MLP antibody or fragment thereof is a monoclonal anti-MLP antibody produced by the hybridoma cell line secreting αMLP Clone 11 deposited at the ATCC on Oct. 30, 2014 under the ATCC Designation number PTA-121699. In one embodiment, the anti-MLP antibody or fragment thereof is a monoclonal antibody produced by the hybridoma cell line secreting αMLP Clone B deposited at the ATCC on Oct. 30, 2014 under the ATCC Designation number PTA-121700. In one embodiment, the anti-MLP antibody or fragment thereof is a monoclonal antibody produced by the hybridoma cell line secreting αMLP Clone C deposited at the ATCC on Oct. 30, 2014 under the ATCC Designation number PTA-121701.

In one embodiment, the method further comprises performing an immunoassay with one or more additional antibodies that bind to ovarian and/or pancreatic cancer biomarkers, such as the biomarkers shown in Table 7 (e.g., CA-125, HE4, Mesothelin, Kallikreins, Osteopontin, and B7-H4). Additional biomarkers for all stages of ovarian cancer include: CRP, EGF-R, CA-19-9, Apo-A1, Apo-CIII, IL-6, IL-18, MIP-1a, Tenascin C, Myoglobin, vWF, Haptoglobin, IL-10, IGF-I, IGF-II, Prolactin, ACE, ASP, Resistin and Carcinoembryonic antigen (CEA).

In one embodiment, the test subject is apparently healthy.

In one embodiment, the test subject has a family history of ovarian or pancreatic cancer.

In one embodiment, the test subject is experiencing one or more symptoms associated with ovarian cancer. For example, symptoms associated with ovarian cancer in a human female subject include one or more of the following: pelvic mass, ascites, abdominal distention, abdominal pressure, swelling or bloating, pelvic pain or discomfort, nausea, constipation, gas, indigestion, diarrhea, urinary problems with as frequent urination or urgent need to urinate, loss of appetite or a quick feeling of fullness; increased abdominal circumference or tight-fitting clothing, persistent lack of energy, weight gain or loss with no known reason, abnormal bleeding from the vagina and low back pain.

In one embodiment, the test subject is known to be suffering from ovarian, pancreatic, colorectal, breast, appendiceal, lung, renal, cervical, biliary, esophageal, epithelial skin and/or other mucin-secreting types of cancer and has had or is currently undergoing treatment for ovarian, pancreatic, colorectal, breast, appendiceal, lung, renal, cervical, biliary, esophageal, epithelial skin and/or other mucin-secreting types of cancer. In one embodiment, more than one sample is obtained from a particular test subject at more than one point in time. In one embodiment, the method further comprises comparing the results of the assay at one or more time points to assess the efficacy of a treatment regimen. As will be appreciated by persons skilled in the art, the relative expression levels of MLP in specimens taken from a subject prior to and again after treatment, or, optionally, at progressive stages during treatment may be determined to assess the efficacy of treatment, wherein a decrease in the level of MLP over time is indicative of treatment efficacy.

3. In Vivo Assays for Determining the Presence of the MLP Antigen in a Living Subject In another aspect, the anti-MLP antibodies of the present invention are used to detect the presence of MLP-expressing cells in a living subject, such as an apparently healthy subject, or a subject at risk for developing an epithelial cancer, or a subject suspected of having early stage epithelial cancer, or a subject suffering from an epithelial cancer such as ovarian, pancreatic, colorectal, breast, appendiceal, lung, renal, cervical, biliary, esophageal, epithelial skin and/or other mucin-secreting types of cancer. Various methods of in vivo diagnostic imaging with radiolabeled monoclonal antibodies are well known in the art. For diagnostic imaging, the subject anti-MLP antibodies or antigen-binding fragments thereof are labeled with a detectable moiety suitable for use in vivo, as described herein, (e.g., a gamma-emitting radioisotope) and introduced into a patient. For example, in the technique of immunoscintigraphy, anti-MLP antibodies are labeled with a gamma-emitting radioisotope and introduced into a patient and a gamma camera is used to detect the location and distribution of gamma-emitting radioisotopes. See, for example, Srivastava (ed.), *Radiolabeled Monoclonal Antibodies for Imaging and Therapy* (Plenum Press 1988); Chase, "Medical Applications of Radioisotopes," in *Remington's Pharmaceutical Sciences,* 18th Edition, Gennaro et al. (eds.), pp. 624-652 (Mack Publishing Co., 1990); and Brown, "Clinical Use of Monoclonal Antibodies," in *Biotechnology and Pharmacy,* Pezzuto et al. (eds.) (Chapman & Hall 1993). The radiation dose delivered to the patient is maintained at as low a level as possible through the choice of isotope for the best combination of minimum half-life, minimum retention in the body, and minimum quantity of isotope which will permit detection and accurate measurement.

In a preferred embodiment, the anti-MLP antibodies for in vivo use in a human subject are humanized or human antibodies in order to reduce the human antimouse antibody (HAMA) response. Humanized or human anti-MLP monoclonal antibodies are suitable for use in the in vitro and in vivo diagnostic and therapeutic methods described herein.

In accordance with the foregoing, in one aspect, the present invention provides a method of detecting or diagnosing ovarian, pancreatic, colorectal, breast, appendiceal, lung, renal, cervical, biliary, esophageal, epithelial skin and/or other mucin-secreting types of cancer comprising (a) administering to a living subject a humanized or fully human anti-MLP antibody or antigen-binding fragment thereof that binds to an epitope in the C-terminal region of MLP, set forth as SEQ ID NO:4; and (b) detecting the presence or absence or amount of the antibody or fragment thereof bound to MLP, wherein detection of the presence of MLP in the subject indicates the presence of ovarian, pancreatic, colorectal, breast, appendiceal, lung, renal, cervical, biliary, esophageal, epithelial skin and/or other mucin-secreting types of cancer. In one embodiment, the anti-MLP antibody is labeled with a detectable moiety suitable for in vivo use. In one embodiment, the method is used in an imaging, intraoperative, endoscopic or intravascular procedure.

In one embodiment, the anti-MLP antibody or fragment thereof is a monoclonal antibody that binds to the same epitope or competes for binding to MLP with a reference antibody selected from the group consisting of: (i) the monoclonal anti-MLP antibody Clone 11 produced by the cell line deposited at the ATCC on Oct. 30, 2014 under the ATCC Designation number PTA-121699; (ii) the monoclonal anti-MLP antibody Clone B produced by the hybridoma cell line deposited at the ATCC on Oct. 30, 2014 under the ATCC Designation number PTA-121700; and (iii) the monoclonal anti-MLP antibody Clone C produced by the hybridoma cell line deposited at the ATCC on Oct. 30, 2014 under the ATCC Designation number PTA-121701.

In one embodiment, the anti-MLP antibody or fragment thereof is a monoclonal antibody having a heavy chain variable region CDR-H3 sequence comprising an amino acid sequence set forth as SEQ ID NO:15 or SEQ ID NO:35 or SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof. In one embodiment, said antibody, or antigen binding fragment thereof, comprises (i) a heavy chain variable region comprising CDR-H1 (SEQ ID NO:13), CDR-H2 (SEQ ID NO:14) and CDR-H3 (SEQ ID NO:15 or SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof. In one embodiment, said antibody or antigen binding fragment thereof comprises (i) a heavy chain variable region comprising CDR-H1 (SEQ ID NO:13), CDR-H2 (SEQ ID NO:16) and CDR-H3 (SEQ ID NO:15 or SEQ ID NO:35 or SEQ ID NO:36) and (ii) a light chain variable region comprising CDR-L1 (SEQ ID NO:24), CDR-L2 (SEQ ID NO:22) and CDR-L3 (SEQ ID NO:23), and conservative modifications thereof. In one embodiment, said antibody, or antigen binding fragment thereof comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

In one embodiment, the test subject is apparently healthy.

In one embodiment, the test subject has a family history of ovarian or pancreatic cancer or other mucin-secreting malignant neoplasm.

In one embodiment, the test subject is experiencing one or more symptoms associated with ovarian cancer. For example, symptoms associated with ovarian cancer in a human female subject include one or more of the following: pelvic mass, ascites, abdominal distention, abdominal pressure, swelling or bloating, pelvic pain or discomfort, nausea, constipation, gas, indigestion, diarrhea, urinary problems with as frequent urination or urgent need to urinate, loss of appetite or a quick feeling of fullness; increased abdominal circumference or tight-fitting clothing, persistent lack of energy, weight gain or loss with no known reason, abnormal bleeding from the vagina and low back pain.

In one embodiment, the test subject is known to be suffering from a mucin-secreting cancer type selected from the group consisting of ovarian, pancreatic, colorectal, breast, appendiceal, lung, renal, cervical, biliary, esophageal, epithelial skin and/or other mucin-secreting types of cancer and has had or is currently undergoing treatment for ovarian, pancreatic, colorectal, breast, appendiceal, lung, renal, cervical, biliary, esophageal, epithelial skin and/or other mucin-secreting types of cancer. In one embodiment, more than one sample is obtained from a particular test subject at more than one point in time. In one embodiment, the method further comprises comparing the results of the assay at one or more time points to assess the efficacy of a treatment regimen. As will be appreciated by persons skilled in the art, the relative expression levels of MLP in specimens taken from a subject prior to and again after treatment, or, optionally, at progressive stages during treatment may be determined to assess the efficacy of treatment, wherein a decrease in the level of MLP over time is indicative of treatment efficacy.

VI. Therapeutic Methods of Using an Anti-MLP Antibody Coupled to, and/or in Combination with, a Therapeutic Agent In another aspect, therapeutic methods are provided for treating a malignancy comprising administering an anti-MLP antibody, or antigen-binding fragment thereof, such as the subject anti-MLP antibodies disclosed herein, to a subject suffering from an epithelial cancer such as ovarian or pancreatic cancer or other mucin-secreting malignant neoplasm. In one embodiment, the anti-MLP antibody or antigen-binding fragment thereof is administered to the subject in conjunction with one or more other therapeutic agents. In one embodiment, the anti-MLP antibody or antigen-binding fragment thereof is coupled to a therapeutic agent, as described herein. In a preferred embodiment, the anti-MLP antibodies and fragments thereof are humanized or fully human.

In embodiments where more than one therapeutic agent is used, the therapeutic agents may comprise multiple copies of the same therapeutic agent or else combinations of different therapeutic agents.

In one embodiment, an anti-MLP antibody or fragment thereof is coupled to a therapeutic agent to generate an epithelial cancer cell-targeting therapeutic agent. A wide variety of therapeutic reagents can be administered concurrently or sequentially, or advantageously conjugated to the antibodies of the invention, for example, drugs, toxins, oligonucleotides (e.g., siRNA), immunomodulators, hormones, hormone antagonists, enzymes, enzyme inhibitors, radionuclides, angiogenesis inhibitors, pro-apoptotic agents, etc. The therapeutic agents recited here are those agents that are useful for either conjugated to an antibody, fragment or fusion protein or for administration separately with a naked antibody as described above.

In accordance with the foregoing, in one aspect, the present invention provides a method of treating a subject suffering from a mucin-secreting cancer selected from the group consisting of ovarian, pancreatic, colorectal, breast, appendiceal, lung, renal, cervical, biliary, esophageal, epithelial skin and/or other mucin-secreting types of cancer comprising administering to an individual suffering from ovarian, pancreatic, colorectal, breast, appendiceal, lung, renal, cervical, biliary, esophageal, epithelial skin and/or other mucin-secreting types of cancer a humanized or fully human anti-MLP antibody or antigen-binding fragment thereof that binds to an epitope in the C-terminal region of MLP, set forth as SEQ ID NO:4, wherein the antibody or fragment thereof is coupled to a therapeutic agent. In one embodiment, the therapeutic agent is a chemotherapeutic agent. In one embodiment, the anti-MLP antibody or fragment thereof is a monoclonal antibody that binds to the same epitope or competes for binding to MLP with a reference antibody selected from the group consisting of: (i) the monoclonal anti-MLP antibody Clone 11 produced by the cell line deposited at the ATCC on Oct. 30, 2014 under the ATCC Designation number PTA-121699; (ii) the monoclonal anti-MLP antibody Clone B produced by the hybridoma cell line deposited at the ATCC on Oct. 30, 2014 under the ATCC Designation number PTA-121700; and (iii) the monoclonal anti-MLP antibody Clone C produced by the hybridoma cell line deposited at the ATCC on Oct. 30, 2014 under the ATCC Designation number PTA-121701.

In one embodiment, the anti-MLP antibody or fragment thereof is a monoclonal antibody having a heavy chain variable region CDR-H3 sequence comprising an amino acid sequence set forth as SEQ ID NO:15 or SEQ ID NO:35 or SEQ ID NO:36 or SEQ ID NO:19, and conservative sequence modifications thereof, and having a light chain variable region CDR-L3 sequence comprising an amino acid sequence set forth as SEQ ID NO:24 or SEQ ID NO:27, and conservative sequence modifications thereof.

In one embodiment, said antibody, or antigen binding fragment thereof, comprises (i) a heavy chain variable region comprising CDR-H1 (SEQ ID NO:13), CDR-H2 (SEQ ID NO:14) and CDR-H3 (SEQ ID NO:15 or SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof. In one embodiment, said antibody or antigen binding fragment thereof comprises (i) a heavy chain variable region comprising CDR-H1 (SEQ ID NO:13), CDR-H2 (SEQ ID NO:16) and CDR-H3 (SEQ ID NO:15 or SEQ ID NO:35 or SEQ ID NO:36) and (ii) a light chain variable region comprising CDR-L1 (SEQ ID NO:24), CDR-L2 (SEQ ID NO:22) and CDR-L3 (SEQ ID NO:23), and conservative modifications thereof. In one embodiment, said antibody, or antigen binding fragment thereof comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

Pharmaceutically Suitable Excipients

Additional pharmaceutical methods may be employed to control the duration of action of an anti-MLP antibody in a therapeutic application. Control release preparations can be prepared through the use of polymers to complex or adsorb the antibody, antibody fragment or fusion protein. For example, biocompatible polymers include matrices of poly (ethylene-co-vinyl acetate) and matrices of a polyanhydride copolymer of a stearic acid dimer and sebacic acid. Sherwood et al., Bio/Technology 10: 1446 (1992). The rate of release of an antibody, antibody fragment or fusion protein from such a matrix depends upon the molecular weight of the antibody, antibody fragment or fusion protein, the amount of antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Compositions comprising the subject anti-MLP antibodies, or fragments thereof may comprise one or more pharmaceutically suitable excipients, one or more additional ingredients, or some combination of these. The antibody can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The immunoconjugate, naked antibody, or fragment thereof may also be administered to a mammal subcutaneously or by other parenteral routes. In a preferred embodiment, the antibody or fragment thereof is administered in a dosage of 20 to 2000 milligrams protein per dose. Moreover, the administration may be by continuous infusion or by single or multiple boluses. In general, the dosage of an administered immunoconjugate or naked antibody for humans will vary depending upon such factors as the patient's age, weight, height, sex, general medical condition and previous medical history. Typically, it is desirable to provide the recipient with a dosage of immunoconjugate or naked antibody that is in the range of from about 1 mg/kg to 20 mg/kg as a single intravenous or infusion, although a lower or higher dosage also may be administered as circumstances dictate. This dosage may be repeated as needed, for example, once per week for four to ten weeks, preferably once per week for eight weeks, and more preferably, once per week for four weeks. It may also be given less frequently, such as every other week for several months, or more frequently, such as two- or three-time weekly. The dosage may be given through various parenteral routes, with appropriate adjustment of the dose and schedule.

VII. Compositions and Kits Comprising Anti-MLP Antibodies

Compositions

In another aspect, the invention provides compositions for treating ovarian or pancreatic cancer comprising a therapeutically effective amount of an MLP-specific monoclonal antibody or fragment thereof coupled to a therapeutic agent and a pharmaceutically acceptable carrier. In general, the MLP-specific antibody compositions of the present invention, coupled to, and/or combined with any other selected therapeutic agents, are suitably contained in a pharmaceutically acceptable carrier. The carrier is non-toxic, biocompatible and is selected so as not to detrimentally affect the biological activity of the MLP-specific antibody (and any other therapeutic agents combined therewith). Exemplary pharmaceutically acceptable carriers for polypeptides are described in U.S. Pat. No. 5,211,657 to Yamada. The MLP-specific antibodies may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

In another aspect, the invention provides a substrate, such as a solid support (e.g., an insoluble substrate, such as a plate or slide made of glass, plastic or metal, a polymer-coated bead, a tube, or a ceramic or metal chip) that comprises immobilized (or otherwise deposited) monoclonal anti-MLP antibodies. In some embodiments, the antibodies are immobilized (or deposited) at discrete locations (e.g., in the wells of a multiwall plate, or deposited in an array on a biochip). In some embodiments, the substrate comprising the anti-MLP antibodies may be part of a kit for detecting MLP in a biological sample obtained from a mammalian subject.

Kits

In another aspect, the invention provides kits (i.e., a packaged combination of reagents in predetermined amounts) with instructions for detecting the presence of MLP in a biological sample. Exemplary kits may contain at least one or more anti-MLP monoclonal antibody or antigen binding fragment thereof as described herein. Where the anti-MLP antibody is labeled with a detectable moiety, such as an enzyme, the kit will include substrates and cofactors required by the enzyme (e.g., a substrate precursor which provides the detectable chromophore or fluorophore). In addition, other additives may be included such as stabilizers, buffers (e.g., a blocking buffer or lysis buffer) and the like. The relative amounts of the various reagents may be varied widely to provide for concentrations in solution of the reagents, which substantially optimize the sensitivity of the assay. Particularly, the reagents may be provided as dry powders, usually lyophilized, including excipients which on dissolution will provide a reagent solution having the appropriate concentration.

In addition, kits may include instructional materials disclosing means of use of an antibody of the present invention (e.g., for detection of MLP as a biomarker for ovarian or pancreatic cancer). The kits may also include additional components to facilitate the particular application for which the kit is designed. For example, the kit may additionally contain means of detecting a label (e.g., enzyme substrates for enzymatic labels, filter sets to detect fluorescent labels, appropriate secondary labels such as a sheep anti-mouse-HRP or the like). The kits may additionally include buffers and other reagents routinely used for the practice of a particular immunoassay, as is well known in the art.

The following examples merely illustrate the best mode now contemplated for practicing the invention, but should not be construed to limit the invention.

Example 1

This Example demonstrates that glycosylated mucin-like protein (gMLP) is a biomarker of ovarian cancer and describes the recombinant expression and protein production of a recombinant fusion protein comprising the novel C-terminal region of human MLP protein and the generation of monoclonal antibodies that specifically bind to the C-terminal region of human MLP.

Background/Rationale:

Mucins, which are high molecular-weight glycoproteins, are the major structural component of mucus, a gel that covers epithelial cell surfaces. The mucin family is composed of glycoproteins that contain a protein backbone conjugated with a large number of O-linked oligosaccharide chains and a few N-glycan chains (Andrianifahanana et al., *Biochimica Et Biophysica Acta Reviews on Cancer*, 1765: 189-222, 2006). The mucin family is highly glycosylated, and the molecular weight of these glycoproteins is typically around 200 kDa to >1000 kDa. The glycoproteins contain three domains: N-terminal domain, C-terminal domain and in the middle have tandem repeats. O-glycosidic bound N-terminus bind to the hydroxyl side chain of a repetitive tandem repeat structure. Such tandem repeats contain a frequent and rich quantity of Serine (Ser), Proline (Pro) and Threonine (Thr) amino acid residues (Kim et al., Glycoconjugate Journal 13:693-707, 1996).

The mucin family, which includes a total of twenty family members, is divided into two classes, (i) the secreted mucins (both gel forming and non-gel forming) and (ii) the membrane-bound mucins.

The secreted mucin gel-forming proteins are expressed by globlet cells (surface epithelium) and mucosa cells (sub mucosal gland) and include MUC2, MUC5AC, MUC5B, MUC6 and MUC19 (Chauhan et al., *Journal of Ovarian Research* 2:212-215, 2009; Chen et al., *American Journal of Respiratory Cell and Molecular Biology* 30:155-165, 2004). Secreted mucin non-gel forming proteins include MUC7, MUC8 and MUC9, both MUC8 and MUC9 high tandem repeat than MUC7. MUC7 was found in saliva secretions (Andrianifahanana et al., 2006, supra).

The membrane-bound mucins include MUC1, MUC3A, MUC3B, MUC4, MUC12, MUCI13, MUC15, MUC16, MUCI17, and MUCI20 (Andrianifahanana et al., 2006, supra). The membrane-bound mucins are expressed in normal cells, but are overexpressed in cancer conditions, cystic fibrosis and asthma (Bafna et al., *Oncogene* 29:2893-2904, 2010). In normal (noncancerous cells), the functions of mucins include cytoprotection (protection of the cells against biological agent), lubrication of the epithelial luminal surfaces, cell adhesion and interaction between each cell (Brockhausen et al., *EMBO Reports* 7:599-604, 2006). However, it has been shown that mucins in cancer cells have an increased level of, as well as altered, glycosylation. Cancer cells overexpress mucin on the cell surface, which may affect cellular adhesion and metastasis (Richards et al., *Cancer Immunology, Immunotherapy* 46:245-252, 1998). It has also been determined that mucins in cancer cells have altered glycosylation resulting, for example, from the synthesis of sialyl-Tn antigen truncated oligosaccharide side chains and Tn antigen leading to the accumulation of core oligosaccharides (see Yamashita et al., *Journal of the National Cancer Institute* 87:441-446, 1995). Numerous alterations of mucin antigens have been described in neoplastic epithelial tissues and in the sera of patients with, for example, pancreatic, breast, ovarian and colon cancer, and these antigens (e.g., DF3, CA19-9, CA125, SPan-1 and DuPan2) have been used as diagnostic markers (Ho. S. B. et al., *Cancer Res* 53:641-651, 1993). In ovarian epithelium malignancy leads to overexpression of oligosaccharides, which can be used as a tumor marker for early detection of ovarian cancer (Giuntoli et al., *Cancer Research* 58:5546-5550, 1998).

As described in WO98/48014, a novel mucin-like protein (MLP), also referred to as "MUC-B1" was identified as a previously unrecognized member of the human mucin family. It was determined that MLP is a glycoprotein composed of a protein backbone, which is highly glycosylated with O-linked oligosaccharides. The high degree of glycosylation accounts for most of the molecule weight of the native glycoprotein. In situ hybridization using a MLP-specific DNA probe indicated that the MLP gene is located on chromosome 7. As further described in WO 98/48014, two different partial cDNA transcripts encoding MLP were isolated and it was determined at the time of cloning that both clones contained two possible ORF's at the 5' end (ORF1 and ORF2), encoding very similar peptides with multiple tandem repeat motifs. Both deduced peptides were expressed in *E. coli* and were used as antigens to generate antibodies. It was determined by immunohistological analysis using the antibodies raised against the peptides encoded by ORF1 and ORF2 that glycosylated MLP (gMLP) is exclusively expressed and released by a substantial proportion of epithelial cancers such as ovarian and pancreatic tumor cells and is not present in normal ovarian tissue or ovarian cysts with no signs of malignancy. It was also determined that MLP is not specifically filtered by the kidney, so tumors may be easily detected by testing for MLP in blood.

The present inventors have since determined that the sequence of the predicted protein published in WO 98/48014 is incorrect, likely due to difficulties with contig assembly during genomic sequencings due to the highly repetitive central section of the sequence. The present inventors have carried out genome-derived sequencing and have now identified a single exon gene on chromosome 7 which encodes the correct full-length sequence of mucin-like protein (MLP), also referred to as MUC-B), set forth as SEQ ID NO:1, which has a length of 431 residues and contains a novel C-terminal region (set forth as SEQ ID NO:4, including SEQ ID NO:5 and SEQ ID NO:6) that was not previously described in WO98/48014. Knowledge of the correct, complete cDNA sequence coding for MLP allows for the expression of a recombinant polypeptide corresponding to the C-terminal region of the protein (e.g., a polypeptide comprising or consisting of SEQ ID NO:4, SEQ ID NO:5 or SEQ ID NO:6) for use as an antigen to generate MLP-specific monoclonal antibodies, as described herein. The novel C-terminal region of MLP was chosen for use as an antigen to generate anti-MLP monoclonal antibodies because of the high immunogenicity of this sequence, the very high degree of specificity for MLP (as described herein), and the low degree of similarity between this region and any other peptide sequence in the database. It is further noted that the MLP protein is heavily glycosylated, however, the extreme C-terminal 29 amino acid region of MLP (set forth as SEQ ID NO:6) contains only two predicted glycosylation sites (as determined by the NetOGlyc prediction program). Therefore, anti-MLP antibodies raised against this C-terminal region are capable of binding to the protein backbone of the highly glycosylated MLP glycoprotein secreted from MLP positive eukaryotic cells as the peptide epitopes of these C-terminal MLP specific antigen sites are not obscured by glycosylation.

As described in this example, the C-terminal region (SEQ ID NO:4 corresponding to aa 279-431 of full length MLP, shown as the underlined region in FIG. 1) was expressed as a fusion protein with an N-terminal histidine tag for use as an antigen to generate MLP C-terminal specific monoclonal antibodies.

Methods

1. Expression of rMLP C-Terminal Polypeptide Antigen

A nucleic acid sequence (SEQ ID NO:2) encoding a fusion protein comprising the C-terminal region (aa 279-431 of human MLP, set forth as SEQ ID NO:1) fused to a HIS tag as shown in FIG. 2, was cloned into the pRSETB expression vector (Invitrogen), for expression of the recombinant (rMLP) C-terminal fusion protein in *E. coli*.

Purification of rMLP C-terminal fusion protein was carried out using a HIS GRAVITRAP™ nickel column. The bound recombinant rMLP C-terminal protein was washed with 20 ml PBS buffer and then washed again with 10 mM Imidazole before eluting with 200 mM Imidazole. Fractions were collected from the column and analyzed by 12% SDS-PAGE. Fractions containing purified rMLP C-terminal protein were pooled and concentrated to yield the purified rMLP protein (0.53 mg/ml). Western blot analysis using a polyhistidine tag specific antibody showed that the purified rMLP C-terminal protein ran at the predicted molecule weight of 28 kDa (data not shown).

2. Generation of Monoclonal Antibodies that Specifically Bind the C-Terminal Region of Human MLP Mice were immunized with the purified rMLP C-terminal protein and then boosted with the same protein. Mice with high titers of antibodies were sacrificed, spleen cells from each mouse were fused to myeloma cells following standard procedures and supernatants from clones of hybridoma cells were screening using an enzyme-linked immuno-sorbent assay (ELISA). Eight candidate murine hybridomas were selected for analysis (named clones 1, 4, 5, 6, 7, 11, clone B and clone C).

The hybridomas were grown in Dulbecco's modified eagle's medium (DMEM, Sigma-Aldrich) supplemented with 10% fetal bovine serum (FBS, Gibco), 5 mL L-glutamine 200 mM (Sigma-Aldrich) and 5 mL 100 U/mL penicillin-streptomycin (Sigma-Aldrich). The hybridomas were cultured and mouse IgG antibodies were purified from the supernatants via protein G sepharose column chromatography (GE Healthcare), which have the ability to bind with the Fc region of IgG immunoglobulins. The purified monoclonal antibodies were then analyzed by 12% SDS PAGE under reducing conditions and stained with Coomassie Blue, which showed the expected light and heavy chain Ig bands at 25 kDa and 50 kDa (data not shown).

3. Testing Candidate Anti-MLP Monoclonal Antibodies Against rMLP C-Terminal Protein in an ELISA Assay Micro-titer ELISA plates (Maxisorb, NUNC™), were coated with 10.0 µg/ml of recombinant MLP C-terminal protein using coating buffer (15 mM sodium carbonate anhydrous $Na_2CO_3$ and sodium hydrogen carbonate $NaHCO_3$, pH 9.6). The plate was incubated overnight at 4° C. The next day, residual protein binding sites were blocked by adding 250 µL of 1% bovine serum albumen (BSA) in TBS buffer (10 mM Tris-HCL, 140 mM NaCl and 10 mM CaCl$_2$, pH 7.4) to each well in the plate and incubated at room temperature for 2 hours. The plates were then washed three times with TBS buffer with 0.05% and Tween20. Serial dilution of monoclonal antibodies in TBS buffer (clone 1, 4, 5, 6, 7, C, 11 and B) were added to the plates in duplicate starting from 1:100 dilution and incubated for two hours at room temperature. Wells were then washed three times. 100 of goat anti-mouse antibody conjugated with alkaline phosphatase (diluted 1:5000) was then added to each well and incubated for two hours at room temperature. The plates were washed three times; substrate solution (fast p-Nitrophenyl phosphate tablet sets, Sigma) was then added and incubated at room temperature for 20 to 30 minutes. The absorbance was measured at 405 nm using Biorad ELISA micro-titre plate reader model 608.

Results:

Three of the eight mAb clones tested (clone 11, B and C) were positive in an ELISA assay against the recombinant MLP-C terminal protein, although the signal with clone C was much weaker than the signals seen with clones 11 and B, while five of the mAb clones were negative in the ELISA assay (data not shown). mAb clones B and 11 showed good binding against MLP with a titer of approximately 1 µg/ml.

To confirm the specificity of clones 11 and B for the MLP C-terminal protein, they were also tested in an ELISA assay against an unrelated control protein (plates were coated with 10.0 µg/ml of recombinant MASP-3) and were all found to be negative (data not shown).

4. Detection of rMLP by Anti-MLP Clones 11 and B by ELISA Assay

Micro-titer ELISA plates (Maxisorb, NUNC™), were coated with anti-MLP monoclonal antibody clone 11 and clone B at serial dilutions starting at a concentration of 1 µg/mL down to 0.05 µg/mL using coating buffer (15 mM sodium carbonate anhydrous Na$_2$CO$_3$ and sodium hydrogen carbonate NaHCO$_3$, pH 9.6). The plate was incubated overnight at 4° C. The next day, residual protein binding sites were blocked by adding 250 µL of 1% bovine serum albumen (BSA) in TBS buffer (10 mM Tris-HCL, 140 mM NaCl and 10 mM CaCl$_2$, pH 7.4) to each well in the plate and incubated at room temperature for 2 hours. The plates were then washed three times with TBS buffer with 0.05% and Tween20. Serial dilutions of recombinant MLP C-terminal protein in a concentration range of from 0.01 µg/mL to 5 µg/mL were added to the plates in duplicate and incubated for two hours at room temperature. Wells were then washed three times. 100 µL of polyclonal goat anti-MLP antibody conjugated with alkaline phosphatase (diluted 1:5000) was then added to each well and incubated for two hours at room temperature. The plates were washed three times; substrate solution (fast p-Nitrophenyl phosphate tablet sets, Sigma) was then added and incubated at room temperature for 20 to 30 minutes. The absorbance was measured at 405 nm using Biorad ELISA micro-titre plate reader model 608. As a negative control, plates were coated with monoclonal anti-MLP antibody clone B or clone 11 and developed with the polyclonal goat anti-MLP antibody, but instead of the MLP antigen, only TBS buffer was added to the mAb-coated plates.

Results:

FIG. 3A graphically illustrates the detection of rMLP by anti-MLP mAb clone B by ELISA assay. As shown in FIG. 3A, the sensitivity of this assay is very high, showing detection of the rMLP antigen down to a concentration of 0.01 µg/mL. As further shown in FIG. 3A, dilution of the primary antibody mAb clone B down to 0.01625 µg/mL appears to give close to a maximal signal.

Figure 3B:
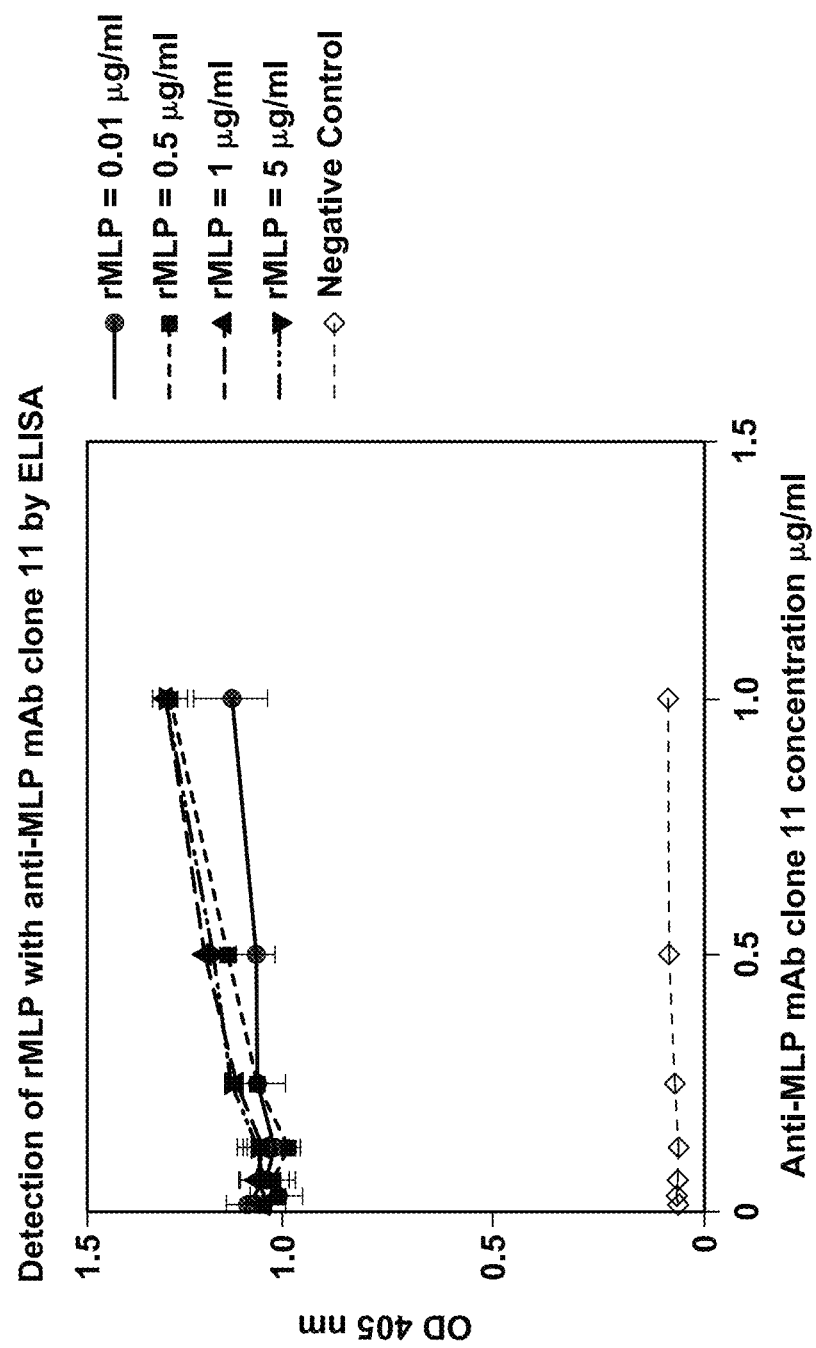
FIG. 3B graphically illustrates the results of an ELISA assay carried out with anti-MLP monoclonal antibody clone 11 tested against various concentrations of recombinant MLP (rMLP) C-terminal protein, as described in Example 1.

FIG. 3B graphically illustrates the detection of rMLP by anti-MLP mAb clone 11 by ELISA assay. As shown in FIG. 3B, the sensitivity of this assay is very high, showing detection of the rMLP antigen down to a concentration of 0.01 µg/mL. As further shown in FIG. 3B, dilution of the primary antibody mAb clone 11 down to 0.01625 µg/mL appears to give close to a maximal signal.

5. Development of a Sandwich ELISA Assay to Detect MLP

Micro-titer ELISA plates (Maxisorb, NUNC™), were coated with anti-MLP monoclonal antibody clone 11 at 0.1 µg per well using coating buffer (15 mM sodium carbonate anhydrous Na$_2$CO$_3$ and sodium hydrogen carbonate NaHCO$_3$, pH 9.6). The plate was incubated overnight at 4° C. The next day, residual protein binding sites were blocked by adding 250 µL of 1% bovine serum albumen (BSA) in TBS buffer (10 mM Tris-HCL, 140 mM NaCl and 10 mM CaCl$_2$, pH 7.4) to each well in the plate and incubated at room temperature for 2 hours. The plates were then washed three times with TBS buffer with 0.05% and Tween20. Serial dilutions of recombinant MLP C-terminal protein in a concentration range of from 0.0001 µg/mL to 1 µg/mL were added to the plates in duplicate and incubated for two hours at room temperature. Wells were then washed three times. Polyclonal goat anti-MLP antibody conjugated with alkaline phosphatase (0.5 µg/mL) was then added to each well and incubated for two hours at room temperature. The plates were washed three times; substrate solution (fast p-Nitrophenyl phosphate tablet sets, Sigma) was then added and incubated at room temperature for 20 to 30 minutes. The absorbance was measured at 405 nm using Biorad ELISA micro-titre plate reader model 608. As a negative control, the coating antibody mAb clone 11 was omitted and the wells were incubated with coating buffer prior to the addition of rMLP and the polyclonal MLP detection antibody.

Figure 4:
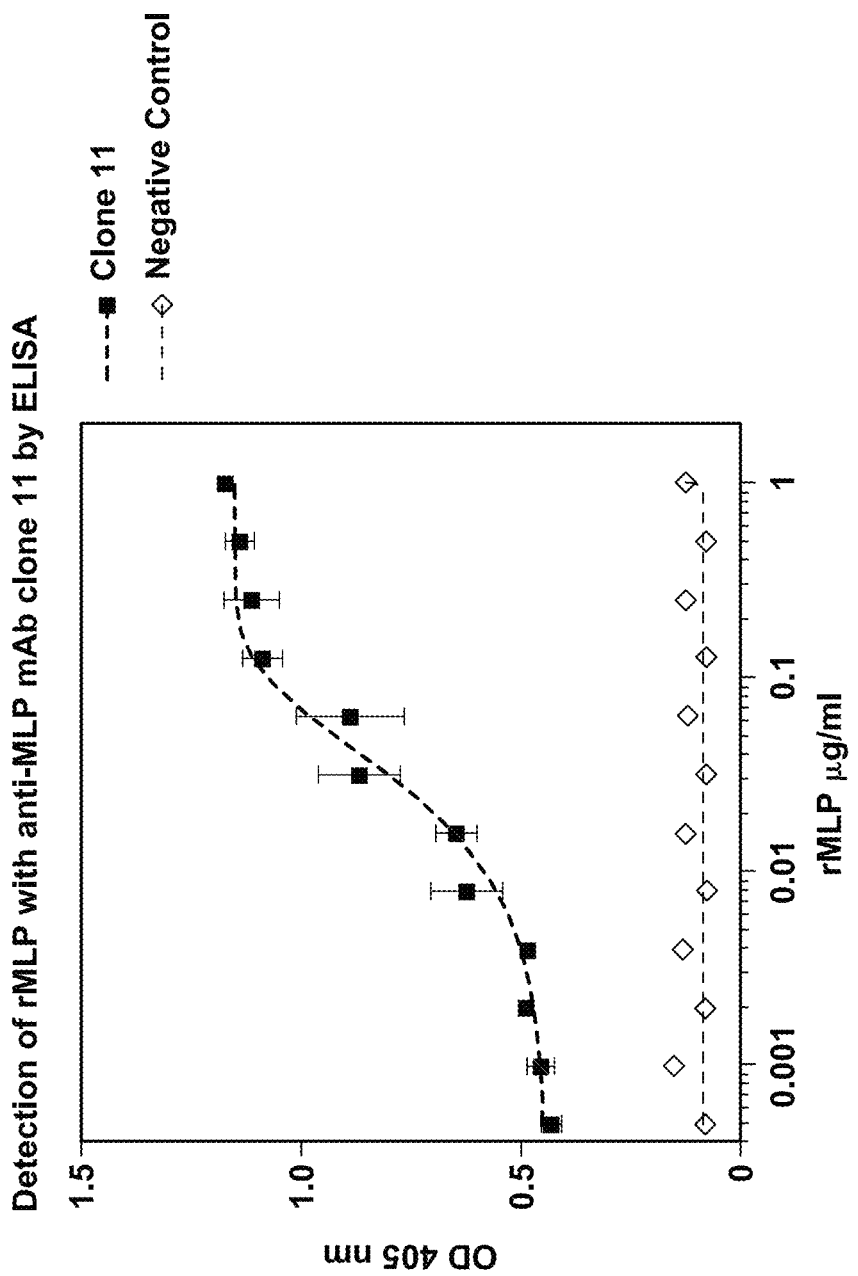
FIG. 4 graphically illustrates the results of an ELISA assay carried out with anti-MLP monoclonal antibody clone 11 tested against recombinant MLP (rMLP) C-terminal protein, as described in Example 1.

Results:

FIG. 4 graphically illustrates the detection of rMLP with anti-MLP mAb clone 11 by ELISA assay. As shown in FIG. 4, the sensitivity of this sandwich ELISA assay is very high, showing linearity down to a concentration of less than 10 ng/mL rMLP.

Example 2

This Example describes Analysis of anti-MLP monoclonal antibody Clones C, 11 and B for Use as an Epithelial Cancer Cell Biomarker.

Background/Rationale:

Panc-1 is a human pancreatic carcinoma, epithelial-like cell line and is used as an in vitro model of non-endocrine pancreatic cancer for tumorigenicity studies (ATCC CRL-1469). Cell line A2780 is a human ovarian carcinoma cancer cell line (Louie K. G. et al., Cancer Res 45(5):2110-5, 1985; Hamilton T. C. et al., Seminars in Oncology 11(3):285-298, 1984).

The following experiment was carried out to determine if the anti-MLP monoclonal antibody clones C, 11 and B are capable of detecting glycosylated MLP (gMLP) secreted from Panc-1 and A2780 cell lines.

Methods:

1. Analysis of Anti-MLP mAb Clones C, 11 and B for Binding to gMLP Secreted from Panc-1 (Human Pancreatic Cancer Cell Line):

The three anti-MLP mAbs (clones C, 11 and B) were tested for binding to gMLP present in supernatant obtained from a human pancreatic cell line (Panc1) obtained from the ATCC in a dot blot and ELISA assay format as follows.

A. Dot Blot Analysis

The three anti-MLP mAbs (clones C, 11 and B) generated as described in Example 1, were tested against a human pancreatic cancer cell line (Panc-1) obtained from the ATCC. Dot blot analysis of the purified anti-MLP specific mAbs (clones C, 11 and B), was carried out with the rMLP C-terminal protein and glycosylated full length MLP (gMLP) that is present in the supernatant of pancreatic cancer cell line Panc-1.

4 µl of protein (rMLP, gMLP from Panc1 supernatant, or rMASP-3) was dropped onto a nitrocellulose membrane and allowed to dry at room temperature. The nitrocellulose membrane was then blocked with 5% skimmed milk in PBS for 45 to 60 minutes with gently shaking at room temperature. Anti-MLP mAb clones C, 11 and B (final concentration of mAbs 1:1000 dilution of a 1 mg/ml protein G Sepharose enriched antibody stock in a volume of 10 mL 5% skimmed milk in PBS) were then added to the nitrocellulose membrane and incubated at room temperature for 1 hour with gently shaking. The membranes were then washed three times with PBS and 0.05% Tween 20. Anti-mouse antibody conjugated with horseradish peroxidase (HRP) diluted 1:6000 was added and incubated at room temperature for 1 hour with gently shaking. The membrane was then washed three times and antibody binding was detected by ECL kit.

Figure 5:
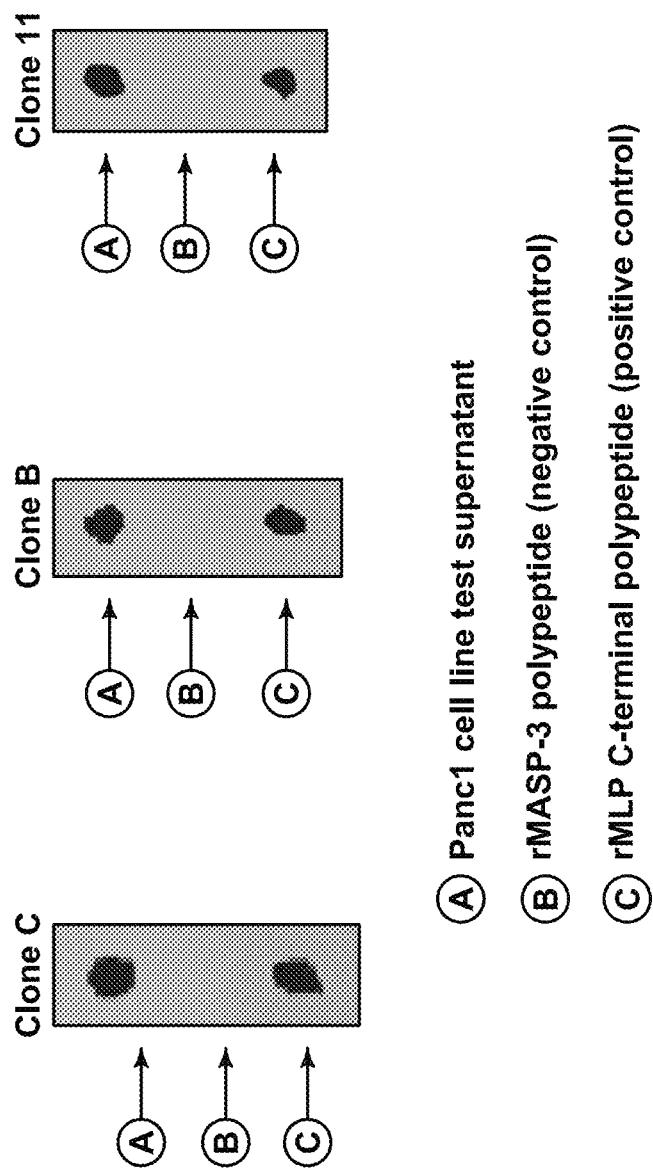
FIG. 5 shows the results of a dot blot assay carried out with anti-MLP monoclonal antibody Clone C, Clone B and Clone 11 against Panc1 cell line supernatant (row A), rMASP-3 polypeptide (row B) and mMLP C-terminal protein (row C), as described in Example 2.

Results of Dot Blot Analysis:

FIG. 5 shows the results of a dot blot assay carried out with anti-MLP monoclonal antibody Clone C, Clone B and Clone 11 against Panc1 cell line supernatant (row A), rMASP-3 polypeptide (row B) and mMLP C-terminal protein (row C). As shown in FIG. 5, all three mAbs (clone C, clone B and clone 11) were found to bind to the naturally produced glycosylated form of MLP (gMLP) present in the supernatant of the Panc-1 cell line (row A), and the rMLP C-terminal protein control (row C), but did not bind to the negative control rMASP-3 polypeptide (row B).

B. ELISA Assay Using Plates Coated with gMLP from Ovarian Cancer Cell Line A2789

The three anti-MLP mAbs (clone 11, B and C) were tested with ELISA plates coated with 1.0 µg/ml of glycosylated MLP from concentrated supernatant obtained from ovarian cancer cell line A2789 as follows.

Micro-titer ELISA plates (Maxisorb, NUNC™), were coated with 1.0 µg/ml of glycosylated MLP (gMLP) from concentrated supernatant obtained from ovarian cancer cell line A2789 using coating buffer (15 mM sodium carbonate anhydrous $Na_2CO_3$ and sodium hydrogen carbonate $NaHCO_3$, pH 9.6). The plate was incubated overnight at 4° C. The next day, residual protein binding sites were blocked by adding 250 µL of 1% bovine serum albumen (BSA) in TBS buffer (10 mM Tris-HCL, 140 mM NaCl and 10 mM $CaCl_2$, pH 7.4) to each well in the plate and incubated at room temperature for 2 hours. The plates were then washed three times with TBS buffer with 0.05% and Tween20. Serial dilution of mAbs (clone 11, B and C) in TBS buffer were added to the plates in duplicate starting from a 1:100 dilution and incubated for two hours at room temperature. Wells were then washed three times. 100 µL of goat anti-mouse antibody conjugated with alkaline phosphatase (diluted 1:5000) was then added to each well and incubated for two hours at room temperature. The plates were washed three times, substrate solution (fast p-Nitrophenyl phosphate tablet sets, Sigma) was then added and incubated at room temperature for 20 to 30 minutes. The absorbance was measured at 405 nm using Biorad ELISA micro-titre plate reader model 608.

Results of ELISA Assay with Plates Coated with gMLP from Ovarian Cancer Cell Line A2789

Figure 6:
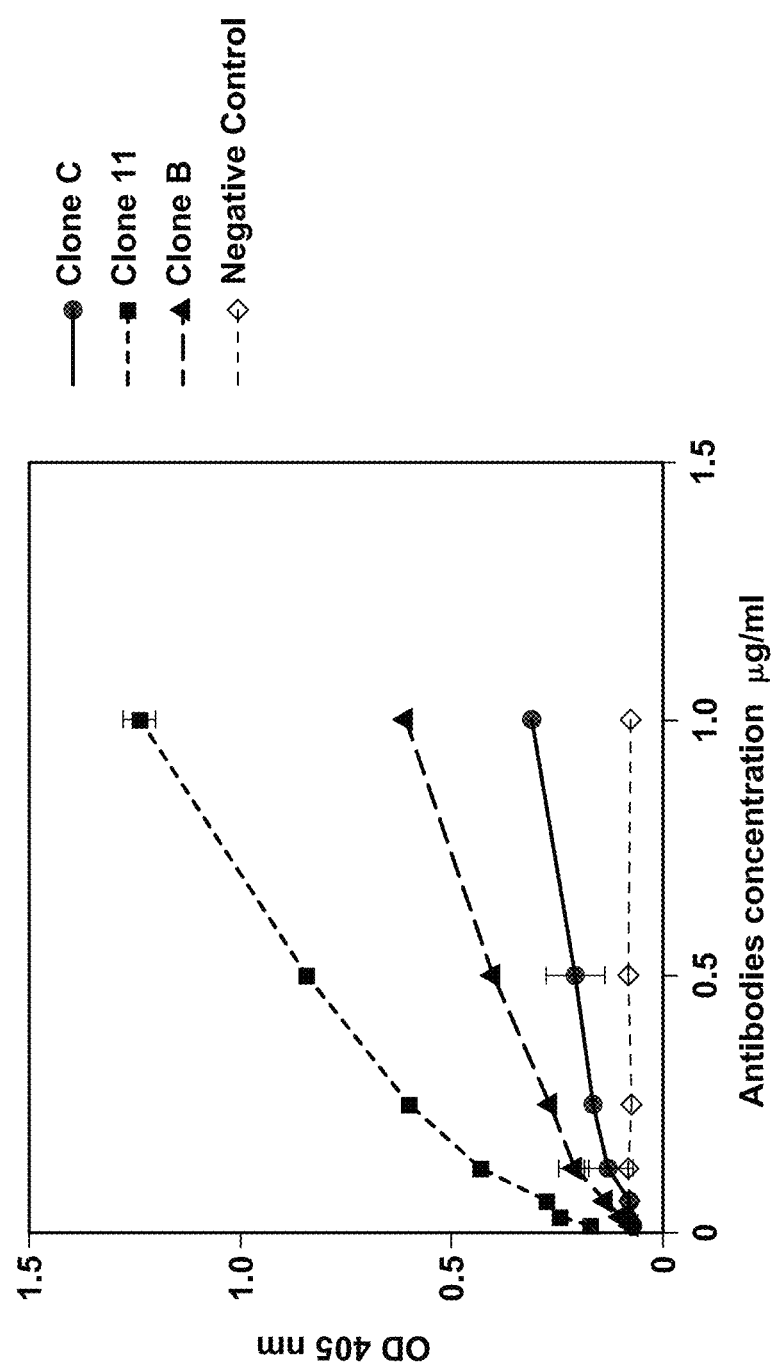
FIG. 6 graphically illustrates the results of an ELISA assay carried out with anti-MLP monoclonal antibody clones C, 11 and B against concentrated supernatant from the ovarian cancer cell line A2780 containing glycosylated full length MLP (gMLP), as described in Example 2.

As shown in FIG. 6, clones 11 and B showed significant binding to gMLP, however in this assay format clone C was only marginally higher for binding to gMLP than binding to the negative control rMASP-3 protein.

2. Analysis of Anti-MLP mAb Clones C, 11 and B for Binding to gMLP Secreted from Human Ovarian Cancer Cell Line A2780.

The three anti-MLP mAbs (clones C, 5, 11 and B) were tested for binding to gMLP present in supernatant obtained from a human ovarian cancer cell line (A2780) obtained from the ATCC in a dot blot, Western blot and ELISA assay format as follows.

A. Dot Blot Analysis

A dot blot assay was carried out as described above, using supernatant of ovarian cancer cell line A2780. 4 µl of protein (rMLP, gMLP from A2780 supernatant, or rMASP-3) was dropped onto a nitrocellulose membrane and allowed to dry at room temperature. The nitrocellulose membrane was then blocked with 5% skimmed milk in PBS for 45 to 60 minutes with gently shaking at room temperature. Anti-MLP mAb clones C, 11 and B (final concentration of mAbs 1:1000 dilution of a 1 mg/ml protein G Sepharose enriched antibody stock in a volume of 10 mL 5% skimmed milk in PBS) were then added to the nitrocellulose membrane and incubated at room temperature for 1 hour with gently shaking. The membranes were then washed three times with PBS and 0.05% Tween 20. Anti-mouse antibody conjugated with horseradish peroxidase (HRP) diluted 1:6000 was added and incubated at room temperature for 1 hour with gently shaking. The membrane was then washed three times and antibody binding was detected by ECL kit.

Figure 7:
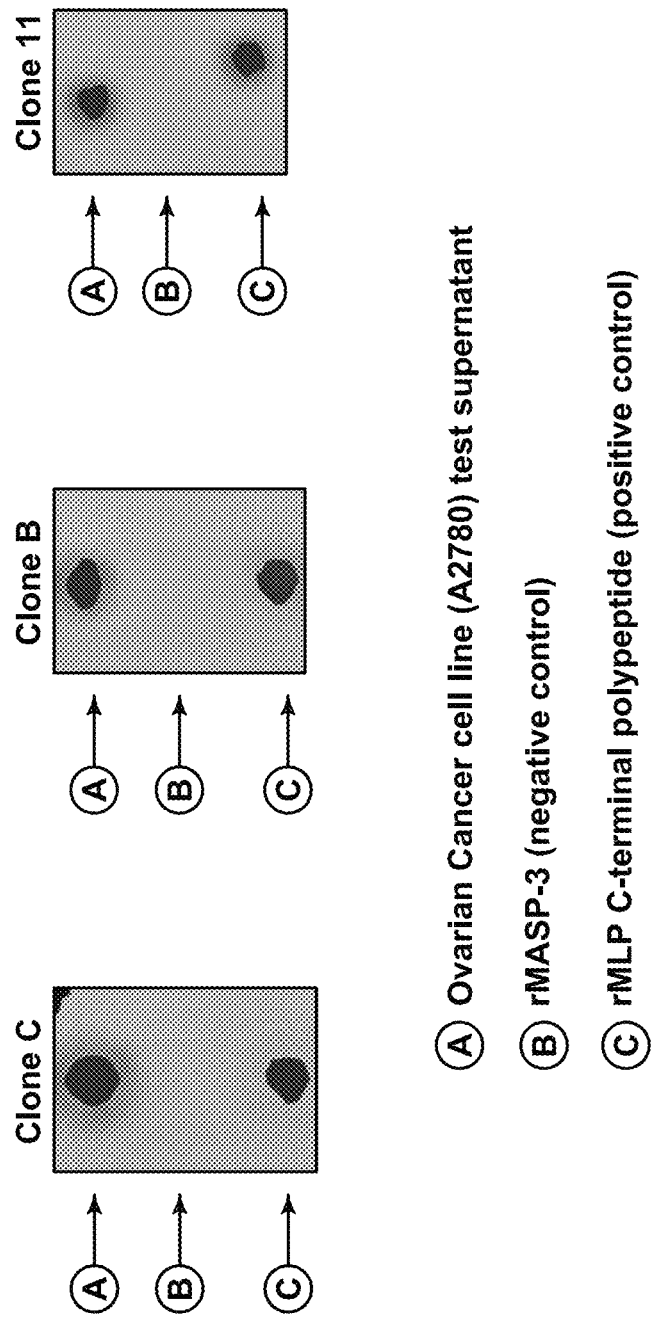
FIG. 7 shows the results of a dot blot assay carried out with anti-MLP antibody Clone C, Clone B and Clone 11 against ovarian cancer cell line A2780 supernatant (row A), rMASP-3 protein (row B) and rMLP C-terminal protein (row C), as described in Example 2.

Results of Dot Blot Analysis:

FIG. 7 shows the results of a dot blot assay carried out with anti-MLP antibody Clone C, Clone B and Clone 11 against ovarian cancer cell line A2780 supernatant (row A), rMASP-3 protein (row B) and rMLP C-terminal protein (row C).

As shown in FIG. 7, clone C, clone B and clone 11 were each found to bind to the naturally produced glycosylated form of MLP (gMLP) present in the supernatant of the A2780 cell line (row A), and the rMLP C-terminal protein control (row C), but did not bind to the negative control recombinant MASP-3 polypeptide (row B).

B. Western Blot Analysis

Figure 8:
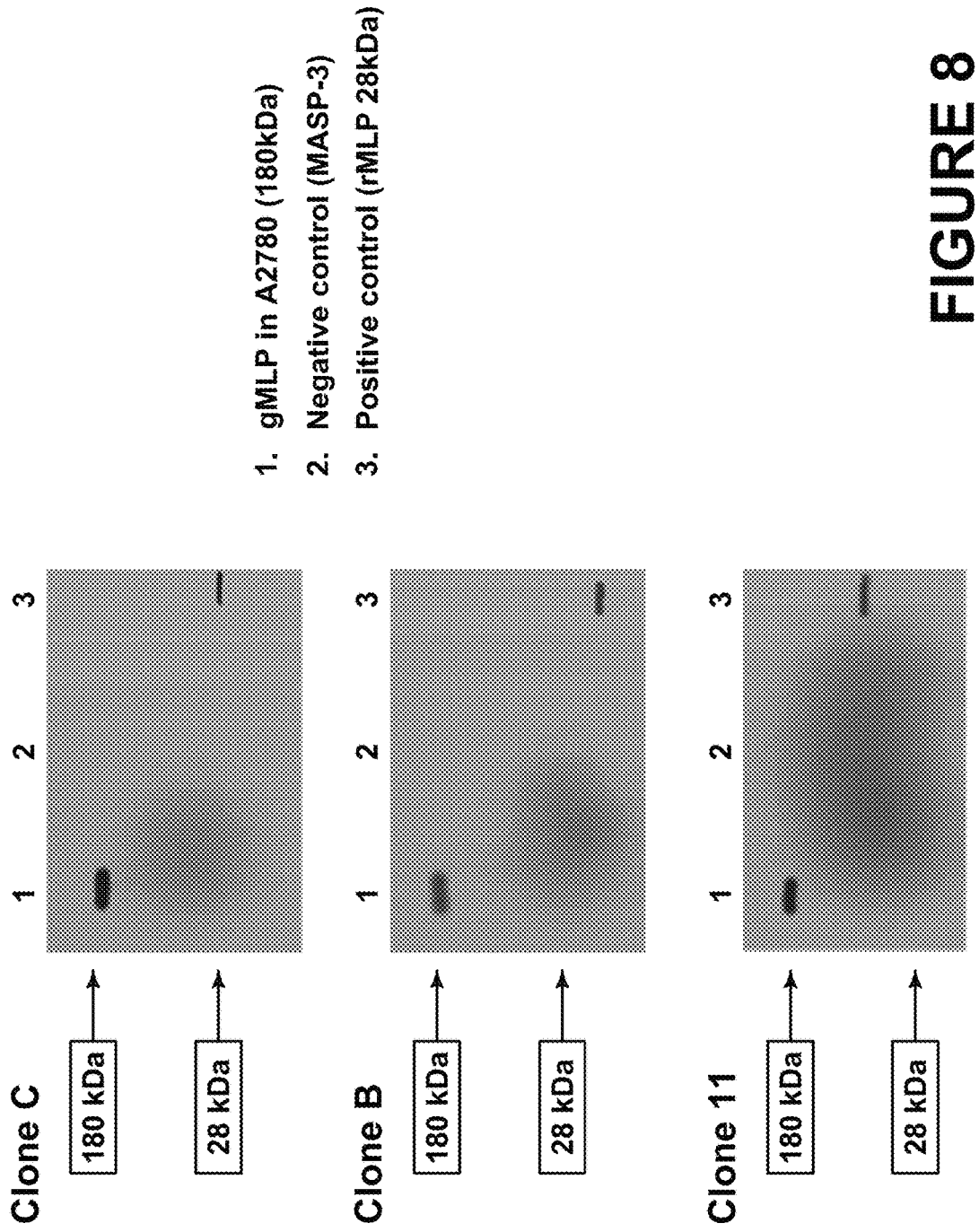
FIG. 8, top panel: shows the results of a Western blot demonstrating that anti-MLP clone C specifically recognizes gMLP in A2780 (row 1), and rMLP C-terminal protein (row 3), but not rMASP-3 protein (row 2); middle panel: shows the results of a Western blot demonstrating that anti-MLP clone B specifically recognizes gMLP in A2780 (row 1), and rMLP C-terminal protein (row 3), but not rMASP-3 protein (row 2); and lower panel: shows the results of a Western blot demonstrating that anti-MLP clone 11 specifically recognizes gMLP in A2780 (row 1), and rMLP C-terminal protein (row 3), but not rMASP-3 protein (row 2), as described in Example 2.

As shown in FIG. 8, the dot blot results were confirmed by Western blotting using the concentrated supernatant from the A2780 cell line, where the distinctive 180 kDa gMLP band (row 1) and the 28 kDa rMLP C-terminal protein (row 3) were detected with clone C (top panel), clone B (middle panel) and clone 11 (lower panel), and the negative control protein rMASP-3 (row 2) was not detected by the three MLP-specific mAbs.

C. ELISA Assay Using Plates Coated with gMLP from A2780 Cells

The three anti-MLP mAbs (clone C, 5, 11, and B) were tested with ELISA plates coated with 1 µg/ml of concentrated supernatant obtained from A2780 cells which contained trace amounts of glycosylated native MLP using the methods described above.

Results of ELISA Assay with Plates Coated with gMLP from A2780 Cells

Figure 9:
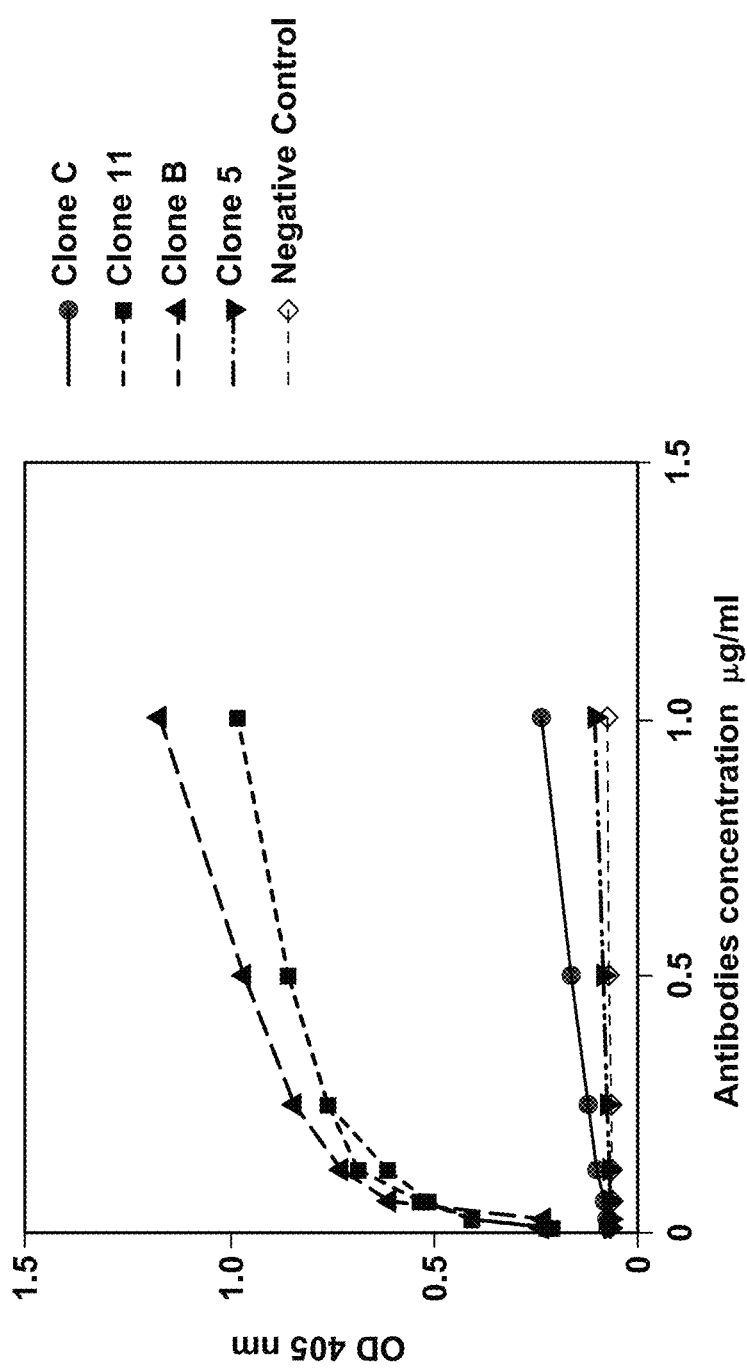
FIG. 9 graphically illustrates the results of an ELISA assay carried out with anti-MLP monoclonal antibody clones C, 5, 11 and B against concentrated supernatant from the ovarian cancer cell line A2780 containing glycosylated full length MLP (gMLP), as described in Example 2.

As shown in FIG. 9, clones 11 and B showed significant binding to gMLP from A2780 cells, however in this assay format clone C was only marginally higher for binding to gMLP than binding to the negative control rMASP-3 protein. The negative control in FIG. 9 is clone 11 against rMASP-3 protein.

TABLE 9

Summary of Results: detection of gMLP secreted from Panc1 and A2780 cancer cell lines

| Hybridoma Clone | Western Blot | Dot Blot | ELISA test positive with both rMLP and gMLP |
|---|---|---|---|
| Clone B | +++ | +++ | +++ |
| Clone 11 | +++ | +++ | +++ |
| Clone C | +++ | +++ | + |

Summary:

These results demonstrate that MLP-specific monoclonal antibody clones 11, B and C specifically bind rMLP C-terminal protein and are capable of detecting gMLP secreted from a pancreatic cancer cell line and an ovarian cancer cell line, as determined by Western blot and Dot blot. Further, this example demonstrates that MLP-specific monoclonal antibody clones 11 and B are able to detect both rMLP C-terminal protein and gMLP secreted from an ovarian cancer cell line in an ELISA assay format.

These MLP specific mAbs can be used in a sensitive detection ELISA, for example, in the format of a kit to measure MLP levels in the sera of ovarian cancer patients as a biomarker of early stage ovarian cancer, which is an urgently needed non-invasive early diagnosis to discover ovarian malignancies at an early stage when treatment is effective and the prognosis much better than in later stages of ovarian cancer.

Example 3

This Example describes the cloning and sequencing of the DNA encoding the VH and VL regions of anti-MLP monoclonal antibodies produced by hybridoma clones 11, B and C.

Methods:

Hybridoma cells of the cell lines secreting anti-MLP monoclonal antibodies referred to as αMLP Clone 11, αMLP Clone B and αMLP Clone C deposited at the ATCC on Oct. 30, 2014 under the ATCC Designation numbers PTA-121699, PTA-121700 and PTA-121701, respectively, were cultured in Dulbecco's modified eagle's medium (DMEM, Sigma-Aldrich) supplemented with 10% fetal bovine serum (FBS, Gibco), 5 mL L-glutamine 200 mM (Sigma-Aldrich) and 5 mL 100 U/mL penicillin-streptomycin (Sigma-Aldrich). DNA was purified from the hybridoma cell lines, the variable regions were PCR-amplified and sequence analysis of clones # C, 11 and B was carried out using standard methods.

Results:

Heavy Chain Variable Region (VH) Sequences

The amino acid sequence of the VH region of anti-MLP monoclonal antibody αMLP Clone 11, produced by the hybridoma cell line deposited at the ATCC on Oct. 30, 2014 as ATCC Designation Number PTA-121699 is set forth as SEQ ID NO:7.

The amino acid sequence of the VH region of anti-MLP monoclonal antibody αMLP Clone B, produced by the hybridoma cell line deposited at the ATCC on Oct. 30, 2014 as ATCC Designation Number PTA-121700 is set forth as SEQ ID NO:8.

The amino acid sequence of the VH region of anti-MLP monoclonal antibody αMLP Clone C, produced by the hybridoma cell line deposited at the ATCC on Oct. 30, 2014 as ATCC Designation Number PTA-121701 is set forth as SEQ ID NO:9.

FIG. 10A shows an amino acid sequence alignment between the variable heavy chain regions of anti-MLP monoclonal antibody clones 11 (SEQ ID NO:7), B (SEQ ID NO:8) and C (SEQ ID NO:9).

Light Chain Variable Region (VL) Sequences

The amino acid sequence of the VL region of anti-MLP monoclonal antibody αMLP Clone 11, produced by the hybridoma cell line deposited at the ATCC on Oct. 30, 2014 as ATCC Designation Number PTA-121699 is set forth as SEQ ID NO:10.

The amino acid sequence of the VL region of anti-MLP monoclonal antibody αMLP Clone B, produced by the hybridoma cell line deposited at the ATCC on Oct. 30, 2014 as ATCC Designation Number PTA-121700 is set forth as SEQ ID NO:11.

The amino acid sequence of the VL region of anti-MLP monoclonal antibody αMLP Clone C, produced by the hybridoma cell line deposited at the ATCC on Oct. 30, 2014 as ATCC Designation Number PTA-121701 is set forth as SEQ ID NO:12.

FIG. 10B shows an amino acid sequence alignment between the variable light chain regions of anti-MLP monoclonal antibody clones 11 (SEQ ID NO:10), B (SEQ ID NO:11) and 2(C) (SEQ ID NO:12).

The high degree of sequence identity between clone 11 and clone B suggests that both clones originated from the same parent hybridoma cell binding to the identical MLP epitope.

In accordance with various embodiments, the present disclosure provides:

1. An isolated antibody, or antigen binding fragment thereof, that specifically binds to an epitope in the C-terminal region of human mucin-like protein, set forth as SEQ ID NO:4.

2. The antibody of paragraph 1, wherein the antibody is a monoclonal antibody.

3. The antibody of paragraph 2, wherein said antibody is a recombinant, humanized or chimeric antibody.

4. The antibody of paragraph 2, wherein said antibody is a fully human antibody.

5. The antibody of paragraph 1, wherein said antibody or antigen binding fragment thereof is capable of binding to glycosylated human MLP secreted from an epithelial cancer cell line.

6. The antibody of paragraph 5, wherein said antibody or antigen binding fragment thereof is capable of binding to glycosylated human MLP in an ELISA assay format.

7. The antibody of paragraph 1, wherein said antibody or antigen binding fragment thereof binds to human MLP with an KD of less than 10 nM.

8. The antibody of paragraph 1, wherein said antibody, or antigen binding fragment thereof recognizes at least part of an epitope recognized by one or more reference antibodies selected from the group consisting of:

(i) the monoclonal anti-MLP antibody Clone 11 produced by the hybridoma cell line deposited at the ATCC on Oct. 30, 2014 under the ATCC Designation Number PTA-121699;

(ii) the monoclonal anti-MLP antibody Clone B produced by the hybridoma cell line deposited at the ATCC on Oct. 30, 2014 under the ATCC Designation Number PTA-121700; and (iii) the monoclonal anti-MLP antibody clone C produced by the hybridoma cell line deposited at the ATCC on Oct. 30, 2014 under the ATCC Designation Number PTA-121701.

9. The antibody of paragraph 1, wherein said antibody comprises a variable region of the heavy chain comprising or consisting of a sequence which is at least 90% identical to an amino acid sequence selected from the group consisting of SEQ ID NO:7, SEQ ID NO:8 and SEQ ID NO:9.

10. The antibody of paragraph 1, wherein said antibody comprises a variable region of the light chain comprising or consisting of a sequence which is at least 90% identical to an amino acid sequence selected from the group consisting of SEQ ID NO:10, SEQ ID NO:11 and SEQ ID NO:12.

11. The antibody of any of paragraphs 1-8, wherein said antibody is labeled with a detectable moiety.

12. The antibody of paragraph 1, wherein said antibody is coupled to a therapeutic agent.

13. The antibody of paragraph 1, wherein said antibody is immobilized on a substrate.

14. An isolated monoclonal antibody, or antigen binding fragment thereof, that binds to human mucin-like protein (MLP), comprising:

(i) a heavy chain variable region comprising CDR-H1, CDR-H2 and CDR-H3 sequences; and (ii) a light chain variable region comprising CDR-L1, CDR-L2 and CDR-L3, wherein the heavy chain variable region CDR-H3 sequence comprises an amino acid sequence set forth as SEQ ID NO:15, SEQ ID NO:35, SEQ ID NO:36 or SEQ ID NO:19, and conservative sequence modifications thereof, wherein the light chain variable region CDR-L3 sequence comprises an amino acid sequence set forth as SEQ ID NO:23 or SEQ ID NO:27, and conservative sequence modifications thereof, and wherein the isolated antibody binds to human mucin-like protein (MLP).

15. The isolated antibody or antigen binding fragment of paragraph 14, wherein the heavy chain variable region CDR-H2 sequence comprises an amino acid sequence set forth as SEQ ID NO:20, 14, 16 or 18, and conservative sequence modifications thereof.

16. The isolated antibody or antigen binding fragment of paragraph 15, wherein the heavy chain variable region CDR-H1 sequence comprises an amino acid sequence set forth as SEQ ID NO:13 or SEQ ID NO:17, and conservative modifications thereof.

17. The isolated antibody or antigen binding fragment of paragraph 16, wherein the light chain variable region CDR-L2 sequence comprises an amino acid sequence set forth as SEQ ID NO:22 or SEQ ID NO:26 and conservative modifications thereof.

18. The isolated antibody or antigen binding fragment of paragraph 17, wherein the light chain variable region CDR-L1 sequence comprises an amino acid sequence set forth as SEQ ID NO:28, SEQ ID NO:21, SEQ ID NO:24 or SEQ ID NO:25 and conservative modifications thereof.

19. The isolated antibody or antigen binding fragment of paragraph 16, wherein the CDR-H1 of the heavy chain variable region comprises SEQ ID NO:13.

20. The isolated antibody or antigen binding fragment of paragraph 15, wherein the CDR-H2 of the heavy chain variable region comprises SEQ ID NO:20.

21. The isolated antibody or antigen binding fragment of paragraph 14, wherein the CDR-H3 of the heavy chain variable region comprises SEQ ID NO:15.

22. The isolated antibody of paragraph 20, wherein the amino acid sequence set forth in SEQ ID NO:20 contains a T at position 9.

23. The isolated antibody of paragraph 18, wherein the CDR-L1 of the light chain variable region comprises SEQ ID NO:28.

24. The isolated antibody of paragraph 23, wherein the amino acid sequence set forth in SEQ ID NO:28 contains a T at position 9.

25. The isolated antibody of paragraph 23, wherein the amino acid sequence set forth in SEQ ID NO:28 contains an S at position 9.

26. The isolated antibody of paragraph 18, wherein CDR-L2 of the light chain variable region comprises SEQ ID NO:22.

27. The isolated antibody of paragraph 18, wherein CDR-L2 of the light chain variable region comprises SEQ ID NO:26.

28. The isolated antibody of paragraph 14, wherein the CDR-L3 of the light chain variable region comprises SEQ ID NO:23.

29. The isolated antibody of paragraph 14, wherein the antibody or antigen-binding fragment thereof is selected from the group consisting of a Fab, a Fab' fragment, a F(ab')2 fragment and a whole antibody.

30. The isolated antibody of paragraph 14, wherein the antibody or antigen-binding fragment thereof is selected from the group consisting of a single chain antibody, an ScFv, and a univalent antibody lacking a hinge region.

31. The isolated antibody of paragraph 14, wherein said antibody binds human MLP with a $K_D$ of 10 nM or less.

32. The isolated antibody of paragraph 14, wherein said antibody binds glycosylated MLP secreted from an epithelial cancer cell line.

33. The isolated antibody of paragraph 14, wherein said antibody binds human MLP in an ELISA assay format.

34. The isolated antibody of paragraph 14, wherein said antibody is labeled with a detectable moiety.

35. The isolated antibody of paragraph 14, wherein said antibody is coupled to a therapeutic agent.

36. The isolated antibody of paragraph 14, wherein said antibody is immobilized on a substrate.

37. The isolated antibody of paragraph 14, wherein said antibody is humanized or fully human.

38. The isolated antibody of paragraph 14, or antigen binding fragment thereof, wherein said antibody comprises (i) a heavy chain variable region comprising CDR-H1 (SEQ ID NO:13), CDR-H2 (SEQ ID NO:14) and CDR-H3 (SEQ ID NO:15, SEQ ID NO:35 or SEQ ID NO:36) and (ii) a light chain variable region comprising CDR-L1 (SEQ ID NO:21), CDR-L2 (SEQ ID NO:22) and CDR-L3 (SEQ ID NO:23), and conservative modifications thereof.

39. The isolated antibody of paragraph 14, or antigen binding fragment thereof, wherein said antibody comprises a heavy chain variable region comprising CDR-H1 (SEQ ID NO:13), CDR-H2 (SEQ ID NO:16) and CDR-H3 (SEQ ID NO:15) and (ii) a light chain variable region comprising CDR-L1 (SEQ ID NO:24), CDR-L2 (SEQ ID NO:22) and CDR-L3 (SEQ ID NO:23), and conservative modifications thereof.

40. The isolated antibody of paragraph 14, or antigen binding fragment thereof, wherein said antibody comprises (i) a heavy chain variable region comprising CDR-H1 (SEQ ID NO:17), CDR-H2 (SEQ ID NO:18) and CDR-H3 (SEQ ID NO:19) and (ii) a light chain variable region comprising CDR-L1 (SEQ ID NO:25), CDR-L2 (SEQ ID NO:26) and CDR-L3 (SEQ ID NO:27), and conservative modifications thereof.

41. The isolated antibody of paragraph 14, wherein said antibody comprises a heavy chain variable domain comprising SEQ ID NO:7, or a variant thereof having a sequence at least 90% identical to SEQ ID NO:7.

42. The isolated antibody of paragraph 14, wherein said antibody comprises a heavy chain variable domain comprising SEQ ID NO:8, or a variant thereof having a sequence that is at least 90% identical to SEQ ID NO:8.

43. The isolated antibody of paragraph 14, wherein said antibody comprises a heavy chain variable domain comprising SEQ ID NO:9, or a variant thereof having a sequence that is at least at least 90% identical to SEQ ID NO:9.

44. A nucleic acid molecule encoding the amino acid sequence of an anti-MLP antibody, or fragment thereof, as set forth in any of paragraphs 14-43.

45. An expression cassette comprising a nucleic acid molecule encoding an anti-MLP antibody of the invention according to paragraph 44.

46. A cell comprising at least one of the nucleic acid molecules encoding an anti-MLP antibody of the invention according to paragraph 44 or paragraph 45.

47. An anti-MLP monoclonal antibody designated as Clone 11 produced by the hybridoma cell line deposited at the ATCC on Oct. 30, 2014 having the ATCC Designation Number PTA-121699.

48. An anti-MLP monoclonal antibody designated as Clone B produced by the hybridoma cell line deposited at the ATCC on Oct. 30, 2014 having the ATCC Designation Number PTA-121700.

49. An anti-MLP monoclonal antibody designated as Clone C produced by the hybridoma cell line deposited at the ATCC on Oct. 30, 2014 having the ATCC Designation Number PTA-121701.

50. A hybridoma cell line producing an anti-MLP antibody, wherein the cell line is selected from the group consisting of
(i) a hybridoma cell line secreting anti-MLP monoclonal antibody Clone 11 having the ATCC Designation Number PTA-121699;
(ii) a hybridoma cell line secreting anti-MLP monoclonal antibody Clone B having the ATCC Designation Number PTA-121700 and
(iii) a hybridoma cell line secreting anti-MLP monoclonal antibody Clone C having the ATCC Designation Number PTA-121701.

51. An isolated polypeptide comprising the amino acid sequence of SEQ ID NO:1, or a variant thereof having at least 95% identity to SEQ ID NO:1.

52. An isolated polypeptide comprising the amino acid sequence of SEQ ID NO:4, or a variant thereof having at least 95% identity to SEQ ID NO:4.

53. An isolated polypeptide comprising the amino acid sequence of SEQ ID NO:5, or a variant thereof having at least 95% identity to SEQ ID NO:5.

54. An isolated polypeptide comprising the amino acid sequence of SEQ ID NO:6, or a variant thereof having at least 95% identity to SEQ ID NO:6.

55. A method of generating an isolated anti-MLP antibody comprising culturing the cell of paragraph 46 or paragraph 50 under conditions allowing for expression of the nucleic acid molecules encoding the anti-MLP antibody and isolating said anti-MLP antibody.

56. A method of detecting or diagnosing epithelial cancer by determining the presence or amount of MLP in a biological sample from a test subject, the method comprising
(a) contacting a biological sample from a test subject with an anti-MLP antibody or antigen-binding fragment thereof in an in vitro immunoassay; and
(b) detecting the presence or absence of binding of said antibody, wherein the presence of binding indicates the presence or amount of MLP in the sample,
wherein the antibody or fragment thereof binds to an epitope in the C-terminal region of MLP, set forth as SEQ ID NO:4.

57. The method of paragraph 56, wherein said anti-MLP antibody is labeled with a detectable moiety and step (b) comprises detecting the presence or amount of said detectable moiety.

58. The method of paragraph 56 or paragraph 57, further comprising comparing the amount of MLP detected in accordance with step (b) with a reference standard or control sample from a healthy subject, wherein an increase of at least two-fold or higher (e.g., at least five-fold, or at least ten-fold) in the level of MLP in the test sample as compared to the control sample (or reference standard) indicates the presence of, or increased risk for developing an epithelial cancer, such as ovarian cancer or pancreatic cancer, in the test subject.

59. The method of paragraph 56, wherein the biological sample is selected from the group consisting of blood, serum, plasma and tissue.

60. The method of paragraph 56, wherein the anti-MLP antibody or fragment thereof is a monoclonal antibody that binds to the same epitope or competes for binding to MLP with a reference antibody selected from the group consisting of:
(i) the monoclonal anti-MLP antibody Clone 11 produced by the hybridoma cell line deposited at the ATCC on Oct. 30, 2014 under the ATCC Designation Number PTA-121699;
(ii) the monoclonal anti-MLP antibody Clone B produced by the hybridoma cell line deposited at the ATCC on Oct. 30, 2014 under the ATCC Designation Number PTA-121700; and
(iii) the monoclonal anti-MLP antibody clone C produced by the hybridoma cell line deposited at the ATCC on Oct. 30, 2014 under the ATCC Designation Number PTA-121701.

61. The method of paragraph 56, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

62. The method of paragraph 56, wherein the anti-MLP antibody or fragment thereof is a monoclonal antibody that comprises a heavy chain variable region and/or a light chain variable region set forth in Table 1, and conservative sequence modifications thereof.

63. The method of paragraph 56, further comprising performing an immunoassay with one or more additional antibodies that bind to ovarian and/or pancreatic cancer biomarkers.

64. The method of paragraph 56, wherein the test subject is: (i) apparently healthy (ii) has a family history of ovarian or pancreatic cancer; (iii) experiencing one or more symptoms associated with ovarian cancer; or (iv) known to be suffering from ovarian or pancreatic cancer and has had or is currently undergoing treatment for ovarian or pancreatic cancer.

65. The method of paragraph 56, wherein the method further comprises comparing the results of the assay from biological samples obtained from the test subject at one or more time points to assess the efficacy of a treatment regimen.

66. The method of paragraph 56, wherein the anti-MLP antibody is immobilized on a substrate.

67. The method of paragraph 56, wherein the immunoassay is an ELISA assay.

68. A method of detecting or diagnosing ovarian or pancreatic cancer in a test subject comprising (a) administering to a living test subject a humanized or fully human anti-MLP antibody or antigen-binding fragment thereof that binds to an epitope in the C-terminal region of MLP, set forth as SEQ ID NO:4; and (b) detecting the presence or absence or the amount of the antibody or fragment thereof bound to MLP, wherein detection of the presence or amount of MLP in the subject indicates the presence of ovarian or pancreatic cancer.

69. The method of paragraph 68, wherein the anti-MLP antibody is labeled with a detectable moiety suitable for in vivo use and step (b) comprises detecting the presence or amount of the detectable moiety.

70. The method of paragraph 68 or paragraph 69, wherein method is used in an imaging, intraoperative, endoscopic or intravascular procedure.

71. The method of paragraph 68, wherein the anti-MLP antibody or fragment thereof is a monoclonal antibody that binds to the same epitope or competes for binding to MLP with a reference antibody selected from the group consisting of:
  (i) the monoclonal anti-MLP antibody Clone 11 produced by the hybridoma cell line deposited at the ATCC on Oct. 30, 2014 under the ATCC Designation Number PTA-121699;
  (ii) the monoclonal anti-MLP antibody Clone B produced by the hybridoma cell line deposited at the ATCC on Oct. 30, 2014 under the ATCC Designation Number PTA-121700; and
  (iii) the monoclonal anti-MLP antibody clone C produced by the hybridoma cell line deposited at the ATCC on Oct. 30, 2014 under the ATCC Designation Number PTA-121701.

72. The method of paragraph 68, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

73. The method of paragraph 68, wherein the test subject is: (i) apparently healthy (ii) has a family history of ovarian or pancreatic cancer; (iii) experiencing one or more symptoms associated with ovarian cancer; or (iv) known to be suffering from ovarian or pancreatic cancer and has had or is currently undergoing treatment for ovarian or pancreatic cancer.

74. A method of treating a subject suffering from ovarian or pancreatic cancer comprising administering to an individual suffering from ovarian or pancreatic cancer a humanized or fully human anti-MLP antibody or antigen-binding fragment thereof that binds to an epitope in the C-terminal region of MLP, set forth as SEQ ID NO:4, wherein the antibody or fragment thereof is coupled to a therapeutic agent.

75. The method of paragraph 74, wherein the therapeutic agent is a chemotherapeutic agent.

76. The method of paragraph 74, wherein the anti-MLP antibody or fragment thereof is a monoclonal antibody that binds to the same epitope or competes for binding to MLP with a reference antibody selected from the group consisting of:
  (i) the monoclonal anti-MLP antibody Clone 11 produced by the hybridoma cell line deposited at the ATCC on Oct. 30, 2014 under the ATCC Designation Number PTA-121699;
  (ii) the monoclonal anti-MLP antibody Clone B produced by the hybridoma cell line deposited at the ATCC on Oct. 30, 2014 under the ATCC Designation Number PTA-121700; and
  (iii) the monoclonal anti-MLP antibody clone C produced by the hybridoma cell line deposited at the ATCC on Oct. 30, 2014 under the ATCC Designation Number PTA-121701.

77. The method of paragraph 74, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

78. A method of detecting or diagnosing a mucin-secreting type of cancer by determining the presence or amount of MLP in a biological sample from a test subject, the method comprising:
  (a) contacting a biological sample from a test subject with an anti-MLP antibody or antigen-binding fragment thereof in an in vitro immunoassay; and
  (b) detecting the presence or absence of binding of said antibody, wherein the presence of binding indicates the presence or amount of MLP in the sample,
  wherein the antibody or fragment thereof binds to an epitope in the C-terminal region of MLP, set forth as SEQ ID NO:4.

79. The method of paragraph 78, wherein said anti-MLP antibody is labeled with a detectable moiety and step (b) comprises detecting the presence or amount of said detectable moiety.

80. The method of paragraph 78 or paragraph 79, further comprising comparing the amount of MLP detected in accordance with step (b) with a reference standard or control sample from a healthy subject, wherein an increase of at least two-fold or higher (e.g., at least five-fold, or at least ten-fold) in the level of MLP in the test sample as compared to the control sample (or reference standard) indicates the presence of, or increased risk for developing an mucin-secreting type of cancer in the test subject.

81. The method of paragraph 78, wherein the biological sample is selected from the group consisting of blood, serum, plasma and tissue.

82. The method of paragraph 78, wherein the anti-MLP antibody or fragment thereof is a monoclonal antibody that binds to the same epitope or competes for binding to MLP with a reference antibody selected from the group consisting of:
  (i) the monoclonal anti-MLP antibody Clone 11 produced by the hybridoma cell line deposited at the ATCC on Oct. 30, 2014 under the ATCC Designation Number PTA-121699;
  (ii) the monoclonal anti-MLP antibody Clone B produced by the hybridoma cell line deposited at the ATCC on Oct. 30, 2014 under the ATCC Designation Number PTA-121700; and
  (iii) the monoclonal anti-MLP antibody clone C produced by the hybridoma cell line deposited at the ATCC on Oct. 30, 2014 under the ATCC Designation Number PTA-121701.

83. The method of paragraph 78, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

84. The method of paragraph 78, wherein the anti-MLP antibody or fragment thereof is a monoclonal antibody that comprises a heavy chain variable region and/or a light chain variable region set forth in Table 1, and conservative sequence modifications thereof.

85. The method of paragraph 78, wherein the mucin-secreting cancer type is selected from the group consisting of ovarian, pancreatic, colorectal, breast, appendiceal, lung, renal, cervical, biliary, esophageal and epithelial skin cancer.

86. The method of paragraph 78, wherein the mucin-secreting cancer type is ovarian or pancreatic cancer.

87. The method of paragraph 86, further comprising performing an immunoassay with one or more additional antibodies that bind to ovarian and/or pancreatic cancer biomarkers.

88. The method of paragraph 78, wherein the test subject is: (i) apparently healthy (ii) has a family history of cancer; (iii) experiencing one or more symptoms associated with cancer; or (iv) known to be suffering from cancer and has had or is currently undergoing treatment for cancer.

89. The method of paragraph 78, wherein the method further comprises comparing the results of the assay from biological samples obtained from the test subject at one or more time points to assess the efficacy of a treatment regimen.

90. The method of paragraph 78, wherein the anti-MLP antibody is immobilized on a substrate.

91. The method of paragraph 78, wherein the immunoassay is an ELISA assay.

92. A method of detecting or diagnosing the presence of a mucin-secreting cancer in a test subject comprising (a) administering to a living test subject a humanized or fully human anti-MLP antibody or antigen-binding fragment thereof that binds to an epitope in the C-terminal region of MLP, set forth as SEQ ID NO:4; and (b) detecting the presence or absence or the amount of the antibody or fragment thereof bound to MLP, wherein detection of the presence or amount of MLP in the subject indicates the presence of mucin-secreting cancer.

93. The method of paragraph 92, wherein the anti-MLP antibody is labeled with a detectable moiety suitable for in vivo use and step (b) comprises detecting the presence or amount of the detectable moiety.

94. The method of paragraph 92 or paragraph 93, wherein method is used in an imaging, intraoperative, endoscopic or intravascular procedure.

95. The method of paragraph 92, wherein the anti-MLP antibody or fragment thereof is a monoclonal antibody that binds to the same epitope or competes for binding to MLP with a reference antibody selected from the group consisting of:
  (i) the monoclonal anti-MLP antibody Clone 11 produced by the hybridoma cell line deposited at the ATCC on Oct. 30, 2014 under the ATCC Designation Number PTA-121699;
  (ii) the monoclonal anti-MLP antibody Clone B produced by the hybridoma cell line deposited at the ATCC on Oct. 30, 2014 under the ATCC Designation Number PTA-121700; and
  (iii) the monoclonal anti-MLP antibody clone C produced by the hybridoma cell line deposited at the ATCC on Oct. 30, 2014 under the ATCC Designation Number PTA-121701.

96. The method of paragraph 92, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

97. The method of paragraph 92, wherein the test subject is: (i) apparently healthy (ii) has a family history of cancer; (iii) experiencing one or more symptoms associated with cancer; or (iv) known to be suffering from cancer and has had or is currently undergoing treatment for cancer.

98. A method of treating a subject suffering from a mucin-secreting type of cancer comprising administering to an individual suffering from a mucin-secreting type of cancer a humanized or fully human anti-MLP antibody or antigen-binding fragment thereof that binds to an epitope in the C-terminal region of MLP, set forth as SEQ ID NO:4, wherein the antibody or fragment thereof is coupled to a therapeutic agent.

99. The method of paragraph 98, wherein the therapeutic agent is a chemotherapeutic agent.

100. The method of paragraph 98, wherein the anti-MLP antibody or fragment thereof is a monoclonal antibody that binds to the same epitope or competes for binding to MLP with a reference antibody selected from the group consisting of:
  (i) the monoclonal anti-MLP antibody Clone 11 produced by the hybridoma cell line deposited at the ATCC on Oct. 30, 2014 under the ATCC Designation Number PTA-121699;
  (ii) the monoclonal anti-MLP antibody Clone B produced by the hybridoma cell line deposited at the ATCC on Oct. 30, 2014 under the ATCC Designation Number PTA-121700; and (iii) the monoclonal anti-MLP antibody clone C produced by the hybridoma cell line deposited at the ATCC on Oct. 30, 2014 under the ATCC Designation Number PTA-121701.

101. The method of paragraph 98, wherein the anti-MLP antibody or fragment thereof is a monoclonal antibody having a heavy chain variable region CDR-H3 sequence comprising an amino acid sequence set forth as SEQ ID NO:15, SEQ ID NO:35, SEQ ID NO:36 or SEQ ID NO:19, and conservative sequence modifications thereof, and having a light chain variable region CDR-L3 sequence comprising an amino acid sequence set forth as SEQ ID NO:23 or SEQ ID NO:27, and conservative sequence modifications thereof.

102. The method of paragraph 98, wherein the mucin-secreting cancer type is selected from the group consisting of ovarian, pancreatic, colorectal, breast, appendiceal, lung, renal, cervical, biliary, esophageal and epithelial skin cancer.

103. A composition comprising an anti-MLP antibody as set forth in any of paragraphs 1-43.

104. A substrate for use in an immunoassay comprising at least one anti-MLP antibody as set forth in any of paragraphs 1-43.

105. A kit for detecting the presence of MLP in a biological sample, said kit comprising (a) at least one container, and (b) at least one anti-MLP antibody as set forth in any of paragraphs 1-43.

While the preferred embodiment of the invention has been illustrated and described, it will be appreciated that various changes can be made therein without departing from the spirit and scope of the invention.

The invention claimed is:

1. An isolated monoclonal antibody, or antigen binding fragment thereof, that specifically binds to an epitope in the C-terminal region of human mucin-like protein, set forth as SEQ ID NO:4, wherein the monoclonal antibody or antigen-binding fragment comprises:
   (i) a heavy chain variable region comprising a CDR-H1 set forth as SEQ ID NO:3; a CDR-H2 set forth as SEQ ID NO:20, wherein X at position 9 is T or P and wherein X at position 10 is S or T; and a CDR-H3 set forth as SEQ ID NO:36, wherein X at position 14 is S or F; and a light chain variable region comprising a CDR-L1 set forth as SEQ ID NO:28, wherein X at position 9 is T or S; a CDR-L2 set forth as SEQ ID NO:22 and a CDR-L3 set forth as SEQ ID NO:23; or
   (ii) a heavy chain variable region comprising a CDR-H1 set forth as SEQ ID NO:17; a CDR-H2 set forth as SEQ ID NO:18; a CDR-H3 set forth as SEQ ID NO:19 and a light chain variable region comprising a CDR-L1 set forth as SEQ ID NO:25; a CDR-L2 set forth as SEQ ID NO:26 and a CDR-L3 set forth as SEQ ID NO:27.

2. The monoclonal antibody or antigen binding fragment thereof of claim 1, wherein at least one of the following applies:
   (i) the antibody is a recombinant, humanized or chimeric antibody; or
   (ii) the antibody is a fully human antibody.

3. The antibody of claim 1, wherein at least one of the following applies:
   said antibody according to (i) comprising a variable region of the heavy chain comprising or consisting of a sequence which is at least 90% identical to an amino acid sequence selected from the group consisting of SEQ ID NO:7, SEQ ID NO:8 and a variable region of the light chain comprising or consisting of a sequence which is at least 90% identical to an amino acid sequence selected from the group consisting of SEQ ID NO:10 and SEQ ID NO: 11; or
   said antibody according to (ii) comprising a variable region of the heavy chain comprising or consisting of a sequence which is at least 90% identical to an amino acid sequence set forth as SEQ ID NO:9 and a light chain comprising or consisting of a sequence which is at least 90% identical to an amino acid sequence set forth as SEQ ID NO:12.

4. The antibody of claim 1, wherein said antibody is labeled with a detectable moiety and/or wherein said antibody is coupled to a therapeutic agent.

5. The antibody of claim 1, wherein said antibody is immobilized on a substrate.

6. The antibody or antigen-binding fragment thereof of claim 1 (i), wherein said antibody or antigen binding fragment comprises:
   a heavy chain variable region comprising CDR-H1 set forth as SEQ ID NO: 13, CDR-H2 set forth as SEQ ID NO:14 and CDR-H3 set forth as SEQ ID NO:15 and comprising a light chain variable region comprising CDR-L1 set forth as SEQ ID NO:21, CDR-L2 set forth as SEQ ID NO:22 and CDR-L3 set forth as SEQ ID NO:23.

7. The antibody or antigen-binding fragment thereof of claim 1 (i), wherein said antibody or antigen binding fragment comprises:
   a heavy chain variable region comprising CDR-H1 set forth as SEQ ID NO: 13; CDR-H2 set forth as SEQ ID NO:16 and CDR-H3 set forth as SEQ ID NO:35 and comprising a light chain variable region comprising CDR-L1 set forth as SEQ ID NO:24, CDR-L2 set forth as SEQ ID NO:22 and CDR-L3 set forth as SEQ ID NO:23.

8. The antibody of claim 1, wherein the antibody or antigen-binding fragment thereof is selected from the group consisting of a Fab, a Fab' fragment, a F(ab')2 fragment, a whole antibody, a single chain antibody, an ScFv, and a univalent antibody lacking a hinge region.

9. A composition comprising an anti-MLP antibody as set forth in claim 1.

10. A kit for detecting the presence of MLP in a biological sample, said kit comprising (a) at least one container, and (b) at least one anti-MLP antibody as set forth in claim 1.

* * * * *

UNITED STATES PATENT AND TRADEMARK OFFICE
CERTIFICATE OF CORRECTION

PATENT NO.        : 10,626,184 B2
APPLICATION NO.   : 15/615588
DATED             : April 21, 2020
INVENTOR(S)       : Hans-Wilhelm Schwaeble It is certified that error appears in the above-identified patent and that said Letters Patent is hereby corrected as shown below:

On the Title Page

Page 2, in Column 2, item (56), under Other Publications, Line 67, delete "specic" and insert -- specific --, therefor.

In the Specification

In Column 1, Line 12, delete "2016;" and insert -- 2016; now pending; --, therefor.

In Column 1, Line 57, delete "better then" and insert -- better than --, therefor.

In Column 2, Lines 21-22, delete "PTA-121699." and insert -- PTA-121699; --, therefor.

In Column 4, Line 25, delete "present or amount" and insert -- presence or amount --, therefor.

In Column 7, Line 41, delete "of amino acids amino acid" and insert -- of amino acid --, therefor.

In Column 7, Line 55, delete "of amino acids amino acid" and insert -- of amino acid --, therefor.

In Column 8, Line 53, delete "CH domains (CH)" and insert -- constant domains (CH) --, therefor.

In Column 9, Line 12, delete "refers to that" and insert -- refers to the --, therefor.

In Column 10, Line 16, delete "Rosenburg and Moore eds.," and insert -- Rosenberg and Moore eds., --, therefor.

In Column 10, Line 52, delete "8 9" and insert -- 8, 9 --, therefor.

In Column 22, Line 11, delete "TVRESSS" and insert -- TVHESSS --, therefor.

Signed and Sealed this
Thirteenth Day of September, 2022

*Katherine Kelly Vidal*

Katherine Kelly Vidal
*Director of the United States Patent and Trademark Office*

In Column 28, Line 45, delete "(i.e," and insert -- (i.e., --, therefor.

In Column 28, Line 45, delete "NO: 1)" and insert -- NO: 1). --, therefor.

In Column 29, Line 23, delete "8 9" and insert -- 8, 9 --, therefor.

In Column 35, Line 10, delete "(i.e," and insert -- (i.e., --, therefor.

In Column 37, Line 10, delete "adjacent the" and insert -- adjacent to the --, therefor.

In Column 37, Line 28, delete "in in" and insert -- in --, therefor.

In Column 38, Line 8, delete "(e.g," and insert -- (e.g., --, therefor.

In Column 38, Line 26, delete "orthophenylene diamine (OPD)" and insert -- ortho phenylenediamine (OPD) --, therefor.

In Column 39, Lines 8-9, delete "camptothecans, proteosome" and insert -- camptothecins proteasome --, therefor.

In Column 39, Line 9, delete "proteosome inhibitors," and insert -- proteasome inhibitor, --, therefor.

In Column 39, Line 16, delete "proteosome inhibitors," and insert -- proteasome inhibitor, --, therefor.

In Column 39, Lines 59-60, delete "3-(2-pyridyldithio)proprionate (SPDP)." and insert -- 3-(2-pyridyldithio) propionate (SPDP) --, therefor.

In Column 40, Line 25, delete "stroma" and insert -- stromal --, therefor.

In Column 42, Line 20, delete "ovarian malignances" and insert -- ovarian malignancies --, therefor.

In Column 42, under table 7, Line 48, delete "Physiotherpists," and insert -- Physiotherapists --, therefor.

In Column 42, under table 7, Line 50, delete "Physiotherpists," and insert -- Physiotherapists --, therefor.

In Column 52, Line 42, delete "formulatory agents" and insert -- formulary agents --, therefor.

In Column 52, Line 50, delete "milligrams protein" and insert -- milligrams of protein --, therefor.

In Column 54, Line 41, delete "globlet cells" and insert -- goblet cells --, therefor.

In Column 55, Line 21, delete "molecule weight" and insert -- molecular weight --, therefor.

In Column 56, Line 33, delete "molecule weight" and insert -- molecular weight --, therefor.

CERTIFICATE OF CORRECTION (continued)
U.S. Pat. No. 10,626,184 B2

In Column 57, Line 8, delete "100" and insert -- 100µL --, therefor.

In Column 65, Line 44, delete "consisting of" and insert -- consisting of: --, therefor.

In Column 65, Line 50, delete "PTA-121700 and" and insert -- PTA-121700; and --, therefor.

In Column 68, Lines 66-67, delete "an mucin-secreting" and insert -- a mucin-secreting --, therefor.

In the Claims

In Column 93, Line 25, Claim 1, delete "SEQ ID NO:3" and insert -- SEQ ID NO:13 --, therefor.